(12) United States Patent
Iyer et al.

(10) Patent No.: US 11,274,348 B2
(45) Date of Patent: Mar. 15, 2022

(54) USE OF BIOMARKERS IN DETERMINING SUSCEPTIBILITY TO DISEASE TREATMENT

(71) Applicant: SINGAPORE HEALTH SERVICES PTE LTD, Singapore (SG)

(72) Inventors: Narayanan Gopalakrishna Iyer, Singapore (SG); Daniel Shao-Weng Tan, Singapore (SG)

(73) Assignee: Singapore Health Services Pte Ltd, Singapore (SG)

(*) Notice: Subject to any disclaimer, the term of this patent is extended or adjusted under 35 U.S.C. 154(b) by 324 days.

(21) Appl. No.: 16/306,395

(22) PCT Filed: Jun. 5, 2017

(86) PCT No.: PCT/SG2017/050284
§ 371 (c)(1),
(2) Date: Nov. 30, 2018

(87) PCT Pub. No.: WO2017/209697
PCT Pub. Date: Dec. 7, 2017

(65) Prior Publication Data
US 2020/0318196 A1    Oct. 8, 2020

Related U.S. Application Data

(60) Provisional application No. 62/345,081, filed on Jun. 3, 2016.

(51) Int. Cl.
*C12Q 1/6886* (2018.01)

(52) U.S. Cl.
CPC ..... *C12Q 1/6886* (2013.01); *C12Q 2600/106* (2013.01); *C12Q 2600/156* (2013.01);
(Continued)

(58) Field of Classification Search
CPC ........... C12Q 1/6886; C12Q 2600/106; C12Q 2600/156; C12Q 2600/158; C12Q 2600/178; G01N 2333/485; G01N 2800/60
See application file for complete search history.

(56) References Cited

FOREIGN PATENT DOCUMENTS

WO      2006/086777 A2     8/2006

OTHER PUBLICATIONS

Qi HL, Li CS, Qian CW, Xiao YS, Yuan YF, Liu QY, Liu ZS. The long noncoding RNA, EGFR-AS1, a target of GHR, increases the expression of EGFR in hepatocellular carcinoma. Tumour Biol. Jan. 2016;37(1) 1079-1089. doi:10.1007/s13277-015-3887-z. PMID: 26271667. Published Aug. 14, 2015. (Year: 2016).*

(Continued)

*Primary Examiner* — Jehanne S Sitton
*Assistant Examiner* — Daniel W Nielsen
(74) *Attorney, Agent, or Firm* — Barnes & Thornburg LLP

(57) ABSTRACT

The present invention refers to a method of predicting susceptibility of a subject suffering from cancer to a treatment with an anti-cancer drug, wherein the method comprises detecting the presence or absence of a genetic alteration in a long non-coding RNA (lncRNA) that resides in an antisense strand of an oncogene, wherein the genetic alteration disrupts expression of the oncogene, and wherein the subject is predicted to be more susceptible to the treatment if the genetic alteration is present. In particular, the genetic alteration is a silent G>A mutation at Q787Q of the oncogene epidermal growth factor receptor (EGFR). Also disclosed herein is a method of treating a subject suffering from cancer, who was shown to have a genetic alteration in lncRNA that resides in an antisense strand of an oncogene.

7 Claims, 21 Drawing Sheets

Specification includes a Sequence Listing.

(52) U.S. Cl.
CPC . *C12Q 2600/158* (2013.01); *C12Q 2600/178* (2013.01); *G01N 2333/485* (2013.01); *G01N 2800/60* (2013.01)

(56) References Cited

OTHER PUBLICATIONS

Liu et al., A novel mutation in SIRT1-AS leading to a decreased risk of HCC, Oncol Reports (2015) 34:2343-2350 (Year: 2015).*
Chen et al., SIRT1 Promotes Tumorigenesis and Resistance to Chemotherapy in Hepatocellular Carcinoma and its Expression Predicts Poor Prognosis, Ann Surg Oncol (2012) 19: 2011-2019 (Year: 2012).*
Longatto-Filho et al., Molecular characterization of EGFR, PDGFRA and VEGFR2 in cervical adenosquamous carcinoma, BMC Cancer (2009) 9(212):pp. 6 (Year: 2009).*
SNP FAQ Archive, "dbSNP Data Statistics: What is the current number of SNPs in the human genome?". NCBI Bookshelf. (Year: 2006).*
Sasaki et al., "EGFR polymorphism of the kinase domain in Japanese lung cancer", J. Surg. Res. (2008): 148:260-263 (Year: 2008).*
Bonin et al., A synonymous EGFR polymorphism predicting responsiveness to anti-EGFR therapy in metastatic colorectal cancer patients, Tumor Biol (2016) 37: 7295-7303 (Year: 2015).*
Taguchi et al., Involvement of EGFR in the response of squamous cell carcinoma of the head and neck cell lines to gefitinib, Oncol Rep (2008) 19:65-71 (Year: 2008).*
Fung et al., Identification of epidermal growth factor receptor (EGFR) genetic variants that modify risk for head and neck squamous cell carcinoma, Cancer Lett (2015) 357:549-556 (Year: 2015).*
PCT Search Report and Written Opinion prepared for PCT/SG2017/050284, completed Aug. 7, 2017.
Zhang T., et al., "SIRT1 Expression Is Associated with the Chemotherapy Response and Prognosis of Patients with Advanced NSCLC. PLoS One," Nov. 2013, vol. 8, No. 11, pp. 1-9.
Liu J., et al., "A novel mutation in SIRT1-AS leading to a decreased risk of HCC. Oncol Rep," Aug. 2015, vol. 34, No. 5, pp. 2343-2350.
Bonin S., et al., "A synonymous EGFR polymorphism predicting responsiveness to anti-EGFR therapy in metastatic colorectal cancer patients," 2015, Tumor Biol, vol. 37, No. 6, pp. 7295-7303. (Abstract Only).
Gong W.J., et al., "Association of well-characterized lung cancer lncRNA polymorphisms with lung cancer susceptibility and platinum-based chemotherapy response," Jan. 2016, Tumour Biol, 5 , vol. 37, No. 6, pp. 8349-8358. (Abstract Only).
Hu L., et al., "Clinical Significance of Long Non-Coding RNA CASC8 rs10505477 Polymorphism in Lung Cancer Susceptibility, Platinum-Based Chemotherapy Response, and Toxicity. Int J Environ Res Public Health," May 2016, vol. 13, No. 6, pp. 1-12.
Cripps C, Winquist E, Devries MC, et al. Epidermal growth factor receptor targeted therapy in stages III and IV head and neck cancer. Current oncology 2010;17:37-48.
Montero PH, Patel PD, Palmer FL, et al. Changing trends in smoking and alcohol consumption in patients with oral cancer treated at Memorial Sloan-Kettering Cancer Center from 1985 to 2009. Archives of otolaryngology—head & neck surgery 2012;138:817-22.
Krishna Rao SV, Mejia G, Roberts-Thomson K, Logan R. Epidemiology of oral cancer in Asia in the past decade—an update (2000-2012). Asian Pacific journal of cancer prevention : APJCP 2013;14:5567-77.
Warnakulasuriya S. Global epidemiology of oral and oropharyngeal cancer. Oral oncology 2009;45:309-16.
Cancer Incidence and Mortality Worldwide: IARC Cancer Base No. 11. International Agency for Research on Cancer, 2013. (Accessed Nov. 22, 2014, at http://globocan.iarc.fr.).
Sacco AG, Cohen EE. Current Treatment Options for Recurrent or Metastatic Head and Neck Squamous Cell Carcinoma. Journal of clinical oncology : official journal of the American Society of Clinical Oncology 2015;33:3305-13.
Vermorken JB, Mesia R, Rivera F, et al. Platinum-based chemotherapy plus cetuximab in head and neck cancer. The New England journal of medicine 2008;359:1116-27.
Echarri MJ, Lopez-Martin A, Hitt R. Targeted Therapy in Locally Advanced and Recurrent/Metastatic Head and Neck Squamous Cell Carcinoma (LA-R/M HNSCC). Cancers 2016;8.
Licitra L, Mesia R, Rivera F, et al. Evaluation of EGFR gene copy number as a predictive biomarker for the efficacy of cetuximab in combination with chemotherapy in the first-line treatment of recurrent and/or metastatic squamous cell carcinoma of the head and neck: EXTREME study. Annals of oncology: official journal of the European Society for Medical Oncology / ESMO 2011;22:1078-87.
Stewart JS, Cohen EE, Licitra L, et al. Phase III study of gefitinib compared with intravenous methotrexate for recurrent squamous cell carcinoma of the head and neck [corrected]. Journal of clinical oncology : official journal of the American Society of Clinical Oncology 2009;27:1864-71.
Kirby AM, A'Hern RP, D'Ambrosio C, et al. Gefitinib (ZD1839, Iressa) as palliative treatment in recurrent or metastatic head and neck cancer. British journal of cancer 2006;94:631-6.
Cohen EE, Kane MA, List MA, et al. Phase II trial of gefitinib 250 mg daily in patients with recurrent and/or metastatic squamous cell carcinoma of the head and neck. Clinical cancer research : an official journal of the American Association for Cancer Research 2005;11:8418-24.
Thomas F, Rochaix P, Benlyazid A, et al. Pilot study of neoadjuvant treatment with erlotinib in nonmetastatic head and neck squamous cell carcinoma. Clinical cancer research : an official journal of the American Association for Cancer Research 2007;13:7086-92.
Soulieres D, Senzer NN, Vokes EE, Hidalgo M, Agarwala SS, Siu LL. Multicenter phase II study of erlotinib, an oral epidermal growth factor receptor tyrosine kinase inhibitor, in patients with recurrent or metastatic squamous cell cancer of the head and neck. Journal of clinical oncology : official journal of the American Society of Clinical Oncology 2004;22:77-85.
Tan DS, Thomas GV, Garrett MD, et al. Biomarker-driven early clinical trials in oncology: a paradigm shift in drug development. Cancer journal 2009;15:406-20.
Vettore AL, Ramnarayanan K, Poore G, et al. Mutational landscapes of tongue carcinoma reveal recurrent mutations in genes of therapeutic and prognostic relevance. Genome medicine 2015;7:98.
Tan DS, Wang W, Leong HS, et al. Tongue carcinoma infrequently harbor common actionable genetic alterations. BMC cancer 2014;14:679.
Cohen EE, Halpern AB, Kasza K, Kocherginsky M, Williams R, Vokes EE. Factors associated with clinical benefit from epidermal growth factor receptor inhibitors in recurrent and metastatic squamous cell carcinoma of the head and neck. Oral oncology 2009;45:e155-60.
Tan EH, Goh C, Lim WT, et al. Gefitinib, cisplatin, and concurrent radiotherapy for locally advanced head and neck cancer: EGFR FISH, protein expression, and mutational status are not predictive biomarkers. Annals of oncology : official journal of the European Society for Medical Oncology / ESMO 2012;23:1010-6.
Taguchi T, Tsukuda M, Imagawa-Ishiguro Y, Kato Y, Sano D. Involvement of EGFR in the response of squamous cell carcinoma of the head and neck cell lines to gefitinib. Oncology reports 2008;19:65-71.
Leong HS, Chong FT, Sew PH, et al. Targeting cancer stem cell plasticity through modulation of epidermal growth factor and insulin-like growth factor receptor signaling in head and neck squamous cell cancer. Stem cells translational medicine 2014;3:1055-65.
Zhao Y, Hamza MS, Leong HS, et al. Kruppel-like factor 5 modulates p53-independent apoptosis through Pim1 survival kinase in cancer cells. Oncogene 2008;27:1-8.
Guillaudeau A, Durand K, Rabinovitch-Chable H, et al. Adult diffuse gliomas produce mRNA transcripts encoding EGFR isoforms lacking a tyrosine kinase domain. International journal of oncology 2012;40:1142-52.

(56) References Cited

OTHER PUBLICATIONS

Adamczyk KA, Klein-Scory S, Tehrani MM, et al. Characterization of soluble and exosomal forms of the EGFR released from pancreatic cancer cells. Life sciences 2011;89:304-12.

Iyer MK, Niknafs YS, Malik R, et al. The landscape of long noncoding RNAs in the human transcriptome. Nature genetics 2015;47:199-208.

Schmitt AM, Chang HY. Long Noncoding RNAs in Cancer Pathways. Cancer cell 2016;29:452-63.

Brown JA, Bulkley D, Wang J, et al. Structural insights into the stabilization of MALAT1 noncoding RNA by a bipartite triple helix. Nature structural & molecular biology 2014;21:633-40.

Arun G, Diermeier S, Akerman M, et al. Differentiation of mammary tumors and reduction in metastasis upon Malat1 lncRNA loss. Genes Dev 2016;30:34-51.

Leucci E, Vendramin R, Spinazzi M, et al. Melanoma addiction to the long non-coding RNA SAMMSON. Nature 2016;531:518-22.

Qi HL, Li CS, Qian CW, et al. The long noncoding RNA, EGFR-AS1, a target of GHR, increases the expression of EGFR in hepatocellular carcinoma. Tumour biology: the journal of the International Society for Oncodevelopmental Biology and Medicine 2016;37:1079-89.

Blythe AJ, Fox AH, Bond CS. The ins and outs of lncRNA structure: How, why and what comes next? Biochimica et biophysica acta 2016;1859:46-58.

Ji Z, Song R, Regev A, Struhl K. Many lncRNAs, 5'UTRs, and pseudogenes are translated and some are likely to express functional proteins. eLife 2015;4:e08890.

Munroe SH, Lazar MA. Inhibition of c-erbA mRNA splicing by a naturally occurring antisense RNA. J Biol Chem 1991;266:22083-6.

Halle C, Lando M, Svendsrud DH, et al. Membranous expression of ectodomain isoforms of the epidermal growth factor receptor predicts outcome after chemoradiotherapy of lymph node-negative cervical cancer. Clinical cancer research : an official journal of the American Association for Cancer Research 2011;17:5501-12.

Lococo F, Paci M, Rapicetta C, et al. Preliminary Evidence on the Diagnostic and Molecular Role of Circulating Soluble EGFR in Non-Small Cell Lung Cancer. International journal of molecular sciences 2015;16:19612-30.

Romero-Ventosa EY, Blanco-Prieto S, Gonzalez-Pineiro AL, Rodriguez-Berrocal FJ, Pineiro-Corrales G, Paez de la Cadena M. Pretreatment levels of the serum biomarkers CEA, CYFRA 21-1, SCC and the soluble EGFR and its ligands EGF, TGF-alpha, HB-EGF in the prediction of outcome in erlotinib treated non-small-cell lung cancer patients. SpringerPlus 2015;4:171.

Albitar L, Pickett G, Morgan M, Wilken JA, Maihle NJ, Leslie KK. EGFR isoforms and gene regulation in human endometrial cancer cells. Molecular cancer 2010;9:166.

Tan DS, Adjei AA. Toward High-Precision Genomic Biomarkers: The Importance of Context. Journal of thoracic oncology : official publication of the International Association for the Study of Lung Cancer 2015;10:1237-9.

Zhou T, Kim Y, MacLeod AR. Targeting Long Noncoding RNA with Antisense Oligonucleotide Technology as Cancer Therapeutics. Methods in molecular biology 2016;1402:199-213.

Golan T, Khvalevsky EZ, Hubert A, et al. RNAi therapy targeting KRAS in combination with chemotherapy for locally advanced pancreatic cancer patients. Oncotarget 2015;6:24560-70.

Bassi EN et al. Exploring the Role of Soluble Factors Associated with Immune Regulatory Properties of Mesenchymal Stem Cells. Stem Cell Rev and Rep (2012) 8:329-342.

Albitar, L., et al. "EGFR isoforms and gene regulation in human endometrial cancer cells" Molecular Cancer, 2010, 9:166, pp. 1-13.

Qi, Hao-long, et al. "The long noncoding RNA, EGFR-AS1, a target of GHR, increases the expression of EGFR in hepatocellular carcinoma" Tumor Biol, 2016, 37, pp. 1079-1089.

Qureshi, R. et al. "Mutation analysis of EGFR and its correlation with the HPV in Indian cervical cancer patients" Tumor Biol, 2016, 37, pp. 9089-9098.

Taguchi, T. et al. "Involvement of EGFR in the response of squamous cell carcinoma of the head and neck cell to gefitinib" Oncology Reports, 2008, 19, pp. 657-671.

Guillaudeau, A. et al. "EGFR Soluble Isoforms and Their Transcripts Are Expressed in Meningiomas" PLOS one, 2012, 7:5, pp. 1-12.

Amador, M.L., et al. "An Epidermal Growth Factor Receptor Intron 1 Polymorphism Mediates Response to Epidermal Growth Factor Receptor Inhibitors" Cancer Research, 2004, 64, pp. 9139-9143.

Ma, F. et al. "Polymorphisms of EGFR predict clinical outcome in advanced non-small-cell lung cancer patients treated with Gefitnib" Lung Cancer, 2009, 66, pp. 114-119.

Extended European Search Report prepared for Application 178071262.2, completed Dec. 20, 2019.

Supplementary European Search Report prepared for Application 17807126.2, dated Jan. 28, 2020.

Tan, D.S.W., et al. "Long noncding RNA EGFR-AS1 mediates epidermal growth factor receptor addiction and modulates treatment response in squamous cell carcinoma" Nature Medicine 2017, 23:10, pp. 1167-1180.

Bonin, S. et al. "A synonymous EGFR polymorphism predicting responsiveness to anti-EGFR therapy in metastatic colorectal cancer patients" Tumor Biol, 2016, 37:6, 7295-303 (Abstract Only).

Miu, X.L, et al. "Gefitinib-Sensitive Mutations of the Epidermal Growth Factor Receptor Tyrosine Kinase Domain in Chinese Patients with Non-Small Cell Lung Cancer" Clinical Cancer Research, 2005, 11:12, pp. 4289-4294.

Sasaki, H. et al. "EGFR Polymorphism of the Kinase Domain in Japanese Lung Cancer" Journal of Surgical Research, 2008, 148, pp. 260-263.

Communication pursuant to Article 94(3) EPC for EP17807126.2-1111, dated Oct. 27, 2020.

Written Opinion for EP 11201810694W, dated Apr. 5, 2020.

Chinese First Office Action with English translation for Application No. 2017800474300 dated Aug. 31, 2021.

EPO Communication pursuant to Article 94(3) for Application No. 17807126.2 dated Aug. 10, 2021.

\* cited by examiner

FIG. 4B

| | (1° Cell line) | (1° Cell line) | | (1° Cell line) | (1° Cell line) | (1° Cell line) | (1° Cell line) | (1° Cell line) |
|---|---|---|---|---|---|---|---|---|
| Tumor Type | NCC-HN19 | NCC-HN137 | NCC-HN64 | NCC-HN148 | NCC-HN124 | NCC-HN43 | NCC-HN1 | NCC-HN154 | NCC-HN159 | NCC-HN160 |
| Genotype | AA | AA | AA | AA | AG | GG | GG | GG | GG | GG |
| Cell line Gefitinib IC50 (uM) | 0.07 | 0.2 | 0.257 | 0.583 | 11.355 | 9.5 | 11 | - | - | >20 |
| Relative AS1 Fold Change | 0.27 | 1.22 | 0.17 | 1.00 | 1.000 | 0.83 | 1.00 | 0.86 | 0.000 | 0.000 |
| Relative Isoform D/A Fold Change | | | | | 1.000 | | 1.00 | 0.332 | 0.000 | 0.000 |
| RNA scope (AMPL score) on FFPE tissue | | | | | | | | | | |
| EGFR-AS1 | - | 0 | 0 | 0 | 0 | 1+ | - | 1+ | 1+ | 1+ |
| Recurrent patient response to Gefitinib | - | Y | - | - | - | - | - | - | - | - |
| PDX response to Gefitinib | - | Y | - | - | N | - | - | - | N | - |

FIG. 12

| Cell Line | Sex/age (yr) | Primary site | Type | Treatment | Outcome |
|---|---|---|---|---|---|
| NCC-HN1 | F/25 | Tongue | Recurrence | Surgery, palliative chemotherapy | Distant metastases, died of disease 5 mo after diagnosis of recurrence |
| NCC-HN43 | M/65 | Tongue | Primary | Surgery, adjuvant chemoradiation therapy | Distant metastases, died of disease 5 mo after initial diagnosis |
| NCC-HN19 | M/48 | Tongue | Primary | Surgery, adjuvant chemoradiation therapy | Distant metastases, died of disease 7 mo after initial diagnosis |
| NCC-HN64 | M/76 | Tongue | Primary | Surgery | Distant metastases, Lost to Follow-up |
| NCC-HN26 | M/60 | Hard palate | Primary | Surgery, adjuvant chemoradiation therapy | Alive 3 yr without disease |
| NCC-HN73 | F/48 | Tongue | Primary | Surgery, adjuvant chemoradiation therapy | Alive 2 yr without disease |

\* All cell lines were established from tumours that were histologically proven to be squamous cell carcinoma and obtained from surgical material derived from lymph node metastases; Abbreviations: F, female; M, male

FIG. 13

| Primary cell line | EGFR Copy no. | EGFR mutation (Sanger sequencing) | | | | | Other mutations (Lung colon Panel) |
|---|---|---|---|---|---|---|---|
| | | Exon 18 G719C G>T G719A G>C G719S G>A | Exon 19 ΔE746-A750 | Exon 19 ΔL747-S752 | Exon 20 2361 G>A Q787Q | Exon 20 T790M C>T | Exon 21 L858R T>G | |
| NCC-HN1 | 7.5 | - | - | - | GG | - | - | ALK, MET, PTEN, TP53 |
| NCC-HN43 | 6.1 | - | - | - | GG | - | - | TP53 |
| NCC-HN19 | 21.4 | - | - | - | AA | - | - | - |
| NCC-HN64 | 5.5 | - | - | - | AA | - | - | ALK, TP53 |
| NCC-HN26 | 5.7 | - | - | - | AG | - | - | TP53 |
| NCC-HN73 | 20.9 | - | - | - | GG | - | - | PIK3CA, TP53 |

SEQUENCE LISTING

<160> NUMBER OF SEQ ID NOS: 33

<210> SEQ ID NO 1
<211> LENGTH: 28
<212> TYPE: DNA
<213> ORGANISM: Artificial sequence
<220> FEATURE:
<223> OTHER INFORMATION: EGFR Exon 18, forward primer

<400> SEQUENCE: 1
ctgaggtgac ccttgtctct gtgttctt                                      28

<210> SEQ ID NO 2
<211> LENGTH: 23
<212> TYPE: DNA
<213> ORGANISM: Artificial sequence
<220> FEATURE:
<223> OTHER INFORMATION: EGFR Exon 18; reverse primer

<400> SEQUENCE: 2
agaggcctgt gccagggacc tta                                           23

<210> SEQ ID NO 3
<211> LENGTH: 20
<212> TYPE: DNA
<213> ORGANISM: Artificial sequence
<220> FEATURE:
<223> OTHER INFORMATION: EGFR Exon 19; forward primer

<400> SEQUENCE: 3
tcactgggca gcatgtggca                                               20

<210> SEQ ID NO 4
<211> LENGTH: 20
<212> TYPE: DNA
<213> ORGANISM: Artificial sequence
<220> FEATURE:
<223> OTHER INFORMATION: EGFR Exon 19; reverse primer

<400> SEQUENCE: 4
cagctgccag acatgagaaa                                        20

<210> SEQ ID NO 5
<211> LENGTH: 19
<212> TYPE: DNA
<213> ORGANISM: Artificial sequence
<220> FEATURE:
<223> OTHER INFORMATION: EGFR Exon 20; forward primer

<400> SEQUENCE: 5
ccatgcgaag ccacactga                                         19

<210> SEQ ID NO 6
<211> LENGTH: 23
<212> TYPE: DNA
<213> ORGANISM: Artificial sequence
<220> FEATURE:
<223> OTHER INFORMATION: EGFR Exon 20; reverse primer

<400> SEQUENCE: 6
cgtatctccc ttccctgatt acc                                    23

<210> SEQ ID NO 7
<211> LENGTH: 21
<212> TYPE: DNA
<213> ORGANISM: Artificial sequence
<220> FEATURE:
<223> OTHER INFORMATION: EGFR Exon 21; forward primer

<400> SEQUENCE: 7
agcagggtct tctctgtttc a                                      21

<210> SEQ ID NO 8
<211> LENGTH: 20
<212> TYPE: DNA
<213> ORGANISM: Artificial sequence
<220> FEATURE:
<223> OTHER INFORMATION: EGFR Exon 21; reverse primer

<400> SEQUENCE: 8
tgacctaaag ccacctcctt                                        20

<210> SEQ ID NO 9
<211> LENGTH: 20
<212> TYPE: DNA
<213> ORGANISM: Artificial sequence
<220> FEATURE:
<223> OTHER INFORMATION: EGFR VIII; forward primer

<400> SEQUENCE: 9
gggctctgga ggaaaagaaa                                        20

<210> SEQ ID NO 10
<211> LENGTH: 22
<212> TYPE: DNA
<213> ORGANISM: Artificial sequence
<220> FEATURE:
<223> OTHER INFORMATION: EGFR VIII; reverse primer

<400> SEQUENCE: 10
attccgttac acactttgcg gc                                     22

<210> SEQ ID NO 11

```
<211> LENGTH: 20
<212> TYPE: DNA
<213> ORGANISM: Artificial sequence
<220> FEATURE:
<223> OTHER INFORMATION: Neo ORF; forward primer

<400> SEQUENCE: 11
ctggctgcta ttgggcgaag                                                    20

<210> SEQ ID NO 12
<211> LENGTH: 20
<212> TYPE: DNA
<213> ORGANISM: Artificial sequence
<220> FEATURE:
<223> OTHER INFORMATION: Neo ORF; reverse primer

<400> SEQUENCE: 12
tgctggagta aaaggggctg                                                    20

<210> SEQ ID NO 13
<211> LENGTH: 21
<212> TYPE: DNA
<213> ORGANISM: Artificial sequence
<220> FEATURE:
<223> OTHER INFORMATION: EGFR Copy; forward primer

<400> SEQUENCE: 13
ccaaggcacg agtaacaagc t                                                  21

<210> SEQ ID NO 14
<211> LENGTH: 20
<212> TYPE: DNA
<213> ORGANISM: Artificial sequence
<220> FEATURE:
<223> OTHER INFORMATION: EGFR Copy; reverse primer

<400> SEQUENCE: 14
gcacataggt aatttccaaa                                                    20

<210> SEQ ID NO 15
<211> LENGTH: 20
<212> TYPE: DNA
<213> ORGANISM: Artificial sequence
<220> FEATURE:
<223> OTHER INFORMATION: Actin (genomic); forward primer

<400> SEQUENCE: 15
gtccccttcc ctcctcagat                                                    20

<210> SEQ ID NO 16
<211> LENGTH: 20
<212> TYPE: DNA
<213> ORGANISM: Artificial sequence
<220> FEATURE:
<223> OTHER INFORMATION: Actin (genomic); reverse primer

<400> SEQUENCE: 16
cggactcgtc atactcctgc                                                    20

<210> SEQ ID NO 17
<211> LENGTH: 20
<212> TYPE: DNA
<213> ORGANISM: Artificial sequence
<220> FEATURE:
<223> OTHER INFORMATION: EGFR Isoform A; forward primer

<400> SEQUENCE: 17
```
actctgagtg catacagtgc                                          20

<210> SEQ ID NO 18
<211> LENGTH: 21
<212> TYPE: DNA
<213> ORGANISM: Artificial sequence
<220> FEATURE:
<223> OTHER INFORMATION: EGFR Isoform A; reverse primer

<400> SEQUENCE: 18
tcgttggaca gccttcaaga c                                        21

<210> SEQ ID NO 19
<211> LENGTH: 20
<212> TYPE: DNA
<213> ORGANISM: Artificial sequence
<220> FEATURE:
<223> OTHER INFORMATION: EGFR Isoform D; forward primer

<400> SEQUENCE: 19
actctgagtg catacagtgc                                          20

<210> SEQ ID NO 20
<211> LENGTH: 20
<212> TYPE: DNA
<213> ORGANISM: Artificial sequence
<220> FEATURE:
<223> OTHER INFORMATION: EGFR Isoform D; reverse primer

<400> SEQUENCE: 20
tgaaggcatg aggctcagtg                                          20

<210> SEQ ID NO 21
<211> LENGTH: 20
<212> TYPE: DNA
<213> ORGANISM: Artificial sequence
<220> FEATURE:
<223> OTHER INFORMATION: Actin (mRNA); forward primer

<400> SEQUENCE: 21
atgtttgaga ccttcacacc                                          20

<210> SEQ ID NO 22
<211> LENGTH: 21
<212> TYPE: DNA
<213> ORGANISM: Artificial sequence
<220> FEATURE:
<223> OTHER INFORMATION: Actin (mRNA); reverse primer

<400> SEQUENCE: 22
aggtagtcag tcaggtcccg g                                        21

<210> SEQ ID NO 23
<211> LENGTH: 20
<212> TYPE: DNA
<213> ORGANISM: Artificial sequence
<220> FEATURE:
<223> OTHER INFORMATION: EGFR AS1; forward primer

<400> SEQUENCE: 23
tccaggtgaa gacgcatgaa                                          20

<210> SEQ ID NO 24
<211> LENGTH: 20
<212> TYPE: DNA

```
<213> ORGANISM: Artificial sequence
<220> FEATURE:
<223> OTHER INFORMATION: EGFR AS1; reverse primer

<400> SEQUENCE: 24
gtcttttgca ggcacagctt                                              20

<210> SEQ ID NO 25
<211> LENGTH: 15
<212> TYPE: DNA
<213> ORGANISM: Artificial sequence
<220> FEATURE:
<223> OTHER INFORMATION: LNA against EGFR-AS1 (LNA-AS1)

<400> SEQUENCE: 25
atcgcaaagg taatc                                                   15

<210> SEQ ID NO 26
<211> LENGTH: 15
<212> TYPE: DNA
<213> ORGANISM: Artificial sequence
<220> FEATURE:
<223> OTHER INFORMATION: Negative control (LNA-i-miR-NC)

<400> SEQUENCE: 26
aacacgtcta tacgc                                                   15

<210> SEQ ID NO 27
<211> LENGTH: 6369
<212> TYPE: DNA
<213> ORGANISM: Artificial sequence
<220> FEATURE:
<223> OTHER INFORMATION: EGFR as shown in NCBI sequence ID: NM_005228.4

<400> SEQUENCE: 27
gtccgggcag cccccggcgc agcgcggccg cagcagcctc cgccccccgc acgtgtgag    60 cgcccgacgc ggcccgaggcg gccggagtcc cgagctagcc ccggcggccg ccgccgcca   120 gaccggacga caggccacct cgtcggcgtc cgcccgagtc cccgcctcgc cgccaacgcc   180
acaaccaccg cgcacggccc cctgactccg tccagtattg atcgggagag ccggagcgag   240
ctcttcgggg agcagcgatg cgaccctccg ggacggccgg ggcagcgctc ctggcgctgc   300
tggctgcgct ctgcccggcg agtcgggctc tggaggaaaa gaaagtttgc caaggcacga   360
gtaacaagct cacgcagttg ggcacttttg aagatcattt tctcagcctc cagaggatgt   420
tcaataactg tgaggtggtc cttgggaatt tggaaattac ctatgtgcag aggaattatg   480
atctttcctt cttaaagacc atccaggagg tggctggtta tgtcctcatt gccctcaaca   540
cagtggagcg aattcctttg gaaaacctgc agatcatcag aggaaatatg tactacgaaa   600
attcctatgc cttagcagtc ttatctaact atgatgcaaa taaaaccgga ctgaaggagc   660
tgcccatgag aaatttacag gaaatcctgc atggcgccgt gcggttcagc aacaaccctg   720
ccctgtgcaa cgtggagagc atccagtggc gggacatagt cagcagtgac tttctcagca   780
acatgtcgat ggacttccag aaccacctgg gcagctgcca aaagtgtgat ccaagctgtc   840
ccaatgggag ctgctggggt gcaggagagg agaactgcca gaaactgacc aaaatcatct   900
gtgcccagca gtgctccggg cgctgccgtg gcaagtcccc cagtgactgc tgccacaacc   960
agtgtgctgc aggctgcaca ggccccggg agagcgactg cctggtctgc cgcaaattcc    1020
gagacgaagc cacgtgcaag gacacctgcc cccactcat gctctacaac cccaccacgt    1080
accagatgga tgtgaacccc gagggcaaat acagctttgg tgccacctgc gtgaagaagt    1140
```

```
gtccccgtaa ttatgtggtg acagatcacg gctcgtgcgt ccgagcctgt ggggccgaca    1200
gctatgagat ggaggaagac ggcgtccgca agtgtaagaa gtgcgaaggg ccttgccgca    1260
aagtgtgtaa cggaataggt attggtgaat ttaaagactc actctccata aatgctacga    1320
atattaaaca cttcaaaaac tgcacctcca tcagtgcga tctccacatc ctgccggtgg     1380
catttagggg tgactccttc acacatactc ctcctctgga tccacaggaa ctggatattc    1440
tgaaaaccgt aaaggaaatc acagggtttt tgctgattca ggcttggcct gaaaacagga    1500
cggacctcca tgcctttgag aacctagaaa tcatacgcgg caggaccaag caacatggtc    1560
agttttctct tgcagtcgtc agcctgaaca taacatcctt gggattacgc tccctcaagg    1620
agataagtga tggagatgtg ataatttcag gaaacaaaaa tttgtgctat gcaaatacaa    1680
taaactggaa aaaactgttt gggacctccg gtcagaaaac caaaattata agcaacagag    1740
gtgaaaacag ctgcaaggcc acaggccagg tctgccatgc cttgtgctcc cccgagggct    1800 gctgggccc ggagcccagg gactgcgtct cttgccggaa tgtcagccga ggcagggaat     1860
gcgtggacaa gtgcaaccttc tggagggtg agccaaggga gtttgtggag aactctgagt    1920
gcatacagtg ccacccagag tgcctgcctc aggccatgaa catcacctgc acaggacggg    1980
gaccagacaa ctgtatccag tgtgcccact acattgacgg cccccactgc gtcaagacct    2040
gcccggcagg agtcatggga gaaaacaaca ccctggtctg gaagtacgca gacgccggcc    2100
atgtgtgcca cctgtgccat ccaaactgca cctacggatg cactgggcca ggtcttgaag    2160
gctgtccaac gaatgggcct aagatcccgt ccatcgccac tgggatggtg ggggccctcc    2220
tcttgctgct ggtggtggcc ctggggatcg gcctcttcat gcgaaggcgc cacatcgttc    2280
ggaagcgcac gctgcggagg ctgctgcagg agagggagct tgtggagcct cttacaccca    2340
gtggagaagc tcccaaccaa gctctcttga ggatcttgaa ggaaactgaa ttcaaaaaga    2400
tcaaagtgct gggctccggt gcgttcggca cggtgtataa gggactctgg atcccagaag    2460
gtgagaaagt taaaattccc gtcgctatca aggaattaag agaagcaaca tctccgaaag    2520
ccaacaagga aatcctcgat gaagcctacg tgatggccag cgtggacaac ccccacgtgt    2580
gccgcctgct gggcatctgc ctcacctcca ccgtgcagct catcacgcag ctcatgccct    2640
tcggctgcct cctggactat gtccgggaac acaaagacaa tattggctcc cagtacctgc    2700
tcaactggtg tgtgcagatc gcaaagggca tgaactactt ggaggaccgt cgcttggtgc    2760
accgcgacct ggcagccagg aacgtactgg tgaaaacacc gcagcatgtc aagatcacag    2820
attttgggct ggccaaactg ctgggtgcgg aagagaaaga ataccatgca gaaggaggca    2880
aagtgcctat caagtggatg gcattggaat caatttttaca cagaatctat acccaccaga    2940
gtgatgtctg gagctacggg gtgactgttt gggagttgat gacctttgga tccaagccat    3000
atgacggaat ccctgccagc gagatctcct ccatcctgga gaaggagaa cgcctccctc     3060 agccacccat atgtaccatc gatgtctaca tgatcatggt caagtgctgg atgatagacg    3120
cagatagtcg cccaaagttc cgtgagttga tcatcgaatt ctccaaaatg gcccgagacc    3180
cccagcgcta ccttgtcatt caggggatg aaagaatgca tttgccaagt cctacagact     3240
ccaacttcta ccgtgccctg atggatgaag aagacatgga cgacgtggtg gatgccgacg    3300
agtacctcat cccacagcag ggcttcttca gcagcccctc cacgtcacgg actcccctcc    3360
tgagctctct gagtgcaacc agcaacaatt ccaccgtggc ttgcattgat agaaatgggc    3420
tgcaaagctg tcccatcaag gaagacagct tcttgcagcg atacagctca gaccccacag    3480
```

```
gcgccttgac tgaggacagc atagacgaca ccttcctccc agtgcctgaa tacataaacc    3540
agtccgttcc caaaaggccc gctggctctg tgcagaatcc tgtctatcac aatcagcctc    3600
tgaaccccgc gcccagcaga gacccacact accaggaccc ccacagcact gcagtgggca    3660
accccgagta tctcaacact gtccagccca cctgtgtcaa cagcacattc gacagccctg    3720
cccactgggc ccagaaaggc agccaccaaa ttagcctgga caaccctgac taccagcagg    3780
acttcttttcc caaggaagcc aagccaaatg gcatctttaa gggctccaca gctgaaaatg    3840
cagaatacct aagggtcgcg ccacaaagca gtgaatttat tggagcatga ccacggagga    3900
tagtatgagc cctaaaaatc cagactcttt cgatacccag gaccaagcca cagcaggtcc    3960
tccatcccaa cagccatgcc cgcattagct cttagaccca cagactggtt ttgcaacgtt    4020
tacaccgact agccaggaag tacttccacc tcgggcacat tttgggaagt tgcattcctt    4080
tgtcttcaaa ctgtgaagca tttacagaaa cgcatccagc aagaatattg tccctttgag    4140
cagaaattta tctttcaaag aggtatattt gaaaaaaaaa aaagtatat gtgaggattt    4200
ttattgattg gggatcttgg agttttttcat tgtcgctatt gattttttact tcaatgggct    4260
cttccaacaa ggaagaagct tgctggtagc acttgctacc ctgagttcat ccaggcccaa    4320
ctgtgagcaa ggagcacaag ccacaagtct tccagaggat gcttgattcc agtggttctg    4380
cttcaaggct tccactgcaa aacactaaag atccaagaag gccttcatgg ccccagcagg    4440
ccggatcggt actgtatcaa gtcatggcag gtacagtagg ataagccact ctgtcccttc    4500
ctgggcaaag aagaaacgga ggggatggaa ttcttcctta gacttacttt tgtaaaaatg    4560
tccccacggt acttactccc cactgatgga ccagtggttt ccagtcatga gcgttagact    4620
gacttgtttg tcttccattc cattgttttg aaactcagta tgctgcccct gtcttgctgt    4680
catgaaatca gcaagagagg atgacacatc aaataataac tcggattcca gcccacattg    4740
gattcatcag catttggacc aatagcccac agctgagaat gtggaatacc taaggatagc    4800
accgcttttg ttctcgcaaa aacgtatctc ctaatttgag gctcagatga aatgcatcag    4860
gtcctttggg gcatagatca gaagactaca aaaatgaagc tgctctgaaa tctcctttag    4920
ccatcacccc aaccccccaa aattagtttg tgttacttat ggaagatagt tttctccttt    4980
tacttcactt caaaagcttt ttactcaaag agtatatgtt ccctccaggt cagctgcccc    5040
caaacccccct cctacgcctt tgtcacacaa aaagtgtctc tgccttgagt catctattca    5100
agcacttaca gctctggcca caacagggca ttttacaggt gcgaatgaca gtagcattat    5160
gagtagtgtg gaattcaggt agtaaatatg aaactagggt ttgaaattga taatgctttc    5220
acaacatttg cagatgtttt agaaggaaaa aagttccttc ctaaaataat ttctctacaa    5280
ttggaagatt ggaagattca gctagttagg agcccacctt ttttcctaat ctgtgtgtgc    5340
cctgtaacct gactggttaa cagcagtcct ttgtaaacag tgttttaaac tctcctagtc    5400
aatatccacc ccatccaatt tatcaaggaa gaaatggttc agaaaatatt ttcagcctac    5460
agttatgttc agtcacacac acatacaaaa tgttcctttt gcttttaaag taattttga     5520
ctcccagatc agtcagagcc cctacagcat tgttaagaaa gtatttgatt tttgtctcaa    5580
tgaaaataaa actatattca tttccactct attatgctct caaatacccc taagcatcta    5640
tactagcctg gtatgggtat gaaagataca aagataaata aacatagtc cctgattcta    5700
agaaattcac aatttagcaa aggaaatgga ctcatagatg ctaaccttaa aacaacgtga    5760
caaatgccag acaggaccca tcagccaggc actgtgagag cacagagcag ggaggttggg    5820
tcctgcctga ggagacctgg aagggaggcc tcacaggagg atgaccaggt ctcagtcagc    5880
```

```
ggggaggtgg aaagtgcagg tgcatcaggg gcaccctgac cgaggaaaca gctgccagag    5940
gcctccactg ctaaagtcca cataaggctg aggtcagtca ccctaaacaa cctgctccct    6000
ctaagccagg ggatgagctt ggagcatccc acaagttccc taaaagttgc agccccagg    6060 gggattttga gctatcatct ctgcacatgc ttagtgagaa gactcacaa catttctaag    6120 aatctgagat tttatattgt cagttaacca ctttcattat tcattaccct caggacatgc    6180
agaaatattt cagtcagaac tgggaaacag aaggacctac attctgctgt cacttatgtg    6240
tcaagaagca gatgatcgat gaggcaggtc agttgtaagt gagtcacatt gtagcattaa    6300
attctagtat ttttgtagtt tgaaacagta acttaataaa agagcaaaag ctaaaaaaaa    6360
aaaaaaaaa                                                            6369
```

<210> SEQ ID NO 28
<211> LENGTH: 12
<212> TYPE: DNA
<213> ORGANISM: Artificial sequence
<220> FEATURE:
<223> OTHER INFORMATION: NCC-HN1 (GG) sequence as shown in Fig. 1B

<400> SEQUENCE: 28
gtgcagctca tc                                                          12

<210> SEQ ID NO 29
<211> LENGTH: 12
<212> TYPE: DNA
<213> ORGANISM: Artificial sequence
<220> FEATURE:
<223> OTHER INFORMATION: NCC-HN43 (GG) sequence as shown in Fig. 1B

<400> SEQUENCE: 29
gtgcagctca tc                                                          12

<210> SEQ ID NO 30
<211> LENGTH: 12
<212> TYPE: DNA
<213> ORGANISM: Artificial sequence
<220> FEATURE:
<223> OTHER INFORMATION: NCC-HN73 (GG) sequence as shown in Fig. 1B

<400> SEQUENCE: 30
gtgcagctca tc                                                          12

<210> SEQ ID NO 31
<211> LENGTH: 12
<212> TYPE: DNA
<213> ORGANISM: Artificial sequence
<220> FEATURE:
<223> OTHER INFORMATION: NCC-HN26 (GA) sequence as shown in Fig. 1B

<400> SEQUENCE: 31
gtgcaactca tc                                                          12

<210> SEQ ID NO 32
<211> LENGTH: 12
<212> TYPE: DNA
<213> ORGANISM: Artificial sequence
<220> FEATURE:
<223> OTHER INFORMATION: NCC-HN19 (AA) sequence as shown in Fig. 1B

<400> SEQUENCE: 32
gtgcaactca tc                                                          12

```
<210> SEQ ID NO 33
<211> LENGTH: 12
<212> TYPE: DNA
<213> ORGANISM: Artificial sequence
<220> FEATURE:
<223> OTHER INFORMATION: NCC-HN64 (AA) sequence as shown in Fig. 1B

<400> SEQUENCE: 33
gtgcaactca tc                                                           12
```

USE OF BIOMARKERS IN DETERMINING SUSCEPTIBILITY TO DISEASE TREATMENT

CROSS-REFERENCE TO RELATED APPLICATIONS

This application is a national stage entry under 35 USC § 371 of PCT International Application Number PCT/SG2017/050284, filed Jun. 5, 2017, which claims the benefit of priority of U.S. provisional application No. 62/345,081, filed 3 Jun. 2016, the entire disclosures of both of which are expressly incorporated by reference herein.

FIELD OF THE INVENTION

The present invention relates generally to the field of molecular biology. In particular, the present invention relates to the use of biomarkers for determining treatment modalities for various diseases, such as cancer.

BACKGROUND OF THE INVENTION

Pathway-directed therapeutics, for example those targeting the epidermal growth factor receptor (EGFR)-related pathways, have established clinical activity in various types, of cancer, for example, head and neck squamous cell cancers (HNSCC). It is noted that site-specific differences in treatment outcomes have been observed.

Although there have been significant improvements in multimodality approaches to the treatment of cancer, these so far appear to have a full remission rate of only 50%, that is to say only 50% of the cancers are cured. To date, the standard of care provides limited options for the treatment of recurrent, metastatic disease, for example with platinum-based chemotherapy which are known to confer a median overall survival of 6 to 9 months. Despite evidence that a large subset of, for example, HNSCC cancers are dependent on EGFR-signalling, so far only moderate success has been achieved with known treatments based on monoclonal antibodies and/or tyrosine kinase inhibitors (TKI). For example, in the metastatic setting, cetuximab monotherapy is associated with response rates of 13%, while efficacy of epidermal growth factor receptor (EGFR) tyrosine kinase inhibitors across several phase II trials are more heterogeneous, with response rates ranging from 1.8-20%.

Thus, there is a need for biomarkers, genetic, protein or otherwise, that are capable of predicting a subjects susceptibility to a specific drug treatment.

SUMMARY

In one aspect, the present invention refers to a method of predicting susceptibility of a subject suffering from cancer to a treatment with an anti-cancer drug, wherein the method comprises detecting the presence or absence of a genetic alteration in long non-coding RNA (lncRNA) that resides in an antisense strand of an oncogene, wherein the genetic alteration alters or disrupts expression of the oncogene; wherein in case the genetic alteration is present, the subject is predicted to show improved susceptibility to the treatment with the anti-cancer drug compared to a subject not carrying the mutation.

In another aspect, the present invention refers to a method of predicting the susceptibility of a subject suffering from cancer related to EGFR to a treatment with an EGFR inhibitor, the method comprising determining whether either one or two or all of the following is given: i) the subject has a silent G>A mutation (genetic alteration) at Q787Q position in exon 20 of EGFR (nucleotide 2361; as shown in NCBI sequence ID: NM_005228.4 and SEQ ID NO: 27); ii) the subject has lower EGFR-AS1 or EGFR-AS1 lncRNA expression level compared to subject that does not respond to treatment with an EGFR inhibitor; iii) the subject has higher EGFR isoform D/isoform A ratio compared to subject that does not respond to treatment with an EGFR inhibitor; wherein in case one or two or all of i) to iii) is given the subject is predicted to show improved susceptibility to a treatment with an EGFR inhibitor compared to a subject not showing any of i) to iii).

In yet another aspect, the present invention refers to a method of treating cancer in a subject suffering from said cancer, wherein the method comprises detecting the presence or absence of a mutation in a long non-coding RNA on an antisense strand of an oncogene related to the cancer, wherein the genetic alteration alters or disrupts expression of the oncogene; administering an anti-cancer drug for the cancer type the subject suffers from in case the presence of the genetic alteration is confirmed.

In a further aspect, the present invention refers to a method of treating a subject suffering from cancer, comprising administering to the subject an effective amount of a therapeutic agent affecting expression of a non-coding RNA an oncogene, wherein the genetic alteration alters or disrupts expression of the oncogene; and administering to the subject an effective amount of an anti-cancer drug specific for the cancer related to the oncogene.

In one aspect, the present invention refers to a method of treating a subject suffering from an EGFR-related cancer, comprising administering to the subject an effective amount of a therapeutic agent affecting EGFR-AS1 lncRNA expression, or affecting EGFR-AS1 expression, or increasing the amount of EGFR isoform D and/or decreasing EGFR isoform A or a combination thereof; and administering to the subject an effective amount of a tyrosine kinase inhibitor used to treat the EGFR-related cancer.

BRIEF DESCRIPTION OF THE DRAWINGS

The invention will be better understood with reference to the detailed description when considered in conjunction with the non-limiting examples and the accompanying drawings, in which:

FIG. 1 is a collection of FIG. 1A-FIG. 1E showing the correlation of a point mutation in a lncRNA of EGFR, referred to herein as Q787Q, with sensitivity of primary HNSCC cell lines to EGFR tyrosine kinase inhibitors.

FIG. 2 is a collection of FIG. 2A-FIG. 2E showing the implication of the long non-coding RNA EGFR-AS1 as the mechanism for EGFR tyrosine kinase inhibitors sensitivity.

FIG. 3 is a collection of FIG. 3A-FIG. 3F showing effect of EGFR-AS1 long non-coding RNA on EGFR isoforms and sensitivity to tyrosine kinase inhibitors (TKI).

FIG. 4 is a collection of FIG. 4A-FIG. 4D showing in vivo correlation of Q787Q genotype with EGFR-AS1 and EGFR isoform transcript and response to gefitinib treatment. FIG. 4B is a table showing correlation between Q787Q genotype, relative transcript levels of AS1 and isoform D/A ratio (by real-time RT-PCR), along with the formalin-fixed paraffin embedded (FFPE) tissue score (RNA-scope scoring) and $IC_{50}$ levels for a panel of patient derived tumour tissue and cell lines, thereby summarising the information provided in previous figures.

FIG. 12 is a table showing clinico-pathologic characteristics of patients from which cell lines were derived.

FIG. 13 is a table showing mutational status of EGFR in the cell lines NCC-HN1, NCC-HN43, NCC-HN19, NCC-HN64, NCC-HN26, and NCC-HN73.

DEFINITION OF TERMS

Figure 1A:
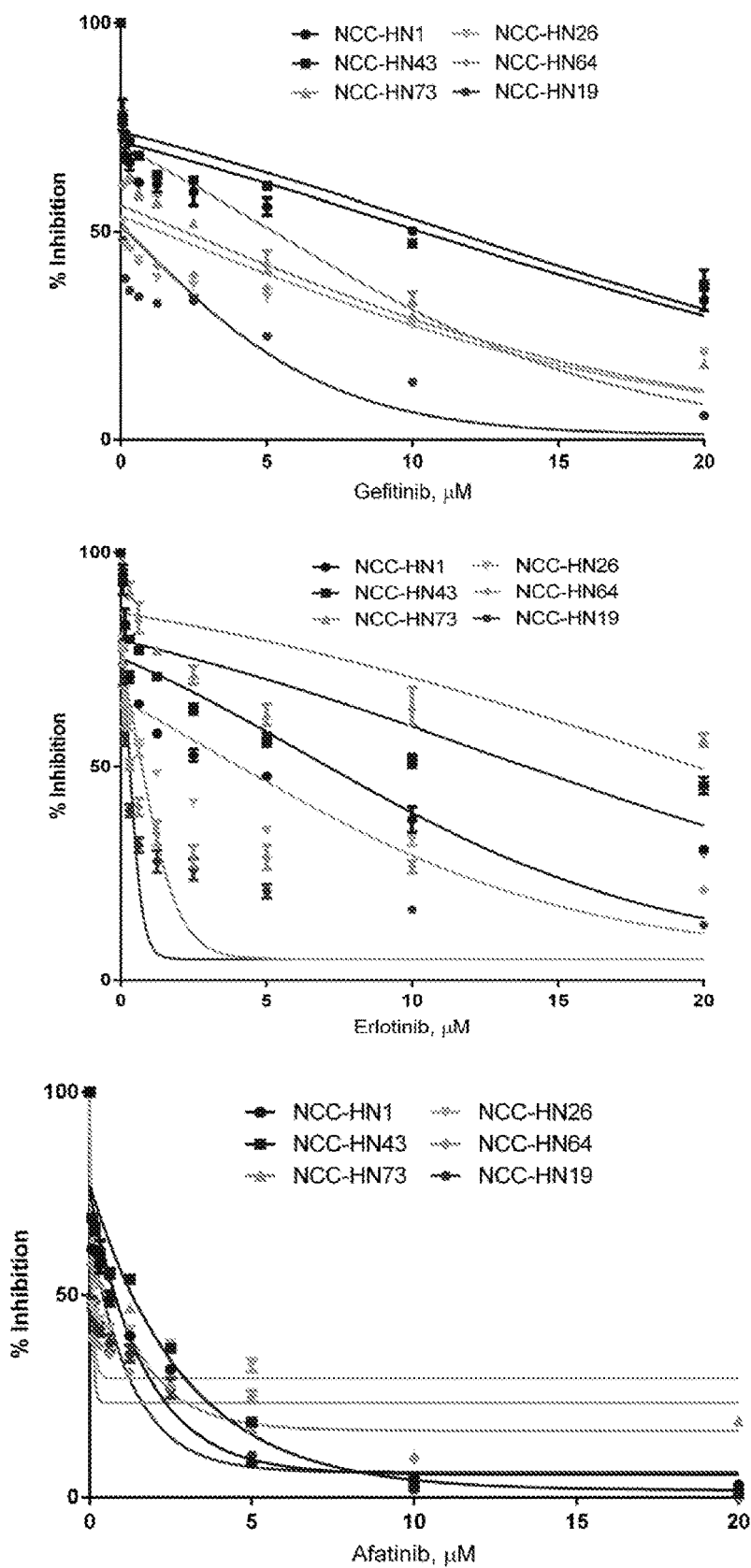
FIG. 1A is a set of line graphs showing the result of a cell proliferation assays and the effect of a treatment with gefitinib, erlotinib or afatinib on the inhibition of cell proliferation. Error bars indicate one standard deviation.

The term "genotype switching" refers to a genetic recombination event (also termed a "knock-in") where a nucleotide at a given position is switched with another nucleotide, thereby changing the genotype of the subject from one genotype to another. For example, in the experiments has shown herein, the nucleotide residue for position Q787Q at position 2361 on the EGFR gene (as shown in NCBI sequence ID: NM_005228.4) has been switched from a G to an A.

The term "tyrosine kinase" refers to an enzyme that can transfer a phosphate group from adenosine triphosphate (ATP) to a target protein in a cell. It functions as an "on" or "off" switch in many cellular functions. Tyrosine kinases are a subclass of protein kinase, of which the tyrosine kinase is named as such because it transfers the phosphate group from ATP to a tyrosine residue within the target protein. There are two known families of tyrosine kinase, namely receptor tyrosine kinase (RTK) and non-receptor or cytoplasmic tyrosine kinase, whereby receptor tyrosine kinases comprise a transmembrane domain and one or more extracellular ligand-binding domains. Cytoplasmic tyrosine kinases do not possess such a transmembrane domain or any extracellular ligand-binding domains.

The term "oncogene" refers to a gene that has the potential to cause cancer. An oncogene can also refer to a dominant mutant allele of a cellular gene (a proto-oncogene) that disrupts cell growth and division and is capable of transforming a normal cell into a cancerous cell. In tumour cells, oncogenes are often mutated or expressed at high levels. Proto-oncogenes typically encode proteins involved in, but not limited to, positive control of the cell division cycle, such as, for example, growth factor receptors, signal transduction proteins and transcription factors. Mutations in these genes tend to relax control mechanisms and accelerate cell division, leading to the cell proliferation that is characteristic of cancer. Some oncogenic mutations cause inhibition of programmed cell death (apoptosis), so that cancerous cells are less likely to be destroyed by the host s immune system. Most normal cells will undergo apoptosis when critical functions are altered. Instead, activated oncogenes can cause those cells designated for apoptosis to proliferate and survive. Some oncogenes can require an additional step, for example, such as mutations in another gene, or environmental factors, such as viral infection, to cause cancer.

The term "RNA", that is "ribonucleic acid" refers to an organic molecule consisting of along chain of nucleotides in which the sugar is ribose (or variations thereof) and the bases are adenine, cytosine, guanine, and uracil. There are various types of RNA, for example, but not limited to, messenger RNA (mRNA), transfer RNA (tRNA), ribosomal RNA (rRNA), transfer-messenger RNA (tmRNA), small nuclear RNA (snRNA), antisense RNA (asRNA) and Piwi-interacting RNA (piRNA). All types of RNA are either coding or non-coding, that is the RNA either results in expression of a protein (for example, messenger RNA) or it does not (for example, transfer RNA). A particular example of non-coding RNA is long, non-coding RNA (lncRNA), which refers to non-coding RNA transcripts of 200 nucleotides or longer in length (at least 200 nucleotides). LncRNA are transcripts that range from 200 nucleotides to 100 000 nucleotides (or 200 bases to 100 kb), and distributed are throughout the genome. In some example, the lncRNAs are between 200 nucleotides to 100000 nucleotides, between 200 to 400 nucleotides, between 300 to 700 nucleotides, between 500 to 1000 nucleotides, between 900 to 1300 nucleotides, between 1200 to 2500 nucleotides, between 2400 to 3600 nucleotides, between 3500 to 4800 nucleotides, between 4500 to 10 000 nucleotides, between 9000 and 50000 nucleotides, between 50000 to 75000 nucleotides, between 70000 to 100000 nucleotides in length. In another example, the lncRNAs are at least 200 nucleotides, at least 250 nucleotides, at least 280 nucleotides, at least 320 nucleotides, at least 480 nucleotides, at least 520 nucleotides, at least 550 nucleotides, at least 640 nucleotides, at least 760 nucleotides, at least 830 nucleotides, at least 950 nucleotides, at least 1100 nucleotides, at least 1250 nucleotides, at least 1400 nucleotides, at least 1600 nucleotides, at least 1800 nucleotides, at least 2100 nucleotides, at least 2800 nucleotides, at least 5500 nucleotides, at least 10500 nucleotides, at least 25000 nucleotides, at least 35000 nucleotides, at least 48000 nucleotides, at least 55000 nucleotides, at least 68000 nucleotides, at least 80000 nucleotides in length. Although having little or no known protein-coding capability, they have diverse functions including transcriptional regulation, epigenetic modulation through chromatin modification, and post-transcriptional regulation. Several of these functions relate to direct (homology-based) binding to DNA, pre-mRNA and mature mRNA. However, it is believed that the three-dimensional structural conformation of lncRNAs plays an important role in extending their wide ranging repertoire and also influences stability of these molecules themselves.

The term "RNAi" refers to RNA interference, a process in which RNA molecules inhibit gene function. This interference is based on the ability of double-stranded RNA to interfere with, or suppress, the expression of a gene with a corresponding base sequence. For example, two types of small ribonucleic acid (RNA) molecules—microRNA (miRNA) and small interfering RNA (siRNA)—are important to RNA interference. RNA molecules (or RNAs) are the direct products of genes, and these small RNAs can bind, for example, to other specific messenger RNA (mRNA) molecules, thereby either increase or decrease their activity, for example by preventing an mRNA from producing a protein. RNA interference plays an important role in development and in defending cells against parasitic nucleotide sequences from, for example, viruses and transposons.

The term "sense strand", also known as a coding strand, refers to a segment within double-stranded DNA that runs from 5' to 3', and which is complementary to the antisense strand of DNA, which runs from 3' to 5'. The sense strand is the strand of DNA that has the same sequence as the mRNA, which takes the antisense strand as its template during transcription, and eventually (albeit typically, not always) undergoes translation into a protein. The antisense strand is thus responsible for the RNA that is later translated to protein, while the sense strand possesses a nearly identical makeup to that of the mRNA. It is noted that for each segment of double-stranded DNA (dsDNA), there will possibly be two sets of sense and antisense, depending on which direction one reads the DNA, since the naming of sense and antisense is relative to perspective. It is ultimately the gene product, or mRNA, that dictates which strand of one segment of dsDNA is called sense or antisense. However, it is noted that, for example in prokaryotes, overlapping genes on opposite strands means the sense for one mRNA can be the antisense for another mRNA. In the context of the present invention, the antisense strand obtained from the DNA refers to the RNA segment running in 3' to 5' direction.

The term "mutation" or "mutated" or "genetic alteration" refers to a natural or artificial modification, or genetic alteration of the genome or part of a nucleic acid sequence of any biological organism, virus or extra-chromosomal genetic element. This mutation can be induced artificially using, but not limited to, chemicals and radiation, but can also occur spontaneously during nucleic acid replication in cell division. Mutations may or may not produce discernible changes in the observable characteristics (phenotype) of an organism. There are various types of mutations known, which can either be small-scale mutations or large-scale mutations. Examples of small-scale mutations are, but are not limited to, substitution mutations, silent mutations, missense mutations, nonsense mutations, insertions, and deletions. Examples of large-scale mutations are, but are not limited to, amplifications, deletions, chromosomal translocations, interstitial deletions, chromosomal inversions and mutations that result in a loss of heterozygosity. Mutations can also be grouped by their effect on the function of the resulting product. These include, but are not limited to, loss-of-function (inactivating) mutations, gain-of-function (activating) mutations, dominant-negative (antimorphic) mutations, lethal mutations and back or reverse mutations. Point mutations, for example, also known as single base modification, are a type of mutation that causes a single nucleotide base substitution, insertion, or deletion of the genetic material, DNA or RNA. The term "frame-shift mutation" indicates the addition or deletion of a base pair.

For example, silent mutations are mutations in DNA that do not significantly alter the phenotype of the organism in which they occur. Silent mutations can occur in non-coding regions (outside of genes or within introns), or they may occur within exons. When they occur within exons, they either do not result in a change to the amino acid sequence of a protein (also known as a synonymous substitution), or they result in the insertion of an alternative amino acid with similar properties to that of the original amino acid. In either case, there is no significant change in the resulting phenotype. The phrase silent mutation is often used interchangeably with the phrase synonymous mutation. However, synonymous mutations only occur within exons, and are not always silent mutations. Synonymous mutations are mutations that can affect transcription, splicing, mRNA transport, and translation, any of which could alter phenotype, rendering the synonymous mutation non-silent.

The term "polymorphism" refers to the existence of two or more distinctly different forms (morphs) within, for example an animal species. In genetics, a (genetic) polymorphism is used to describe essentially inter-individual, functionally silent differences in DNA sequence that make each human genome unique. In other words, a genetic polymorphism is the occurrence, in the same population, of multiple discrete allelic states, of which at least two have high frequency. Conventionally, the high frequency is defined as being of 1% or more of the population in question. One example of a genetic polymorphism is a single nucleotide polymorphism (SNP), which is a variation in a single nucleotide that occurs at a specific position in the genome, where each variation is present to some appreciable degree within a population (for example, more than 1% of said population).

The term "susceptibility" refers to the propensity of something, for example a disease, to be likely affected by something else, for example, a treatment for said disease. This effect can be either positive or negative, depending on what is being referenced. For example, if a disease is sensitive to a particular treatment, then the susceptibility of said disease to a particular treatment is a positive effect. It can then be said that the disease is susceptible (or sensitive) to the treatment. On the other hand, if a disease is not susceptible to a given treatment, the disease is then considered to be unresponsive or resistant to said treatment.

As defined above, the term "predicting susceptibility" refers to the propensity of something, for example a disease, to be likely affected by something else, for example, a treatment for said disease. In other words, to predict susceptibility of a cancer to a particular treatment is to determine whether the cancer would react to a treatment with a certain medicament or anti-cancer drug. It is of note that the term "determining susceptibility" is not synonymous with, for example, "making a prognosis". The former term only looks at the possible reaction of a disease to a specific drug or therapy, while the latter describes the likelihood of the patient to survive the disease or disease progression as a whole. While, in some cases, it may be possible to correlate the effect of one term on the other, that is to say that a disease reacting well to a given treatment (that is, the disease is susceptible to the treatment) may increase the likelihood of said patient receiving a positive prognosis in regards to the overall disease progression, this is not to be taken as a rule. As a person skilled in the art would appreciate, a positive prognosis depends on many factors patient-specific factors in addition to the disease's susceptibility for treatment, for example, overall wellbeing of the patient prior to treatment, metabolism, diet, aggressiveness of the (primary) disease, secondary diseases and/or infections and the like. The term "expression" refers to either gene expression, that is the transcription of DNA into messenger RNA (mRNA) by the RNA polymerase, or protein expression, which is the translation of mRNA into a (functional) protein. An expression may be considered up-regulated (or over-expression) or down-regulated (suppression, low or decreased expression, also termed under-expression), depending on whether an increase or decrease in expression is present, usually compared to a wild-type or a disease-free subject.

The term "isoform" or "protein isoform" refers to the different forms of a protein encoded from one and the same gene. These proteins are different in both structure and composition, whereby these differences are regulated by alternative splicing of mRNA. This alternative splicing has been shown to have a large impact in proteome diversity. The specificity of produced proteins is derived by protein structure/function, development stage and even the cell type. Isoform formation becomes more complicated when a protein has multiple subunits and each subunit has multiple isoforms.

The term "alternative splicing" refers to a regulated process during gene expression that results in a single gene coding for multiple proteins. In this process, particular exons (that is, parts of the genetic code that become part of the mature RNA) of a gene may be included within or excluded from the final, processed messenger RNA (mRNA) produced from that gene. The excluded sequences are termed introns, from intragenic region, that is a region inside a gene. The term intron and exon refers to both the DNA sequence within a gene and the corresponding sequence in RNA transcripts Consequently, the proteins translated from alternatively spliced mRNAs will contain differences in their amino acid sequence and, often, in their biological functions.

The term "therapeutic agent" refers to a chemical compound or composition capable of inducing a desired therapeutic effect when properly administered to a patient. For example, an anti-diabetic agent is considered a therapeutic agent, in the sense that it is administered to treat, for example, diabetes in a patient.

The term "locked nucleic acid", "LNA" or "inaccessible RNA", refers to a modified RNA nucleotide, in which the ribose moiety of an LNA nucleotide is modified with an extra bridge connecting the 2' oxygen and 4' carbon. The bridge "locks" the ribose in the 3'-endo (North) conformation, which is the same confirmation often found in the A-form duplexes. The, usually synthetic, locked nucleic acid nucleotides can be mixed with DNA or RNA residues in the oligonucleotide, whenever desired, and hybridize with DNA or RNA according to Watson-Crick base-pairing rules. The locked ribose conformation enhances base stacking and backbone pre-organization. This significantly increases the hybridization properties (melting temperature) of oligonucleotides.

The term "EGFR inhibitor" refers to compounds that are capable of inhibiting or blocking the activity of epidermal growth factor receptors. Various compounds and drugs are not limited to a single effect and can therefore be considered to be EGFR inhibitors, even if they are structurally different. That is to say, the inhibition of EGFR is the combining characteristic of these compounds.

The term "EGFR-AS1" refers to a 2.8 kb sequence that corresponds to intron and exon 20 (FIG. 2A) expressed by the EGFR gene.

As used herein, the term "haematological malignancy" or "haematological malignancies" refers to usually malignant neoplasms or cancers which are derived from blood-forming tissue, such as the bone marrow, or in the cells of the immune system. These cancers are also known in the art as blood cancers, or liquid cancers. Haematological malignancies may derive from either of the two major blood cell lineages: myeloid and lymphoid cell lines. The myeloid cell line normally produces granulocytes, erythrocytes, thrombocytes, macrophages and mast cells; the lymphoid cell line produces B, T, NK (natural killer cells) and plasma cells. Lymphomas, lymphocytic leukaemia, and myeloma are derived from the lymphoid line, while acute and chronic myelogenous leukaemia, myelodysplastic syndromes and myeloproliferative diseases are considered to be myeloid in origin. Examples of hematologic cancer are, but are not limited to, leukaemia, lymphoma, and multiple myeloma. Types of leukaemia are, but are not limited to, acute lymphoblastic leukaemia (ALL), acute myelogenous leukaemia (AML), chronic lymphocytic leukaemia (CLL), chronic myelogenous leukaemia (CML), and acute monocytic leukaemia (AMoL). Types of lymphomas are, but are not limited to, Hodgkin's lymphomas, which includes all four subtypes of Hodgkin's lymphomas; and all subtypes of Non-Hodgkin's lymphomas.

DETAILED DESCRIPTION OF THE PRESENT INVENTION

The success of targeted therapeutics is predicated based on high-precision predictive biomarkers. For example, cohort-based sequencing studies have failed to demonstrate activating mutations in exons 18 to 21 of epidermal growth factor receptor (EGFR), or demonstrate the presence of known predictors of (treatment) response, for example, EGFR amplifications, thereby highlighting a subset of tumours that remain EGFR-driven through non-genomic mechanisms. For example, in a completed phase II trial that examined the impact of induction gefitinib prior to chemoradiotherapy for unresectable oral squamous cell cancer, two patients who responded dramatically to gefitinib were observed. In both cases, the performed targeted EGFR-sequencing did not reveal "activating" mutations, thereby showing no apparent correlation between, for example, the treatment response and EGFR amplification, thereby underlining the need for biomarkers, whereby the presence or absence of these biomarkers serves as an indicator of how well a subject will respond to a certain treatment, or if a patient will respond to the intended treatment at all. Thus, in a one example, the present invention refers to a method of predicting susceptibility of a subject suffering from cancer to a treatment with an anti-cancer drug.

The basis for determining subject susceptibility to treatment with a particular drug can be, for example, the presence or the absence of, for example genetic alternations or mutations within the genome, within genetic transcripts, such as RNA or within proteins expressed by genes. The genetic mutation or alteration in question may or may not result in a change in for example protein or RNA sequence, depending on the type of mutation in question. For example, different from an activating mutation, a silent mutation will not result in any discernible change in metabolism or expression product, as the mutation is silent. A point mutation may or may not be silent, depending on the exact mutation at hand and the result of said mutation. For example, if a point mutation results in the change of one amino acid for another, wherein the new amino acid results in a different tertiary structure of the resulting protein, then such a mutation is not considered to be a silent mutation. However, if the point mutation results in a different RNA sequence, which still results in the same amino acid at that point of the protein (due to the redundancy in the genetic code, that is the fact that multiple codons encode for the same amino acid), the point mutation will be considered a silent mutation.

The present application also discloses a method, which comprises detecting the presence or absence of a genetic alteration in an antisense strand of a long non-coding RNA (lncRNA). This long, non-coding RNA (lncRNA) sequence can reside in an antisense strand of an oncogene. In another example, the long non-coding RNA (lncRNA) sequence resides in the coding strand of an oncogene. Thus, in one example, a method is disclosed herein, which comprises detecting the presence or absence of a genetic alteration in an antisense strand of a long non-coding RNA (lncRNA). In another example, the genetic alteration alters or disrupts expression of the oncogene. In another example, disclosed herein is a method of predicting susceptibility of a subject suffering from cancer to a treatment with an anti-cancer drug, wherein the method comprises detecting the presence or absence of a mutation in an antisense strand of a non-coding RNA of an oncogene, wherein the mutation alters or disrupts expression of the oncogene. In another example, the long non-coding RNA (lncRNA) sequence resides in the coding strand of an oncogene. In yet another example, if the genetic alteration or mutation is present, the subject is predicted to show improved susceptibility to the treatment with the anti-cancer drug compared to a subject not carrying the mutation. In one example, there is disclosed a method of predicting susceptibility of a subject suffering from cancer to a treatment with an anti-cancer drug, wherein the method comprises detecting the presence or absence of a genetic alteration in a long non-coding RNA (lncRNA) that resides in an antisense strand of an oncogene, wherein the genetic alteration alters or disrupts expression of the oncogene; wherein in case the genetic alteration is present, the subject is predicted to show improved susceptibility to the treatment with the anti-cancer drug compared to a subject not carrying the genetic alteration.

As used herein, the term "alters" refers to a change in a characteristic, usually in comparison to the same characteristic in a different state. A difference in, for example, expression level of a known gene can be considered to be an alteration of the gene expression of said gene. This is usually given in comparison to the disease-free (or healthy) state of the gene. Such a difference in expression, gene protein or otherwise can be given in absolute or in relative terms. For example, gene Z is expressed at a level of 50 in a disease-free state, given in absolute terms. In a diseases state, gene Z is expressed at a level of 25. In relative terms, the gene expression of gene Z would be 0.5 in the diseased state relative to the disease-free state (also termed to be a down-regulation of the expression of gene Z). In another example, gene Z is expressed at a level of 50 in a disease-free state, given in absolute terms. In a diseases state, gene Z is expressed at a level of 100. In relative terms, the gene expression of gene Z would be 2 in the diseased state relative to the disease-free state (also termed to be up-regulation of the expression of gene Z). In both of these examples, the gene expression of Z is altered.

As used herein, the term "disrupt" refers to the interruption, interference or termination of a process. For example, the presence of a mutation within a gene sequence can result in the disruption of the translation process, thereby usually resulting in either the truncation of the resulting protein (protein is only partially expressed, for example through the introduction of a premature stop codon via the mutation) or the complete absence of the protein (no protein is expressed).

In another example, there is described a method of treating cancer in a subject suffering from said cancer, wherein the method comprises detecting the presence or absence of a mutation or a genetic alteration in a non-coding RNA on an antisense strand of an oncogene related to the cancer, wherein the mutation alters or disrupts expression of the oncogene; administering an anti-cancer drug for the cancer type the subject suffers from in case the presence of the mutation is confirmed. In another example, there is disclosed use of an anti-cancer drug in the manufacture of a medicament for treating cancer in a subject suffering from said cancer, wherein the medicament is to be administered to the subject when the presence or absence of a mutation or a genetic alteration in a non-coding RNA on an antisense strand of an oncogene related to the cancer is detected, wherein the mutation alters, or disrupts expression of the oncogene.

There are various targets known to function as oncogenetic switches in a cell. These target genes are, but are not limited to, regulatory genes within any given pathway involved in cell growth and regulation of cell proliferation and/or apoptosis. As phosphorylation is one of the best known examples of cellular switches used for regulating cellular pathways, genes that express kinases (enzymes responsible for the transfer of phosphor groups from one protein to another protein) are prominent targets in the development of anti-cancer drugs and regimens. Other categories of oncogenes include, but are not limited to, receptor tyrosine kinases, tyrosine kinases, cytoplasmic tyrosine kinases, cytoplasmic serine/threonine kinases, cytoplasmic serine/threonine kinases regulatory subunits, cyclin-dependent kinases, regulatory GTPases and transcription factors. Thus, in one example, the oncogene is a gene that results in, but is not limited to, the expression of a receptor tyrosine kinase, a protein target of a receptor tyrosine kinase or in a cytoplasmic tyrosine kinase. In another example, the oncogene is a gene that results in the expression of a receptor tyrosine kinase. In another example, the oncogene that results in the expression of a receptor tyrosine kinase is, but is not limited to, EGFR, IGF1R, PIK3CD, PIK3R3, PIK3CD, ERBB4, FGFR2, FGFR3, FGFR4, c-Kit, PDGFRA, PDGFRB, PIK3CA, PIK3Ra, PIK3R2, PIK3R3, ERBB2, ERBB3 and INSR. In one example, the oncogene is a gene that results in the expression of a cytoplasmic tyrosine kinase. In another example, the oncogene that results in the expression of a cytoplasmic tyrosine kinase is, but is not limited to, mTOR, MAP3K1 (MEKK) MAPK8 (JNK) and BRAF.

In another example, an oncogene includes, but is not limited to, epidermal growth factor receptor (EGFR), platelet-derived growth factor receptor (PDGFR), vascular endothelial growth factor receptor (VEGFR), PIK3CB, PIK3R3, PIK3CD, ERBB4, BRAF, FGFR2, FGFR3, FGFR4, c-Kit, MAPK3K1 (MEKK), MAPK8 (JNK), PDGFRA, PDGFRB, PIK3CA, PIK3R1, PIK3R2, ERBB3, INSR, abl, af4/hrx, akt-2, alk, alk/npm, aml1, aml1/mtg8, axl, bcl-2, bcl-3, bcl-6, bcr/abl, c-myc, dbl, dek/can, E2A/pbx1, enl/hrx, erg/TLS, erbB, erbB-2/HER2/neu, ets-1, ews/fli1, fms, fos, fps, gli, gsp, hox11, hTERT, hst, IGF1R, IL-3, int-2, jun, kit, kmt2b, kmt2c, kmt2d, KS3, K-sam, Lbc, lck, imol, lmo2, L-myc, lyl-1, lyt-10, lyt-10/C-alpha-1, mas, mdm2, mll, mos, mtg8/aml1, myb, MYH11/CBFB, n-myc, ost, pax-5, pbx1/EA2, pim-1, PRAD-1, raf, rar/pml, ras, rasH, rasK, rasN, rel/nrg, ret, rhom1, rhom2, ros, ski, SRC, sis, tal1, tal2 (SCL), tan-1, tiam1, TSC2, and trk. In another example, the oncogene can include, but is not limited to, of EGFR, IGF1R, mTOR, PIK3CB, PIK3R3, PIK3CD, ERBB4, BRAF, FGFR2, FGFR3, FGFR4, c-Kit, MAPK3K1 (MEKK), MAPK8 (JNK), PDGFRA, PDGFRB, PIK3CA, PIK3R1, PIK3R2, ERBB2, ERBB3 and INSR. In yet another example, the oncogene can be, but is not limited to, EGFR, IGF1R, mTOR, PIK3CB, PIK3R3, PIK3CD, and ERBB4. In a further example, the oncogene is EGFR.

As defined above, various genes become oncogenes, in some examples, due to a mutation within their genetic sequence, thereby resulting in deviations from the usual function of said gene. In terms of gene targeting, there are multiple levels which can be targeted using available technology. That is to say, influencing gene expression and/or the resulting protein expression can be done on different levels. For example, one can influence the expression of a certain gene by silencing said gene using, for example, siRNA. Thus, the present disclosure describes methods of detecting differences in gene expression, based on which a susceptibility of a subject to a particular treatment is inferred.

In one example, this inference is performed based on the presence or absence of a mutation within the oncogene, or in any expression products of the oncogene. In one example, the presence of a mutation has an effect on the functionality of the resulting protein. In another example, the presence of the mutation does not have an effect on the functionality of the resulting protein.

Determination of the differences in gene expression can be performed using methods known to those skilled in the art. For example, gene sequencing can be used to ascertain if a mutation is present on a nucleic acid level. In another example, the comparison of gene expression can be done on a RNA level, that is for example, by ascertaining and comparing the levels of an RNA transcript of one or more target genes. In another example, the comparison of expression levels of a gene is made on the protein level. This can be performed, for example, by comparing the level of a protein expressed by a target gene in a diseased subject and comparing the level of the same protein in a disease-free subject.

In one example, the presence or absence of the mutation is determined in the RNA transcript of the gene. In another example, the presence or absence of the mutation is determined on the antisense strand of the RNA. In yet another example, the presence or absence of the mutation is determined in a non-coding region of the antisense strand of the RNA. In another example, the presence or absence of the mutation is determined on the antisense strand of a long non-coding RNA region (lncRNA) of the oncogene in question. The antisense strand of a long non-coding RNA region (lncRNA) of an oncogene can be, but is not limited to, EGFR-AS1 for EGFR gene; TRAIN for IGF1R gene, MTOR-AS1 for MTOR gene; GAPDHP39 and RPL23AP40 for PIK3CB gene; LOC101929626 for PIK3R3 gene; PIK3CD-AS1, PIK3CD-AS2 and RPL26P7 for PIK3CD gene and RNA5SP119 for ERBB4 gene. In another example, the mutation is determined in exon 20 of EGFR-AS1 of EGFR. In yet another example, the mutation is a silent mutation at position Q787Q of exon 20 in exon 20 of EGFR-AS1 of EGFR. In another example, the silent mutation is a G>A mutation at position Q787Q of exon 20 in exon 20 of EGFR-AS1 of EGFR.

Mutations on a genetic level, for example in the mRNA or in the gene itself, can result in the expressed protein or RNA being different from that which is usually expressed in the majority of the population. This difference can be seen in various ways, for example when a genetic mutation results in the over- or under-expression of the resulting (functional) protein or RNA transcript. In one example, the genetic mutation results in an over- or under-expression of the resulting RNA transcript in a subject. In a further example, the genetic mutation results in the expression of a truncated RNA transcript or no expression of an RNA transcript. In another example, the genetic mutation results in a non-functional protein being expressed. In yet another example, the genetic mutation results in a truncated protein being expressed. In another example, the genetic mutation results in a different isoform of the protein being expressed. In yet another example, the genetic mutation results in a change in ratio of various proteins, for example, the increased expression of a normally under-expressed isoform. In one example, a mutation in the antisense strand of the long non-coding RNA of EGFR (EGFR-AS1) results in the increased expression of EGFR isoform D. In another example, a mutation in the antisense strand of the long non-coding RNA of EGFR (EGFR-AS1) results in an increased EGFR isoform D to EGFR isoform A ratio (EGFR isoform D/A). In yet another example, there is disclosed a method of treating a subject suffering from an EGFR-related cancer, comprising administering to the subject an effective amount of a therapeutic agent affecting EGFR-AS1 lncRNA expression, or affecting EGFR-AS1 expression, or increasing the amount of EGFR isoform D and/or decreasing EGFR isoform A or a combination thereof; and administering to the subject an effective amount of a tyrosine kinase inhibitor used to treat the EGFR-related cancer. In another example, there is disclosed the use of a tyrosine kinase inhibitor in the manufacture of a medicament for treating a subject suffering from an EGFR-related cancer.

In another example, there is described a method of predicting the susceptibility of a subject suffering from cancer related to EGFR to a treatment with an EGFR inhibitor, the method comprising determining whether either one or two or all of the following is given: i) the subject has a silent G>A mutation at Q787Q position in exon 20 of EGFR; ii) the subject has lower EGFR-AS1 or EGFR-AS1 lncRNA expression level compared to subject that does not respond to treatment with an EGFR inhibitor; iii) the subject has higher EGFR isoform D/isoform A ratio compared to subject that does not respond to treatment with an EGFR inhibitor; wherein in case one or two or all of i) to iii) is given the subject is predicted to show improved susceptibility to a treatment with an EGFR inhibitor compared to a subject not showing any of i) to iii).

A genetic alteration or mutation within a genome can result in a genotype that is either homozygous or heterozygous for said mutation. As used herein, the terms "homozygous" and "heterozygous" refer to the degree of similarity between the alleles of a certain characteristic, or trait, of an organism. This is based on the fact that most eukaryotes are diploid, that means they have two matching sets of chromosomes. Both sets of chromosomes have the same loci on each of them. Thus, an organism that has a homozygous genotype is describing an organism (or cell) in which the alleles at a given locus are identical. On the other hand, if an organism is described as being heterozygous for a certain allele, this means that in the same locus, one chromosome shows one genotype (for example the nucleotide A), while the other chromosome shows a different genotype (for example, the nucleotide T) in the same locus. The question of homo- or heterozygosity can also be determined based on the presence or absence of genetic alterations or mutations in the respective RNA or RNA transcripts from each allele. Thus, in one example, if the RNA transcripts from alleles show the same mutation in the same locus, then the organism is considered to be homozygous for that mutation. In a preferred example, the mutation or genetic alternation is homozygous. In yet another example, the mutation or genetic alteration is heterozygous.

It is also possible to determine the presence or absence of a genetic alteration or mutation on, for example, the corresponding antisense RNA strand or in long non-coding RNA (lncRNA). The present examples disclose a mutation or genetic alteration at a specific position within the EGFR-AS1 sequence. Thus, in one example, a defined locus within an antisense strand of a long non-coding RNA sequence is homozygous for a mutation or genetic alteration. In another example, the genetic alteration or mutation in long non-coding RNA (lncRNA) that resides in an antisense strand of an oncogene is homozygous. In one example, the mutation or genetic alteration is present in the EGFR-AS1 sequence. In another example, the mutation or genetic alteration is present in the Q787Q locus of the EGFR-AS1 sequence. In one example, this locus is homozygous for a mutation or genetic alteration. This means that at this location, the mutation or genetic alteration (and as a result the genotype) on both alleles are the same. In another example, this locus is heterozygous for the mutation or genetic alteration. In a further preferred example, the homozygous mutation or genetic alteration is AA. In a further example, the heterozygous mutation or genetic alteration is GA.

The basis of comparison for determining the presence or absence of a mutation and/or the effect of such a mutation on the expression of the resulting protein or RNA is the comparison with a subject who is either healthy, that is disease-free, or a subject who has the same disease as the subject in question, but who is known not to respond to the treatment being assessed for the subject in question. For example, subject A has head and neck cancer. A mutation is found within the oncogene closely related to the cancer, for example EGFR. Subject B also has head and neck cancer and was treated with anti-cancer drug X, which was not effective in the treatment of the cancer. Subject C also has head and neck cancer and was successfully treated with anti-cancer drug X. Genetic comparison of the oncogene closely related to the cancers in subjects B and C (in this example, EGFR) show that the oncogene of subject B does not have a mutation in a relevant, pre-determined region of the oncogene, while subject C does present a mutation in the relevant, pre-determined region of the oncogene. Thus, subject A, having a mutation present in the same region as subject C, is shown to be susceptible to treatment with anti-cancer drug X. In another example, the determination of possible susceptibility to treatment with a given anti-cancer drug can be done based on the comparison of, for example, protein or RNA levels, or in the case of multiple proteins or RNA transcripts, and/or ratios of the proteins concerned. In one example, it is determined whether the subject has a higher EGFR isoform D/isoform A ratio compared to a subject that does not respond to treatment with the anti-cancer drug. In one example, it is determined whether the subject has a lower RNA transcript level compared to a subject that does not respond to treatment with the anti-cancer drug. In another example, it is determined whether the subject has lower EGFR-AS1 or EGFR-AS1 lncRNA expression level compared to a subject that does not respond to treatment with the anti-cancer drug. In yet another example, the method as described herein further comprises measuring of either one or both of the following for predicting the susceptibility: i) whether the subject has lower EGFR-AS1 or EGFR-AS1 lncRNA expression level compared to a subject that does not respond to treatment with the anti-cancer drug; ii) whether the subject has higher EGFR isoform D/isoform A ratio compared to a subject that does not respond to treatment with the anti-cancer drug, wherein the anti-cancer drug is a tyrosine kinase inhibitor or an EGFR inhibitor.

Thus, in one example an increase in the amount of EGFR isoform D in a patient is indicative of an increased sensitivity to treatment with, for example, a tyrosine kinase inhibitor for EGFR-related cancers, or treatments used for other gene specific cancers. In another example, a decrease in the amount of EGFR isoform A in a patient is indicative of an increased sensitivity to treatment with a tyrosine kinase inhibitor. In other words, a high ratio of EGFR isoform D to EGFR isoform A is considered to be indicative an increased sensitivity to treatment with, for example, a tyrosine kinase inhibitor for EGFR-related cancers, or treatments used for other gene specific cancers. Conversely, a low ratio of EGFR isoform D to EGFR isoform A is considered to be indicative of a possible resistance to treatment with, for example, a tyrosine kinase inhibitor for EGFR-related cancers, or treatments used for other gene specific cancers.

It is known that certain oncogenes are more closely associated with some types of cancer than others. For example, the gene HER2 is a known oncogene most closely associated, but not only associated, with certain subtypes of breast cancer. Thus, in the present disclosure, the absence or presence of a mutation in an oncogene is understood to have an effect on the subject s susceptibility to a treatment for, for example, a cancer related to said oncogene. In one example, the cancer related to EGFR, PIK3CB, PIK3R3 and PIK3CD is, but is not limited to, non-small cell lung carcinoma, head and neck cancer, colorectal carcinoma, breast cancer, brain malignancies including glioblastomas, haematological malignancies, prostate cancer, bladder cancer, renal cell carcinoma, pancreas cancer, cervical cancer, oesophageal cancer, gastric cancer and ovarian cancer. In another example, the cancer related to EGFR is head and neck cancer, or lung cancer. In yet another example, the head and neck cancer can be head and neck squamous cell cancer (HNSCC) or oral squamous cell cancer (OSCC). IN yet another example, the lung cancer is non-small cell lung cancer (NSCLC). In one example, the cancer related to PIKCD is haematological malignancies. In one example, the cancer related to ERBB4 is breast cancer. In one example, the cancer related to EGFR is, but is not limited to, non-small cell lung cancer (NSCLC), head and neck cancer, colorectal carcinoma, breast cancer, brain malignancies including glioblastoma, prostate cancer, bladder cancer, renal cell carcinoma, pancreas cancer, cervical cancer, oesophageal cancer, gastric cancer and ovarian cancer.

Just as there are known genes closely related to particular types of cancer, there are also treatments, for example anti-cancer treatments that are known to work better with certain cancer types compared to other treatments for the same type of cancer. Without being bound by theory, it is thought that such differences in treatment susceptibility are the result of the anti-cancer treatment pinpointing, for example, a defective cellular or signalling pathway. For example, a cancer related to the HER2 gene, wherein the HER2 gene is defective or results in a defective product (for example, RNA or protein RNA or protein), said cancer related to the HER2 gene can be more susceptible to treatment with for example trastuzumab, compared to a treatment with other anti-cancer drugs. Therefore, in one example, the anti-cancer drug is, but is not limited to gefitinib, erlotinib and afatinib for the treatment of cancer related to EGFR; OSI-906 (linsitinib) for the treatment of cancer related to IGF1R; everolimus (also known as RAD001) and sirolimus for the treatment of cancer related to mTOR; BKM120 (buparlisib) and BYL719 (alpelisib) for the treatment of cancer related to PIK3CB and PIK3R3; idelalisib for the treatment of cancer related to PIK3CD and dacomatinib and lapatinib for the treatment of cancer related to ERBB4, or combinations thereof. In one example, the anti-cancer drug used for treating EGFR-related cancers is, but is not limited to, gefitinib, erlotinib, afatinib or combinations thereof. In another example, the anti-cancer drug used for treating mTOR-related cancers is, but is not limited to, everolimus (RAD001), sirolimus, or combinations thereof. In another example, the anti-cancer drug used for treating IGF1R-related cancers is, but is not limited to, linsitinib. In another example, the anti-cancer drug used for treating PIK3CB and PIK3R3-related cancers is, but is not limited to, BKM120 (buparlisib), BYL719 (alpelisib) or combinations thereof. In another example, the anti-cancer drug used for treating PIK3CD-related cancers is, but is not limited to, idelalisib. In another example, the anti-cancer drug used for treating ERBB4-related cancers is, but is not limited to, dacomatinib, lapatinib, or combinations thereof. In one example, the anti-cancer drug is a tyrosine kinase inhibitor. In another example, the tyrosine kinase inhibitor is an EGFR inhibitor. In yet another example, the tyrosine kinase inhibitor is, but is not limited to, gefitinib, erlotinib, erlotinib HCl, lapatinib, dacomitinib, TAE684, afatinib, dasatinib, saracatinib, veratinib, AEE788, WZ4002, icotinib, osimertinib, BI1482694, ASP8273, EGF816, AZD3759, cetuximab, necitumumab, pannitumumab, nimotuzumab and combinations thereof. In a further example, the tyrosine kinase inhibitor is, but is not limited to, gefitinib, erlotinib, lapatinib and combinations thereof.

It is understood that some drugs/therapeutic agents, some of which are disclosed herein, can be used to treat most cancer types, albeit with differing efficacies. While, for example, gefitinib is not usually used in the treatment of, for example, head and neck squamous cell cancer (HNSCC), it is shown that according to the present invention, head and neck squamous cell cancer (HNSCC) can indeed be treated with gefitinib.

Some approaches are based on multi-pronged approached for treating a disease, while other may be based on a single-pronged approach, that is single treatment regimen, for a particular disease. In one example, the disease is treated using a single treatment. In another example, the disease is treated using at least two, at least three, at least four or more treatments. These treatments may be given subsequently, simultaneously or in combinations thereof. In one example, the disease is treated using at least two, at least three, at least four or more drugs.

Many types of anti-cancer drugs or treatments are available based on the specific type of cancer to be treated. For example, breast cancer can be treated with, but not limited to, any one of the following anti-cancer drugs, or with combinations thereof: everolimus (RAD001), tamoxifen, toremifene, trastuzumab, fulvestrant, anastrozole, exemestane, lapatinib, letrozole, pertuzumab, ado-trastuzumab emtansine, and palbociclib. A known mutation in an oncogene can therefore result in a more effective anti-cancer being chosen, as opposed to any of the above listed drugs being chosen. For example, if a mutation is detected in the HER2 gene in a breast cancer sample obtained from a subject, then the selection of trastuzumab for treating said cancer would be made, as trastuzumab is known for its high success rate in the treatment of HER2-mutation positive breast cancers.

The following provides various types of cancer and those anti-cancer drugs used to treat them. For example, adenocarcinomas of the stomach or gastro-oesophageal junction can be treated with, but not limited to, trastuzumab, ramucirumab or combinations thereof. Basal cell carcinomas can be treated with, but not limited to vismodegib, sonidegib or combinations thereof. Bladder cancer can be treated with, for example but not limited to, atezolizumab, everolimus, sirolimus and combinations thereof. Brain cancer can be treated with, but not limited to, bevacizumab, everolimus or combinations thereof. Breast cancer can be treated with, but not limited to, everolimus, tamoxifen, toremifene, trastuzumab, fulvestrant, anastrozole, exemestane, linsitinib, lapatinib, letrozole, pertuzumab, ado-trastuzumab emtansine, palbociclib, alpelisib and combinations thereof. Cervical cancer can be treated with, for example, but not limited to, bevacizumab. Colorectal cancer can be treated with, but not limited to, cetuximab, panitumumab, bevacizumab, ziv-aflibercept, regorafenib, ramucirumab and combinations thereof. Dermatofibrosarcoma protuberans can be treated with, for example, but not limited to, imatinib mesylate. Endocrine/neuroendocrine tumours can be treated with, for example, but not limited to, lanreotide acetate. Head and neck cancers can be treated with, but are not limited to, cetuximab, gefitinib, erlotinib, afatinib, alpelisib, linsitinib, buparlisib, idelalisib, dacomitinib, lapatinib and combinations thereof. Gastrointestinal stromal tumours can be treated with, but are not limited to, imatinib mesylate, sunitinib, regorafenib, and combinations thereof. Giant cell tumour of the bone can be treated with, for example, but not limited to, denosumab. Kaposi sarcoma can be treated with, for example, but not limited to, alitretinoin. Kidney cancer can be treated with, but not limited to bevacizumab, sorafenib, sunitinib, pazopanib, temsirolimus, everolimus, axitinib, nivolumab, cabozantinib, lenvatinib mesylate and combinations thereof. Leukaemia can be treated with, for example, but not limited to, tretinoin, imatinib mesylate, dasatinib, nilotinib, bosutinib, rituximab, alemtuzumab, ofatumumab, obinutuzumab, ibrutinib, idelalisib, blinatumomab, venetoclax and combinations thereof. Liver cancer can be treated with, for example, but not limited to, sorafenib. Lung cancer can be treated with, for example, but not limited to, bevacizumab, crizotinib, erlotinib, gefitinib, afatinib dimaleate, ceritinib, ramucirumab, nivolumab, pembrolizumab, osimertinib, necitumumab, alectinib and combinations thereof. Lymphomas can be treated with, for example, but not limited to, ibritumomab tiuxetan, denileukin diftitox, brentuximab vedotin, rituximab, vorinostat, romidepsin, bexarotene, bortezomib, pralatrexate, ibrutinib, siltuximab, idelalisib, belinostat, obinutuzumab, nivolumab and combinations thereof. Melanomas can be treated with, for example, but not limited to, ipilimumab, vemurafenib, trametinib, dabrafenib, pembrolizumab, nivolumab, cobimetinib, everolimus, sirolimus and combinations thereof. Multiple myelomas can be treated with, for example, but not limited to, bortezomib, carfilzomib, panobinostat, daratumumab, ixazomib citrate, elotuzumab and combinations thereof. Myelodysplastic/myeloproliferative disorders can be treated with, for example, but not limited to, imatinib mesylate, ruxolitinib phosphate and combinations thereof. Neuroblastomas can be treated with, for example, but not limited to, dinutuximab. Ovarian epithelial/fallopian tube/primary peritoneal cancers can be treated with, for example, but not limited to, bevacizumab, olaparib and combinations thereof. Pancreatic cancer can be treated with, for example, but not limited to, erlotinib, everolimus, sunitinib and combinations thereof. Prostate cancer can be treated with, for example, but not limited to, cabazitaxel, enzalutamide, abiraterone acetate, radium 223 dichloride, linsitinib and combinations thereof. Soft tissue sarcoma can be treated with, for example, but not limited to, pazopanib. Systemic mastocytosis can be treated with, for example, but not limited to, imatinib mesylate. Thyroid cancer can be treated with, for example, but not limited to, cabozantinib, vandetanib, sorafenib, lenvatinib mesylate and combinations thereof. The listing of a particular anti-cancer drug in the categories above does not preclude its use for treating other types of cancer.

Specific methods disclosed herein further comprise the administration of an additional therapeutic agent (i.e., a therapeutic agent other than the anti-cancer treatment disclosed herein). In certain examples, the anti-cancer treatments can be used in combination with at least one other therapeutic agent. Therapeutic agents include, but are not limited to antibiotics, anti-emetic agents, antidepressants, anti-fungal agents, anti-inflammatory agents, antiviral agents, other anticancer agents, immunomodulatory agents, expression modulating agents, alpha-interferons, gene silencing agents, agents capable of suppressing expression of RNA transcripts or proteins, agents capable of affecting RNA or protein expression, β-interferons, alkylating agents, hormones, or cytokines. In one example, the method encompasses the administration of an additional therapeutic agent that demonstrates gene silencing activity. In another example, the therapeutic agent is capable of RNA interference. In yet another example, the therapeutic agent is selected from, but not limited to, antisense oligonucleotides, short hairpin RNA (shRNA), small interfering RNA (siRNA), double stranded RNA (dsRNA), microRNA (miRNA), locked nucleic acids (LNAs) ribozymes, histone modification, RNA-directed DNA methylation, paramutations or combinations thereof. In one example, the therapeutic agent affects RNA expression. In yet another example, a method of treating a subject suffering from cancer is disclosed, comprising administering to the subject an effective amount of a therapeutic agent affecting expression of a non-coding RNA an oncogene, wherein the mutation alters or disrupts expression of the oncogene; and administering to the subject an effective amount of an anti-cancer drug specific for the cancer related to the oncogene. In another example, the therapeutic agent affects EGFR-AS1 expression. In a further example, the therapeutic agent affecting EGFR-AS1 expression comprises, but is not limited to, miRNA, shRNA, locked nucleic acids (LNAs), for example locked RNA or DNA, or siRNA. In yet another example, the therapeutic agent is one or more locked nucleic acids (LNAs). In another example, the therapeutic agent suppressing EGFR-AS1 expression comprises EGFR-AS1 targeting locked nucleic acids (LNA). In another example, the therapeutic agent increasing EGFR isoform D or decreasing EGFR isoform A comprises an agent modulating the alternative splicing of EGFR.

The drugs and treatments as disclosed herein and the other therapeutics agent can act additively or, synergistically. In one example, an anti-cancer drug is administered concurrently with the administration of another therapeutic agent, which can be part of the same composition or in a different composition. In another example, the anti-cancer agent is administered prior to or subsequent to administration of another therapeutic agent. In a separate example, an anti-cancer drug is administered to a subject who has not previously undergone or is not currently undergoing treatment with another therapeutic agent. In one example, the methods of the invention comprise the administration of one or more anti-cancer treatments without an additional therapeutic agent. In another example, the methods of the invention comprise the administration of one or more anti-cancer treatments with at least one or more additional therapeutic agents.

The methods and the treatments disclosed herein may be performed or carried out simultaneously, separately, one after the other, or in combination with other treatments. In one example, these treatments are, but are not limited to, radiation therapies, chemo-radiation, surgery, and combinations thereof. In case, for example, multiple treatments are implemented, these treatments can be performed or carried out, for example, one after the other, with a time interval between each treatment step, wherein, for example, the time interval between the first and the second treatment step is at least 1 to 24 hours, or at least 1, at least 4, at least 6, at least 8, at least 12, at least, or at least 1 or 2 or 3 or 4 or 5 or 6 or 7 days, or at least one week.

Figure 1B:
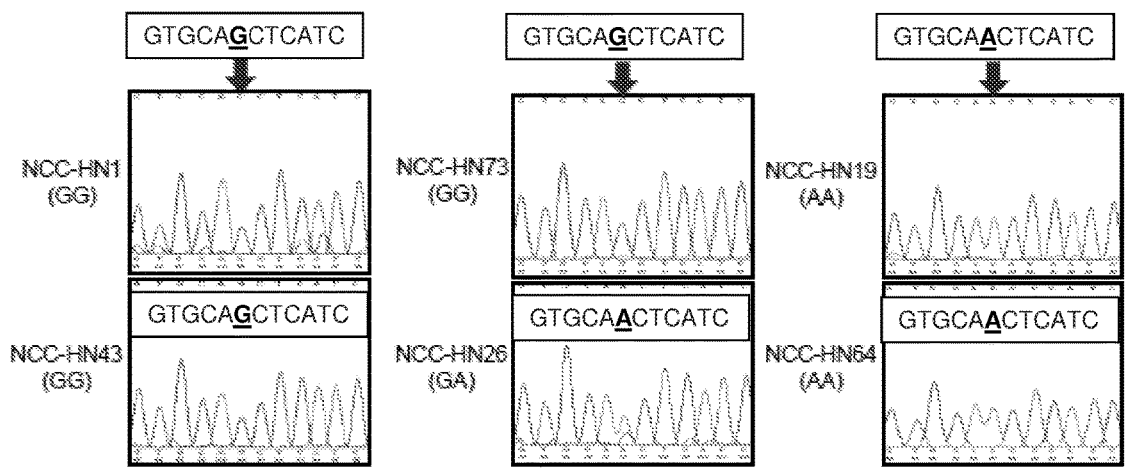
FIG. 1B is a set of DNA sequence trace chromatograms of Sanger sequencing, showing the disclosed AA genotype in cell lines with increased sensitivity to EGFR tyrosine kinase inhibitors (NCC-HN19 and NCC-HN64).
Figure 1C:
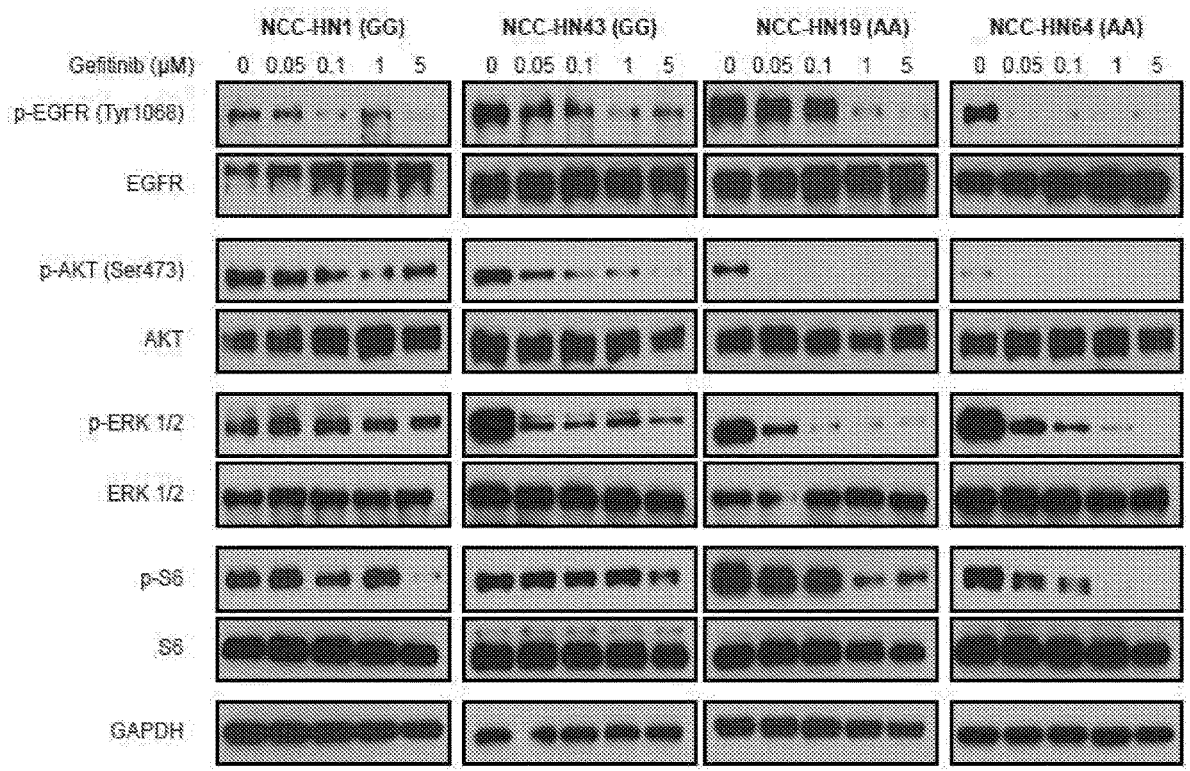
FIG. 1C is a set of images of western blot results showing EGFR pathway activation with and without tyrosine kinase inhibitors treatment in HNSCC cell lines with the indicated Q787Q genotype. Each cell line is compared in terms of rate of phosphorylation and also in terms of the effect of a treatment of gefitinib on the rate of phosphorylation, that is the presence of the p-version of the protein, versus the unphosphorylated version of the protein. For example, the first two rows compare the level of phosphorylation between EGFR and p-EGFR (that is the phosphorylated version of EGFR). As gefitinib is a known tyrosine kinase inhibitor, it is expected that the rate of phosphorylation is anti-proportional to the amount of gefitinib administered. That is to say the rate of phosphorylation will decrease with an increase in the amount of gefitinib administered. GAPDH acts as a loading control.
Figure 5:
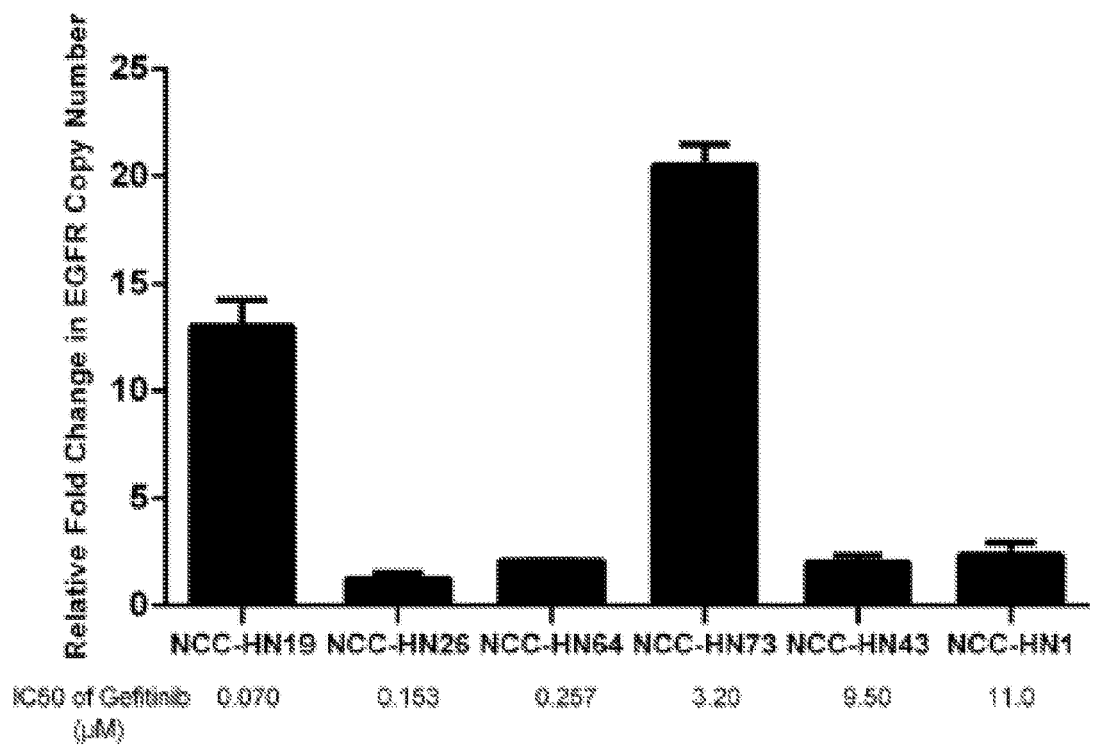
FIG. 5 is a set of column graphs showing the relative change in EGFR copy number in various cell lines, based on real-time PCR, with the gefitinib $IC_{50}$ values as indicated. This graph indicates that there is no association between EGFR copy number and the $IC_{50}$ values. Error bars indicate one standard deviation.

Differential Sensitivity to EGFR Tyrosine Kinase Inhibitor is Mediated by a Silent Polymorphism in EGFR Exon 20 in Patient Derived Oral Squamous Cell Carcinoma Cell Lines Six patient-derived cell lines established in the laboratory were tested for sensitivity to EGFR inhibitors using gefitinib, erlotinib and afatinib (FIG. 1A). As shown, majority of cell lines were insensitive to EGFR inhibition, except for NCCWHN19 and NCCWHN64, each with gefitinib $IC_{50}$ values within the therapeutic range (0.07 and 0.26 μM respectively). Targeted re-sequencing did not identify sensitizing EGFR mutations, nor was any correlation between drug sensitivity and EGFR copy number demonstrated (FIG. 5). Instead, the two sensitive lines were homozygous for the same synonymous SNP identified in a phase 2 trial (rs10251977, 2361 G>A, Q787Q; SEQ ID NO: 27) with the A/A genotype, while the insensitive cell lines were either homozygous wild type (G/G) or heterozygous (G/A) (FIG. 1B). In line with the observed phenotype, Western blots performed on the gefitinib-sensitive cell lines NCC-HN19 and NCC-HN64 (A/A genotype) showed a significant and consistent reduction in EGFR, AKT, ERK and S6 phosphorylation, after treatment with therapeutic doses of gefitinib (FIG. 1C). In contrast, cell lines with the G/G genotype (NCC-HN1 and NCC-HN43) required much higher drug doses to show effect on phosphor-AKT and phosphor-S6 levels, with modest, if any effect on phosphor-ERK.

Figure 1D:
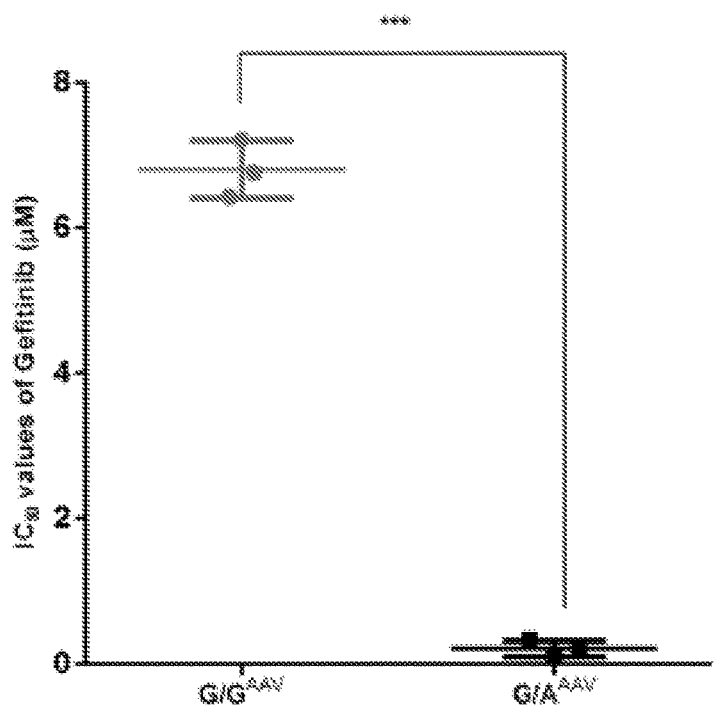
FIG. 1D is a graph of $IC_{50}$ values showing sensitivity to gefitinib in correctly targeted G/A$^{AAV}$ clones (CL16, CL19 and CL63) compared to G/G$^{AAV}$ negative controls (clones CL12, CL76 and CL77). This shows that the presence of the G/A mutation results in a stark difference in $IC_{50}$ values for gefitinib. In terms of $IC_{50}$ values for drugs, it is noted that the lower the $IC_{50}$ value, the more effective a drug is considered to be. Error bars indicate one standard deviation and p-value as indicated based on student s t-test.
Figure 1E:
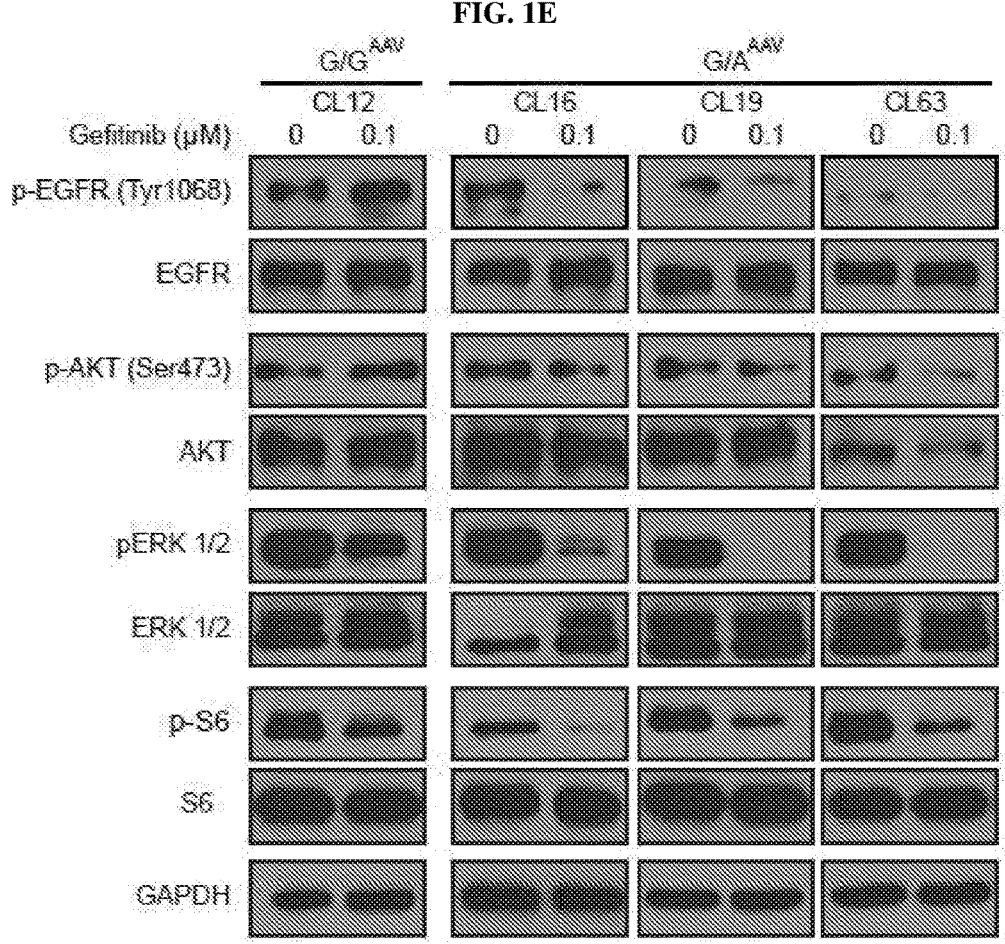
FIG. 1E is a set of images of western blot results showing inhibition of EGFR pathway activation with 0.1 µM gefitinib in G/A$^{AAV}$ clones CL16, CL63, CL19 compared to G/G$^{AAV}$ negative control (clone CL12).
Figure 6:
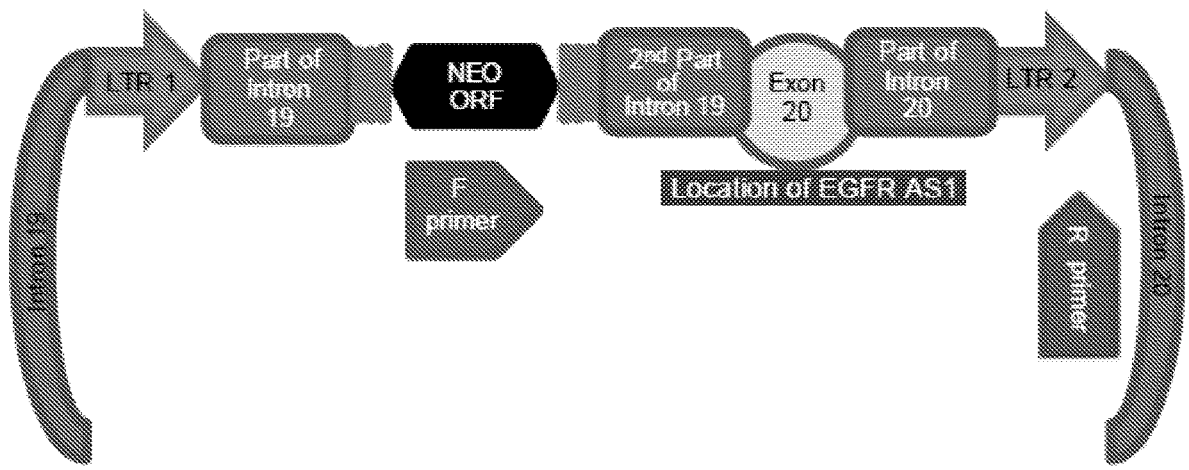
FIG. 6 is a schematic showing the targeting construct and strategy designed to alter the Q787Q genotype from G to A. The binding location of the primers used for PCR screening and location of EGFR-AS1 in this construct are indicated.
Figure 7:
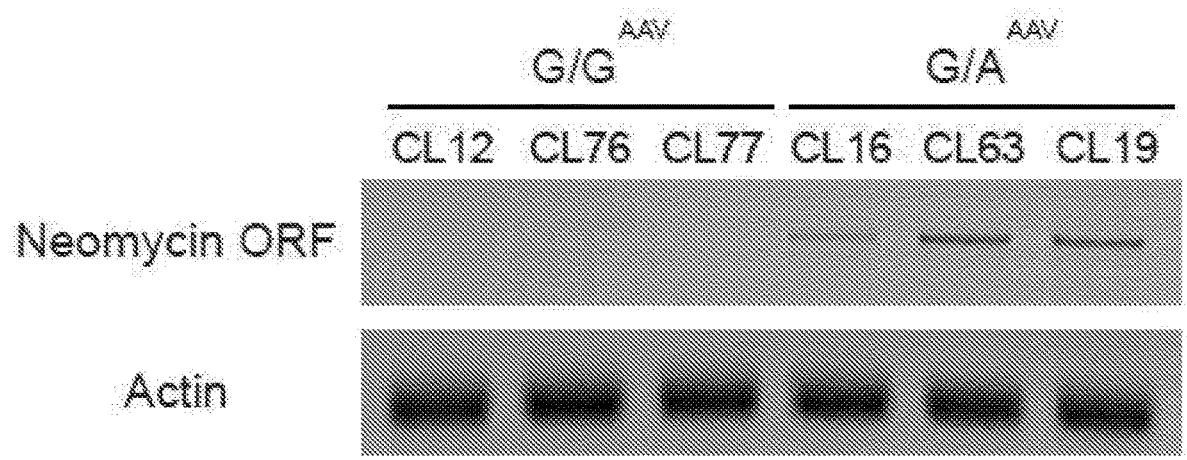
FIG. 7 is a set of DNA gel images showing the PCR screening results showing correct targeting in clones CL16, CL63 and CL19 with random integration in CL12, CL76 and CL77. Random integration means that the clones CL12, CL76 and CL77do not have the desired effect of a 'knock-in' for the G>A switch, but instead have randomly integrated into the cell line genome, thereby producing a negative control.

Single Nucleotide Targeting Reverse EGFR Tyrosine Kinase Inhibitor Resistant Phenotype in Isogenic Cell Lines The Horizon AAV targeting system was utilized to genetically knock-in the single nucleotide alteration and convert a resistant line (NCC-HN1) to a sensitive line in an isogenic cell line system (FIGS. 6 and 7). Sanger sequencing of the expressed EGFR cDNA confirmed that the A genotype was expressed in the successfully targeted clones (G/A$^{AAV}$:NCC-HN1 CL16, 63 and 19 respectively), compared to negative controls where the vector has integrated randomly (G/G$^{AAV}$: NCC-HN1 CL12, 76 and 77 respectively) (data not shown). Drug treatment of the G/A$^{AAV}$ clones showed an increased sensitivity to gefitinib compared to negative controls. $IC_{50}$ values of G/A$^{AAV}$ clones ranged from 0.1-0.3 μM, compared to negative controls (G/G$^{AAV}$) ranged from 6.4-7.2 μM ($IC_{50}$ for NCC-HN1 parental cell line ranged from 7-11 μM; FIG. 1D), with consistent modulation of downstream pathways (FIG. 1E).

EGFR-AS1 Long Non-Coding RNA Drives In Vitro and In Vivo EGFR Addiction

Figure 2A:
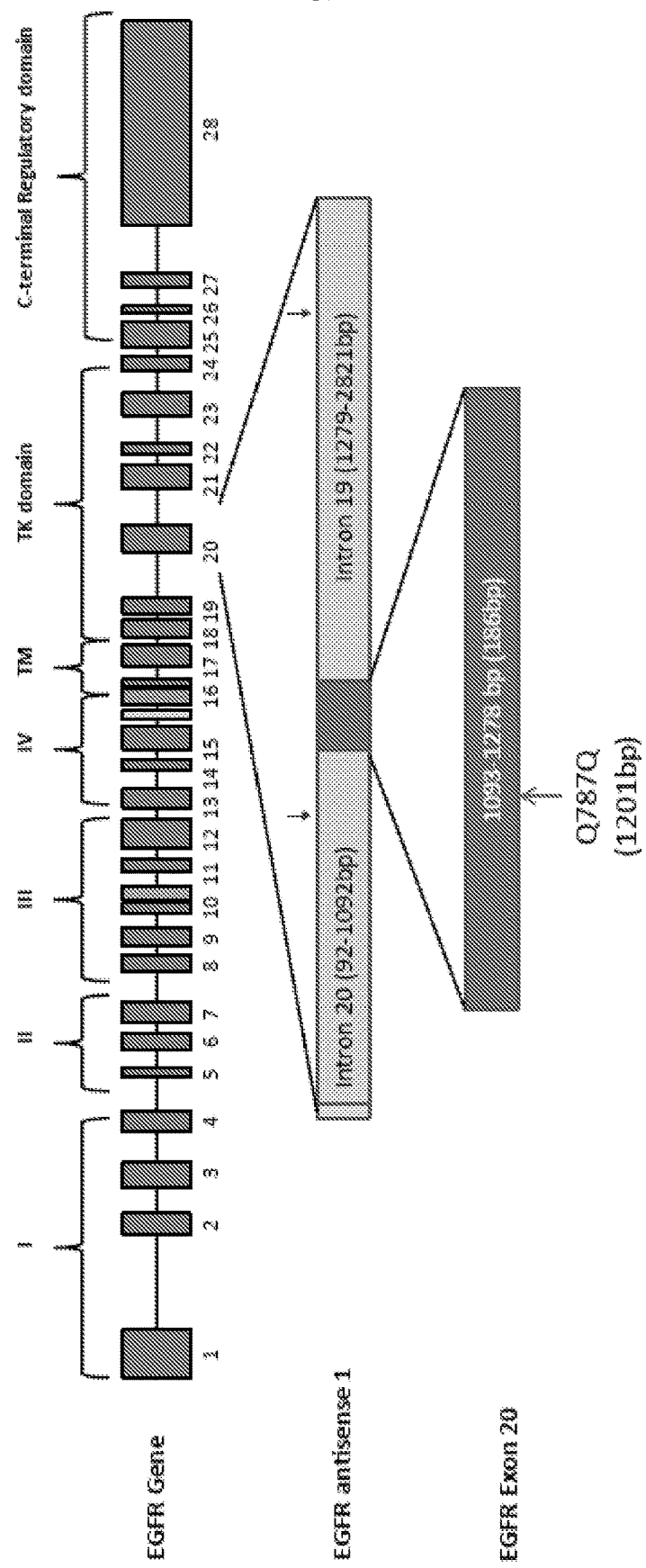
FIG. 2A is a schematic showing the genomic position of the EGFR-AS1 lncRNA relative to exon 20 of the EGFR gene, and position of the Q787Q SNP, with arrows indicating position of the siRNA designed to knockdown this EGFR-AS1 lncRNA.
Figure 2B:
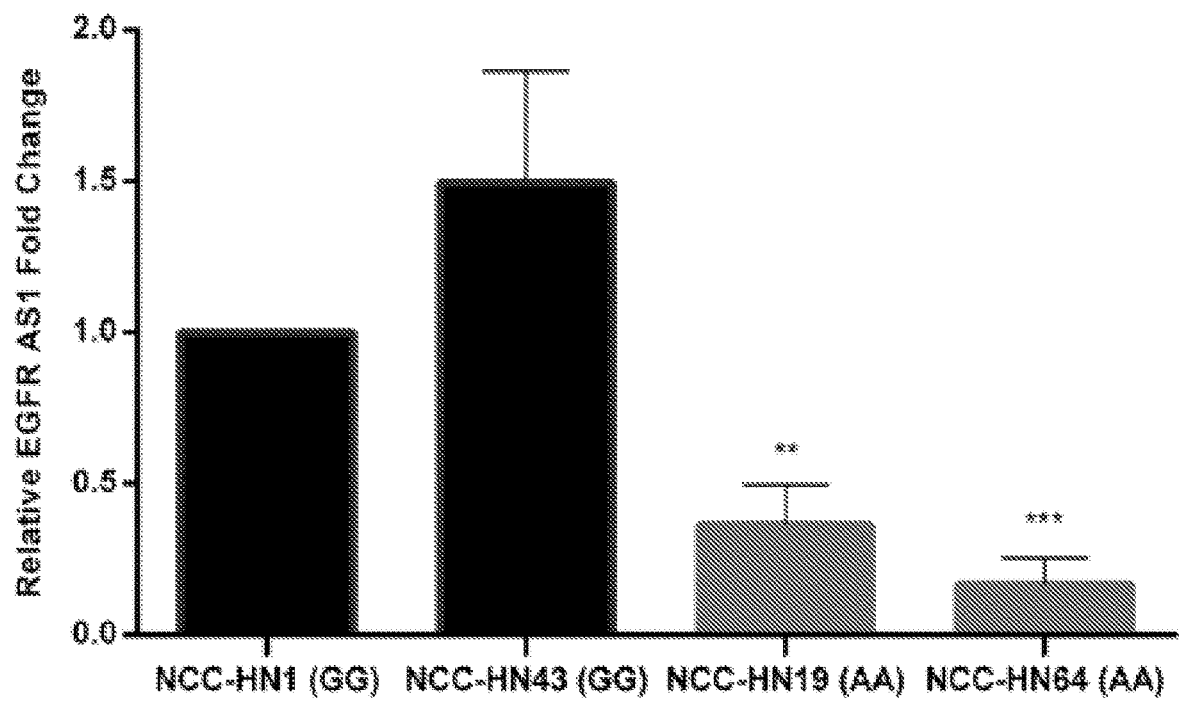
FIG. 2B is a set of column graphs showing expression levels of the EGFR-AS1 lncRNA transcripts measured by real-time RT-PCR. in lines with AA (NCC-HN19 and NCC-HN64) and G/G genotypes (NCC-HN1 and NCC-HN43), and the isogenic NCC-HN1 clones with correct targeting (G/A$^{AAV}$: CL16, CL63, and CL19) and negative controls (G/G$^{AAV}$: CL CL12, CL76, and CL77). Error bars indicate one standard deviation. Asterisks denote significance by student t-test (*–p<0.05, –p<0.01, *–p<0.001).
Figure 2B:
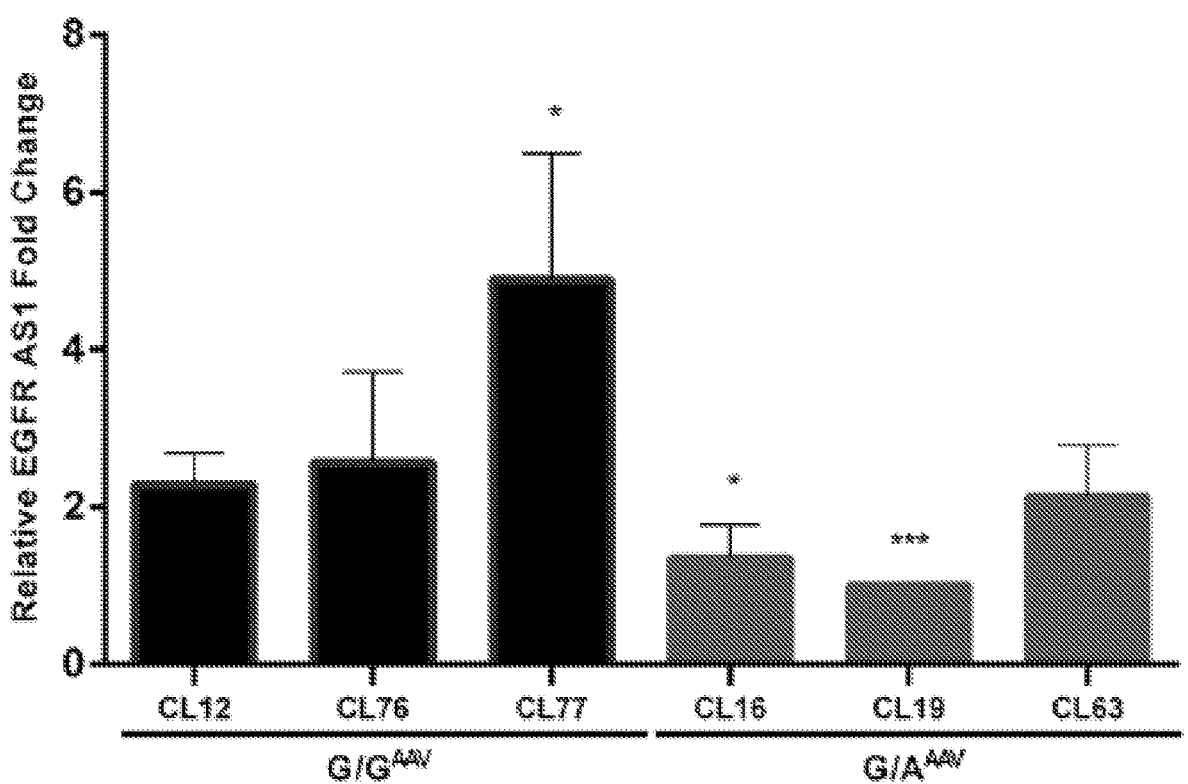
Figure 2C:
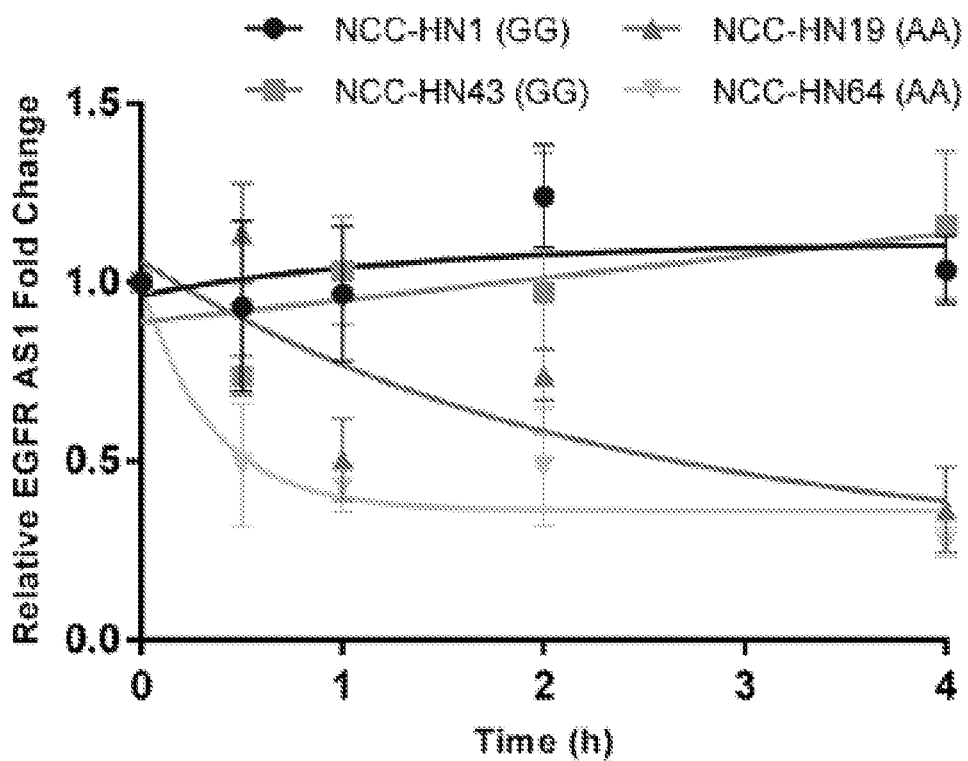
FIG. 2C is a set of line graphs showing trend of EGFR-AS1 levels (measured by real-time RT-PCR) after Actinomycin D treatment in lines with AA (NCC-HN19 and NCC-HN64) and G/G genotypes (NCC-HN1 and NCC-HN43), and the isogenic NCC-HN1 clones with correct targeting (G/A$^{AAV}$: CL16, and CL19) and negative controls (G/G$^{AAV}$: CL12 and CL77). Error bars indicate one standard deviation.
Figure 2C:
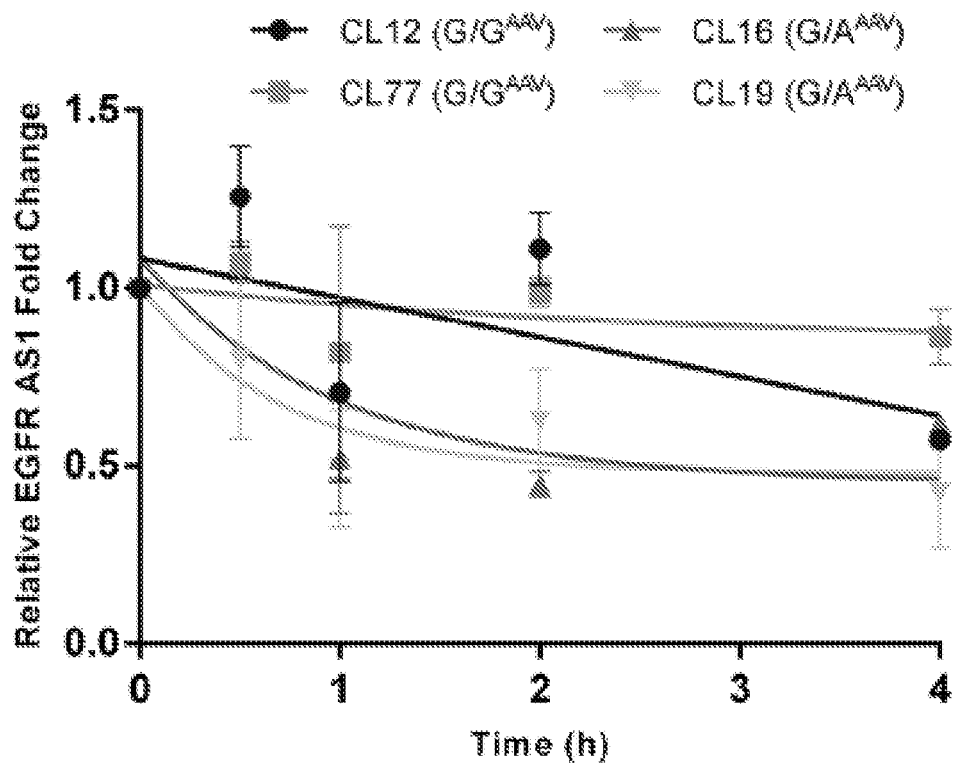
Figure 2D:
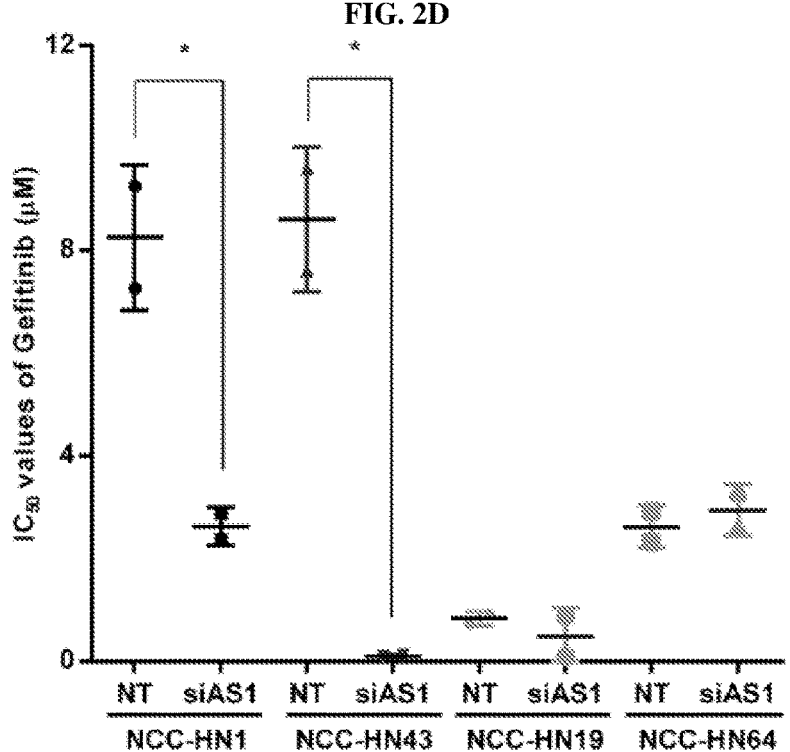
FIG. 2D is a graph showing $IC_{50}$ values of gefitinib in cell lines with knockdown of EGFR-AS1 (siAS1) compared to non-targeting controls (NT). As stated previously, it is noted that the lower the $IC_{50}$ value, the more effective a drug is considered to be. Error bars indicate one standard deviation. Asterisks denote significance by student t-test (*–p<0.05, –p<0.01, *–p<0.001).
Figure 2E:
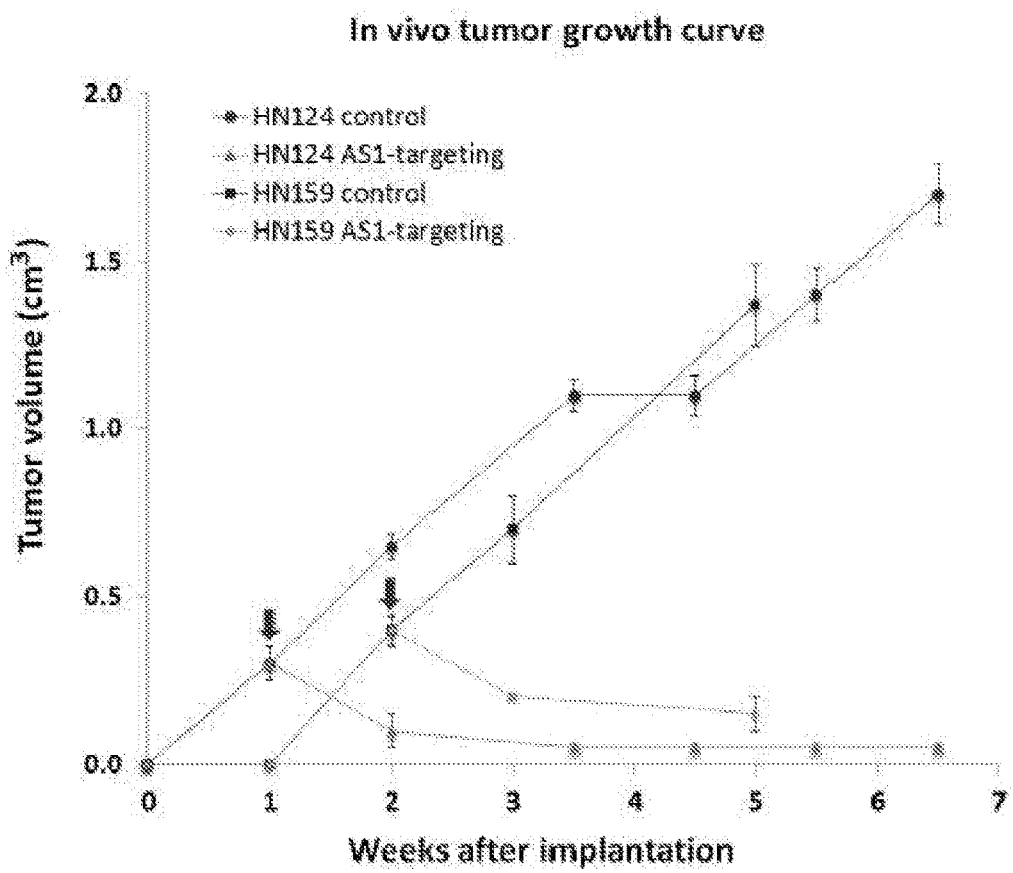
FIG. 2E is a line graph showing tumour growth levels in AS1-high PDXs HN124 and HN159 after treatment with AS1-targeting LNA and non-targeting control. Error bars indicate one standard deviation.
Figure 8:
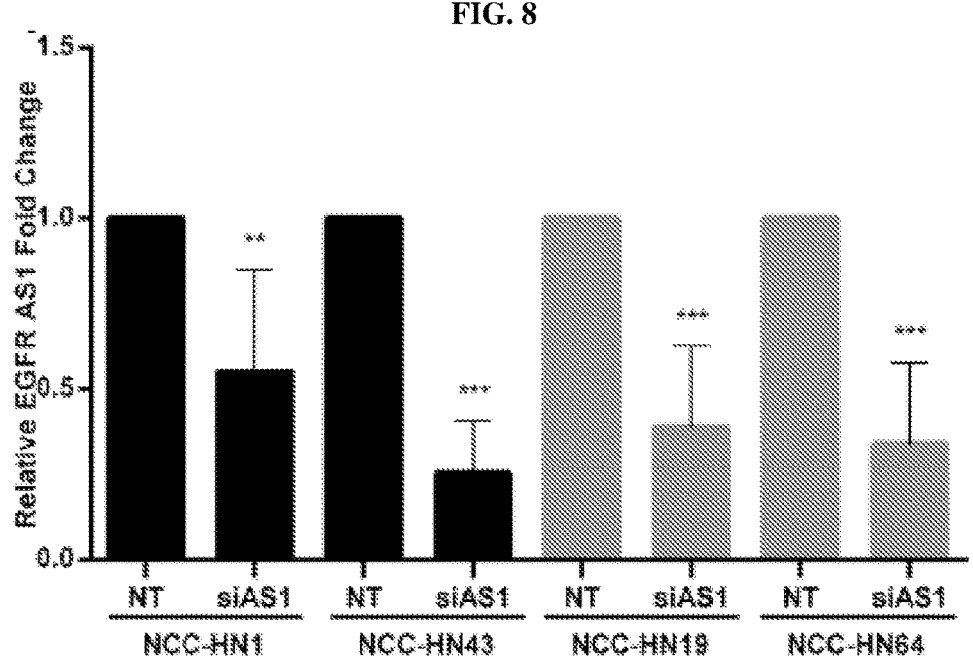
FIG. 8 is a bar graph showing the relative fold change in levels of EGFR-AS1, as measured by real-time RT-PCR after knockdown (siAS1), compared to non-targeting controls (NT) in cell lines as indicated. The LNA control is a non-targeting LNA. Error bars indicate one standard deviation. Asterisks denote significance by student t-test (*-p<0.05, -p<0.01, *-p<0.001).
Figure 9:
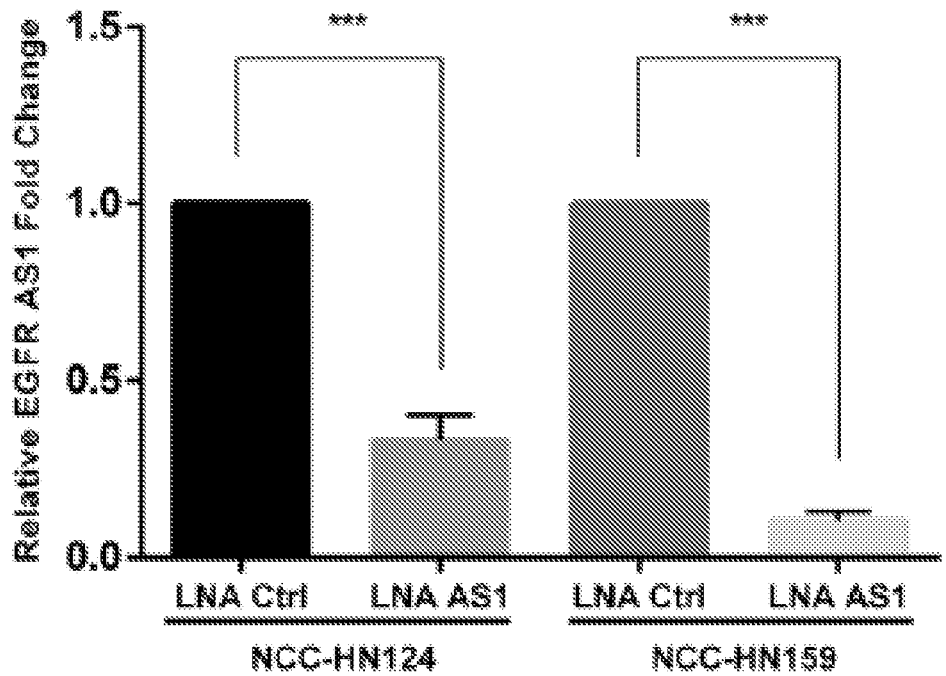
FIG. 9 is a bar graph showing real-time RT-PCR result showing relative fold change in the transcript levels of AS1 and isoform D/A ratio after in vivo targeting of EGFR-AS1 in HN124 and HN159 patient-derived xenografts. Error bars indicate one standard deviation. Asterisks denote significance by student t-test (*-p<0.05, -p<0.01, *-p<0.001).
Figure 9:
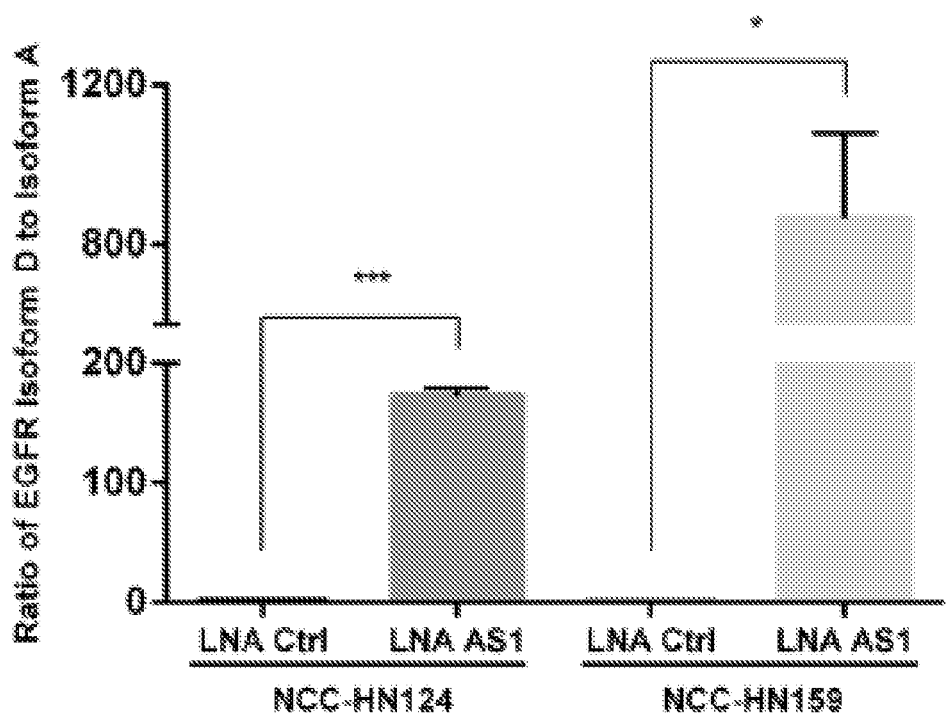

In silico analyses showed no potential miRNA targeting sites that could affect EGFR mRNA transcription or translation (data not shown). However, it was found that this described SNP was within the transcribed portion of the EGFR-AS1 lncRNA (FIG. 2A). Real-time RT-PCR showed that transcript levels of EGFR-AS1 lncRNA were significantly higher in the resistant lines with the G/G genotype (NCC-HN1 and NCC-HN43), compared to the sensitive A/A genotype (NCC-HN19 and NCC-HN64; FIG. 2B). Similar findings were seen in the NCC-HN1 isogenic clones: lower EGFR-AS1 transcript levels in G/A$^{AAV}$ compared to control G/G$^{AAV}$ clones. Using Actinomycin D to block transcription, it was next demonstrated that the EGFR-AS1 lncRNA transcript was more stable in lines with the G/G genotype compared to the A/A genotype, which was recapitulated in the isogenic NCC-HN1 clones with genotype switch (FIG. 2C). Finally, knockdown of EGFR-AS1 (FIG. 9) was shown to be sufficient to significantly increase sensitivity of G/G cell lines to gefitinib, with reduction in mean IC$_{50}$ values from 8.9 to 2.3 µM for NCC-HN1 and from 9.6 to 2.8 µM for NCC-HN43 (FIG. 2D). To test if EGFR-AS1 was a bona fide driver, it was determined whether tumours with G/A or G/G genotype were dependent on the lncRNA levels by in vivo knock-down in a patient-derived xenograft (PDX) system. A panel of locked nucleic acid (LNA) against EGFR-AS1 was designed and the most effective candidate selected through in vitro screens for effective knock-down (data not shown). In vivo grade version of this AS1-targeting LNA and control non-targeting LNA were subsequently injected (weekly dose of 5 mg/kg) into the tail veins of NOD-scid-gamma (NSG) mice harbouring patient-derived xenografts of a tumour (HN124) with G/A Q787Q genotype and high AS1 levels (FIG. 4B). After one week of LNA-only treatment, mice were started on daily gefitinib doses (25 mg/kg) for the rest of the experiment. Successful knock-down of AS1 levels was seen in patient-derived xenografts one week after treatment with AS1-targeting LNA compared to non-targeting controls (FIG. 8). AS1-knockdown in vivo was sufficient to cause tumour regression even before gefitinib was initiated, but this regression was sustained after treatment, compared to controls where neither control LNA nor gefitinib showed any effect (FIG. 2E). The same experiment was repeated in a different patient-derived xenograft (HN159-G/G genotype, high AS1 levels), this time omitting the gefitinib treatment. Again, it was shown that mice treated with AS1-targeting LNA (with successful knockdown) resulted in sustained tumour regression compared to controls, demonstrating tumour addiction to the lncRNA.

Figure 3A:
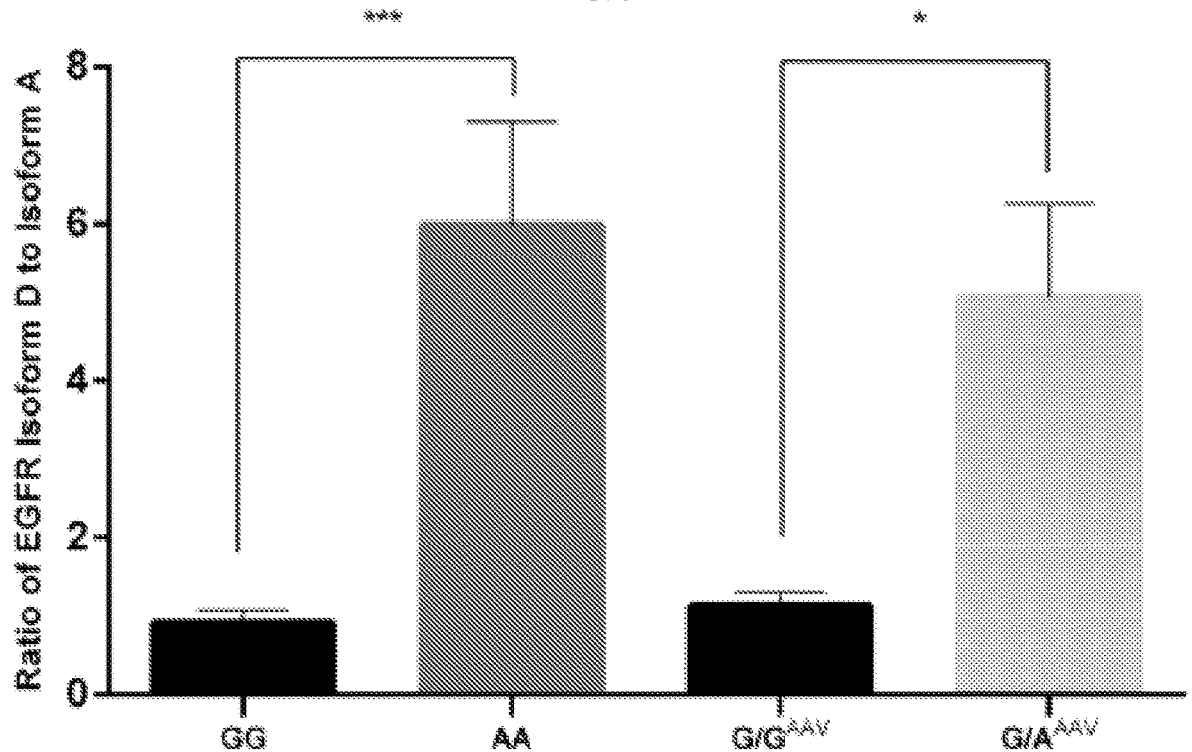
FIG. 3A is a bar graph showing ratio of EGFR isoform D to A transcripts measured by real-time RT-PCR in the different lines and targeted NCC-HN1 (G/A$^{AAV}$) clones, with Q787Q genotype as indicated. Error bars indicate one standard deviation. Asterisks denote significance by student t-test (*–p<0.05, –p<0.01, *–p<0.001).
Figure 3B:
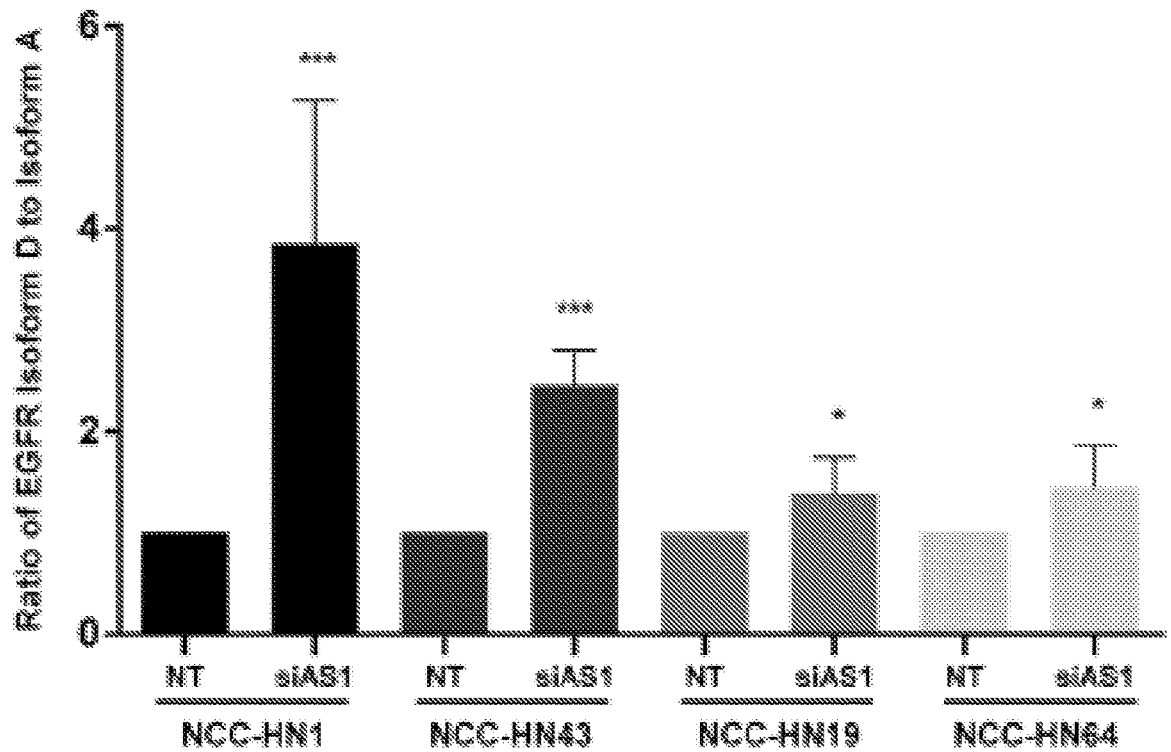
FIG. 3B is a bar graph showing ratio of EGFR isoform D to A transcripts measured by real-time RT-PCR after knockdown of EGFR-AS1 (siAS1) compared to non-targeted controls (NT). Error bars indicate one standard deviation. Asterisks denote significance by student t-test (*–p<0.05, –p<0.01, *–p<0.001).
Figure 10:
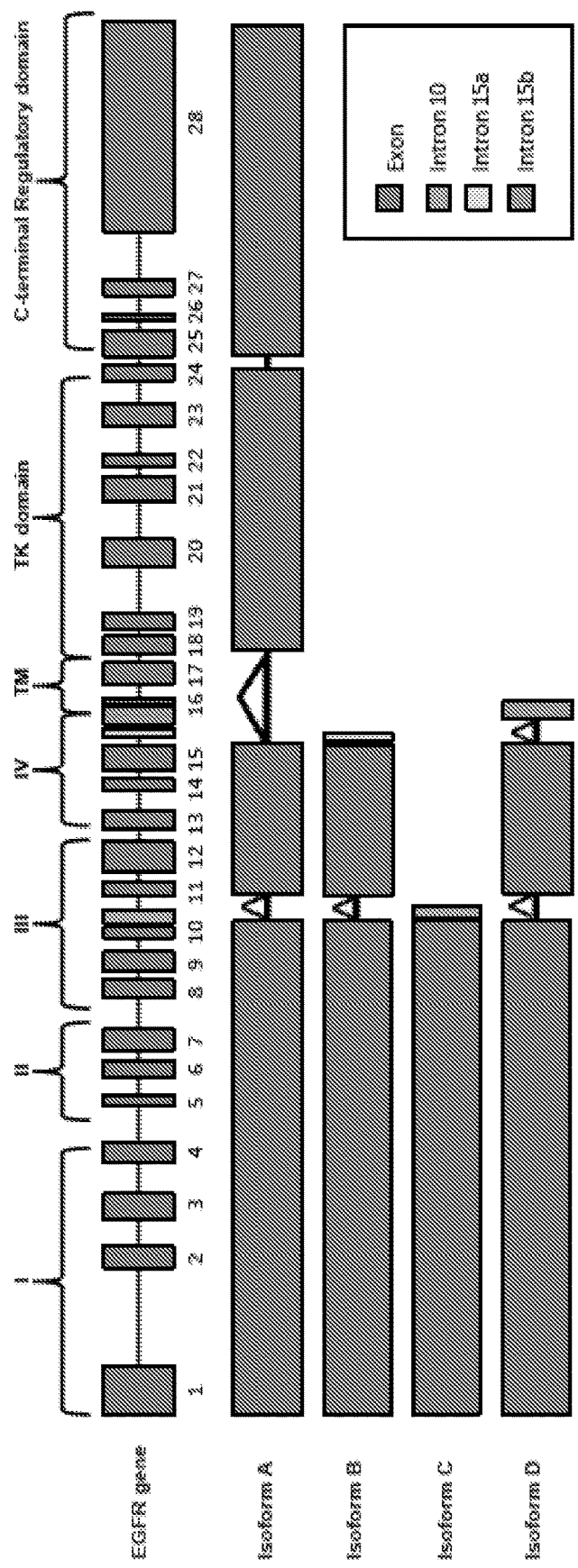
FIG. 10 is an alternative splice diagram of the EGFR gene showing the four commonly described isoforms (A, B, C, and D) and the relevant exons.
Figure 11:
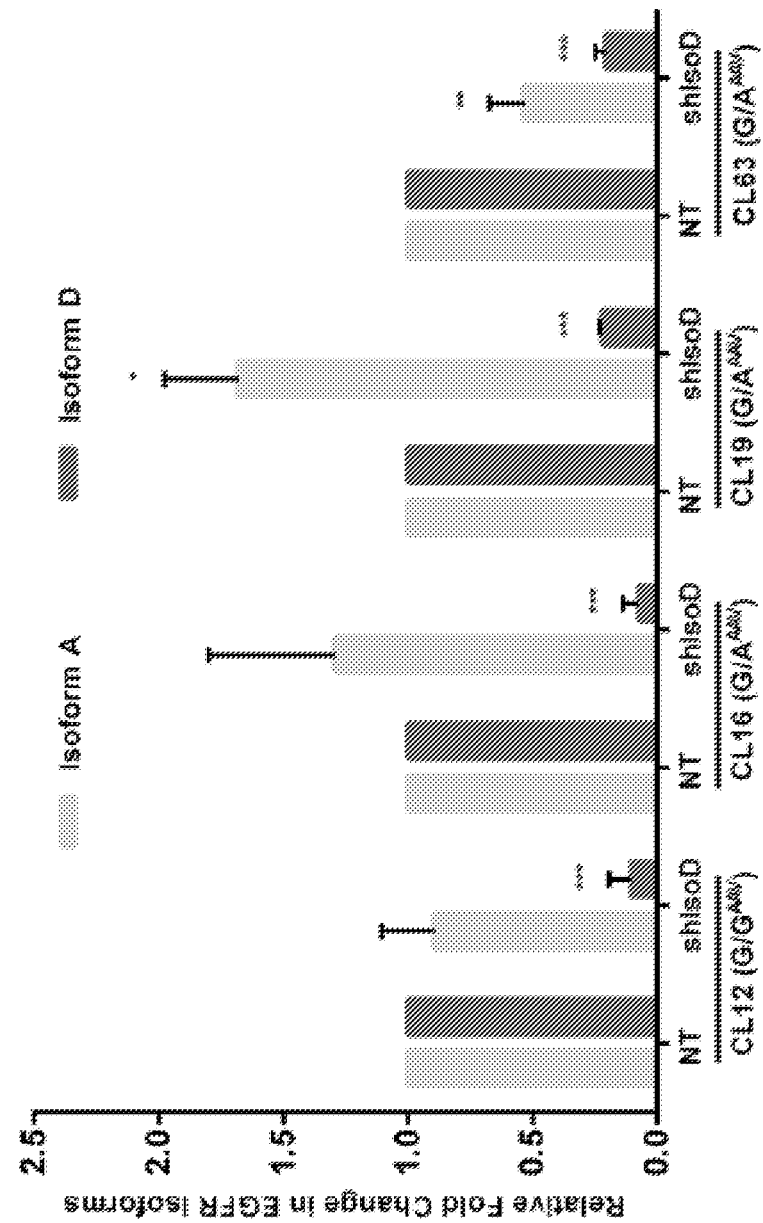
FIG. 11 is a bar graph showing the relative fold change in levels of the EGFR isoform A and D transcripts, as measured by real-time RT-PCR after knockdown of isoform D with targeted shRNA (shIsoD, also referred to as shEGFR4) compared to non-targeting controls (NT) in cell lines and isogenic NCC-HN1 clones. Error bars indicate one standard deviation. Asterisks denote significance by student t-test (*-p<0.05, -p<0.01, *-p<0.001).

EGFR Tyrosine Kinase Inhibitor Sensitivity Mediated Through Differential Expression of EGFR Isoforms Given that the lncRNA had no effect on transcript, protein stability, or results in aberrant splicing of EGFR (data not shown), it was proceeded to examine the effect on expression levels of the four known EGFR isoforms (A-D) (FIG. 10). Real-time PCR showed that there was a higher ratio of isoform D:A transcript levels in both lines with the A/A genotype (NCC-HN19 and NCC-HN64), compared to the lines with the G/G genotype (NCC-HN1 and NCC-HN43; FIG. 3A). These results were recapitulated in the NCC-HN1 genotype switched G/A$^{AAV}$ clones. Moreover, targeted knock-down of the EGFR-AS1 lncRNA was sufficient to increase isoform D:A ratio in all lines examined, although this was more dramatic in the G/G genotype (NCC-HN1 and NCC-HN43) (FIG. 3B). The same effect of increase in isoform D:A ratio was also seen in vivo with LNA-mediated knockdown of EGFR-AS1 in the two patient-derived xenografts (HN124 and HN159; FIG. 8). Next, it was determined whether isoform D expression was necessary for EGFR sensitivity. Using the unique sequence of exon 16B, isoform D specific targeting shRNAs were designed. Stable transfectants in NCC-HN19, NCC-HN64, NCC-HN1 and NCC-HN43 showed specific targeting of isoform D but not isoform A (FIG. 11).

Figure 3C:
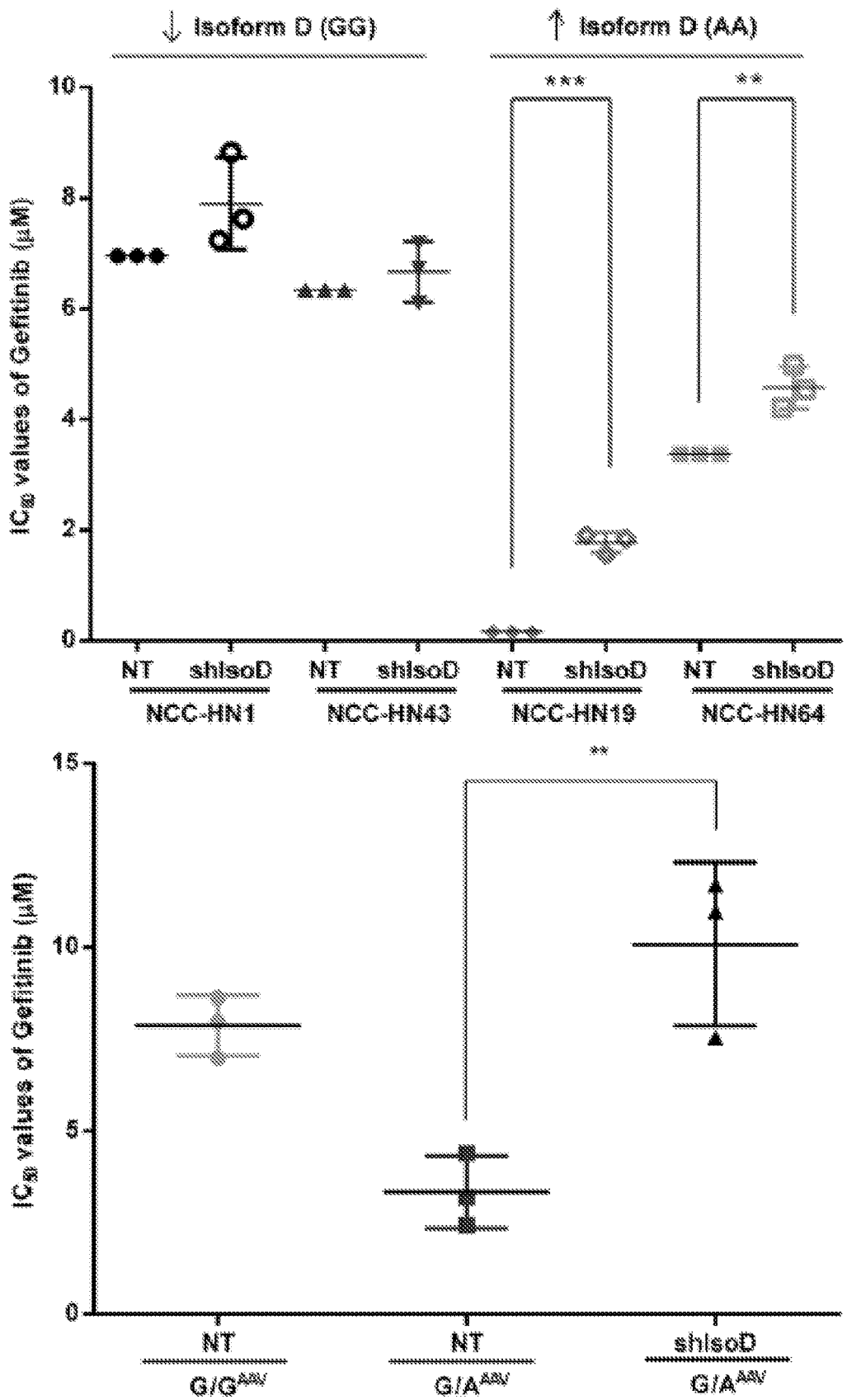
FIG. 3C is a set of graphs showing $IC_{50}$ values of the different HNSCC cell lines and NCC-HN1 clones (G/A$^{AAV}$ and G/G$^{AAV}$; genotypes as indicated) after successful isoform D knockdown (shIsoD) compared to non-targeted controls (NT) treated with gefitinib. Error bars indicate one standard deviation. Asterisks denote significance by student t-test (*–p<0.05, –p<0.01, *–p<0.001).
Figure 3D:
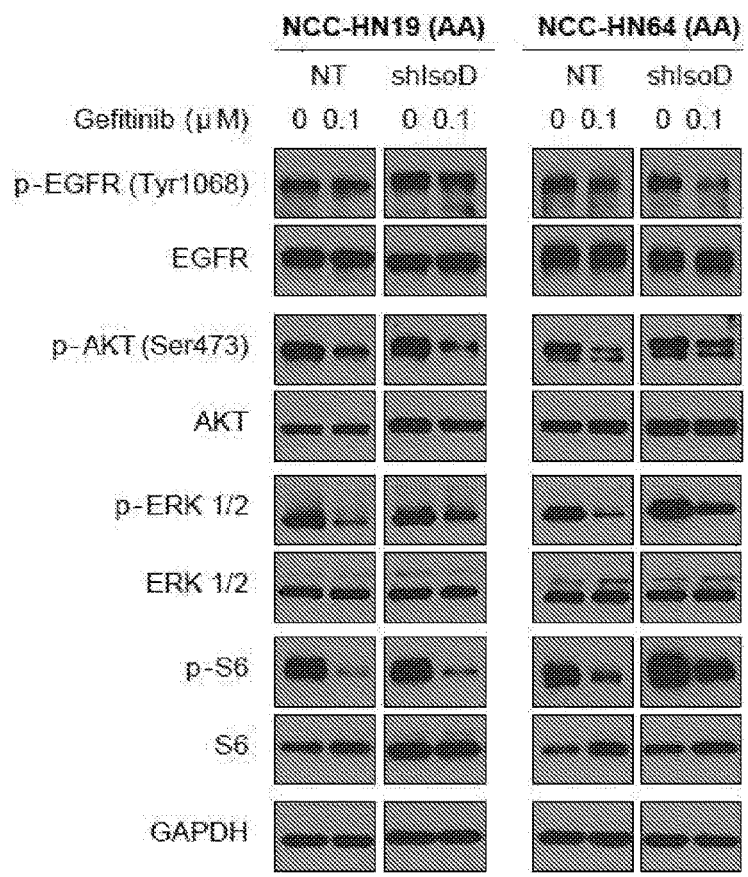
FIG. 3D is a set of images showing western blot results of the EGFR pathway activation after treatment with gefitinib after isoform D knockdown (shIsoD), compared to non-targeting controls. GAPDH is used here as a loading control.
Figure 3E:
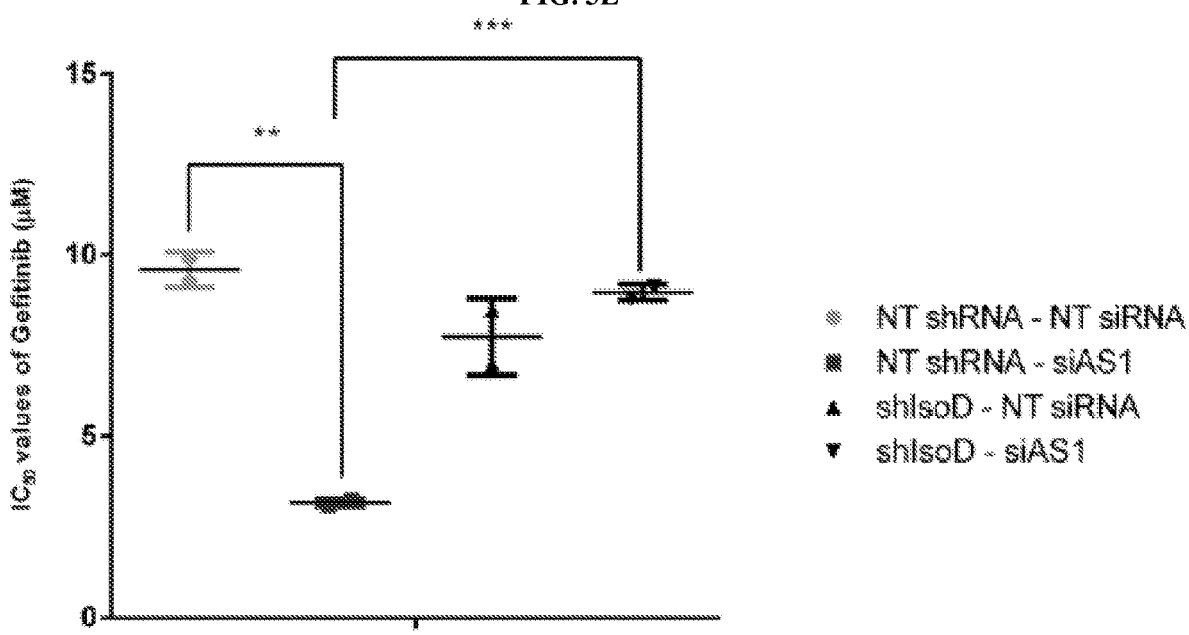
FIG. 3E is a graph showing $IC_{50}$ values of the different HNSCC cell lines and NCC-HN1 clones (G/A$^{AAV}$ and G/G$^{AAV}$; genotypes as indicated) after successful isoform D knockdown (shIsoD), with additional knockdown of EGFR-AS1 (siAS1). The clones being referred to herein are CL16 and CL19 (G/A$^{AAV}$) and negative controls CL12 and CL77 (G/G$^{AAV}$). Error bars indicate one standard deviation. Asterisks denote significance by student t-test (*–p<0.05, –p<0.01, *–p<0.001).
Figure 3F:
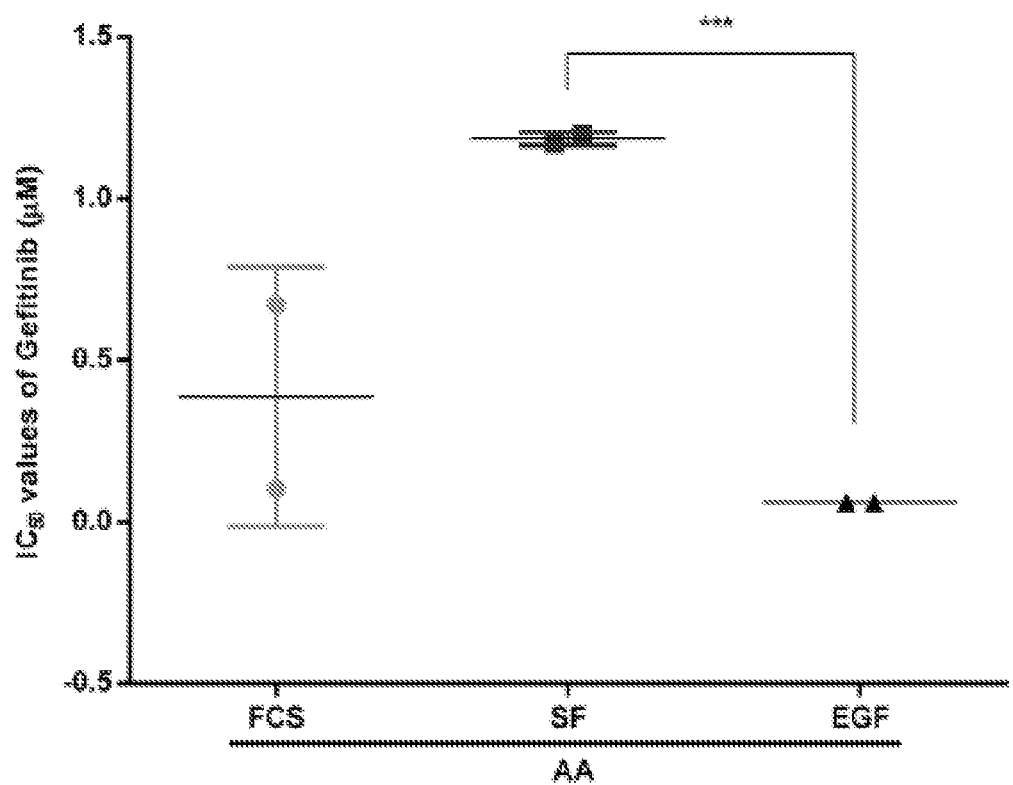
FIG. 3F is a set of graphs showing $IC_{50}$ values for the AA cell lines (NCC-HN19 and NCC-HN64) and G/A HN1 clones treated with gefitinib in RPMI with serum (FCS), serum-free (SF), or serum-free but with added EGF (EGF). Error bars indicate one standard deviation. Asterisks denote significance by student t-test (*–p<0.05, –p<0.01, *–p<0.001).
Figure 3F:
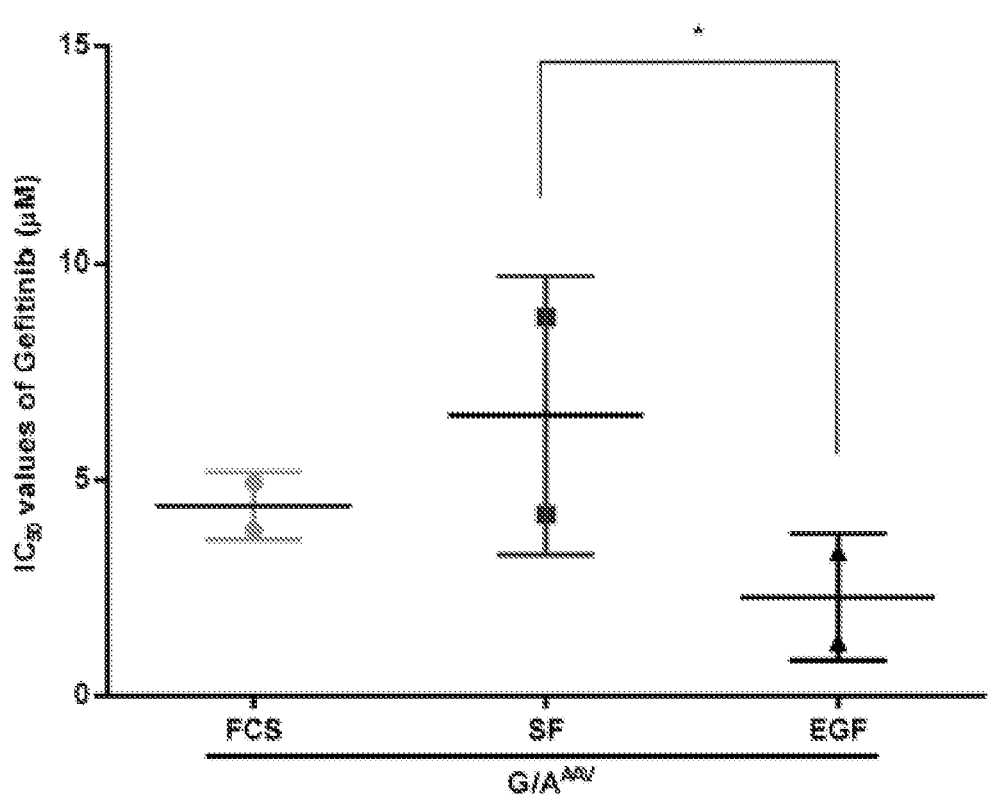

In these models, previously gefitinib-sensitive NCC-HN19 and NCC-HN64 (A/A) were rendered more resistant (FIG. 3C), with no significant effect on the G/G genotype lines (NCC-HN1 and NCC-HN43). Similarly, targeting isoform D in the genotype switched G/A$^{AAV}$ clones showed reduced sensitivity, while having no effect on negative controls. Relative to non-targeting controls, reduced expression of isoform D also attenuated the impact of gefitinib on downstream pathway modulation in the HNSCC cell lines with the AA-genotype (FIG. 3D). Importantly, the effect of EGFR-AS1 knock-down promoting gefitinib sensitivity was abrogated by concurrent isoform D knockdown in the cell lines with the G/G genotype (FIG. 3E). In order to determine whether sensitivity to gefitinib was ligand-dependent, cell lines were cultured in normal media with serum, serum-free media and media supplemented with epidermal growth factor (EGF), and treated with gefitinib. IC$_{50}$ values in cell lines with the A/A genotype and genotype switched G/A$^{AAV}$ clones were significantly lower in serum- and EGF-enriched media, compared to serum-free conditions (FIG. 3F). This data confirms that the effect of the EGFR-AS1 lncRNA is mediated through alteration of the EGFR isoforms A and D, and this effect is likely ligand dependent.

EGFR-AS1 Levels and Isoform D:A Ratio Determine Gefitinib Response

Figure 4A:
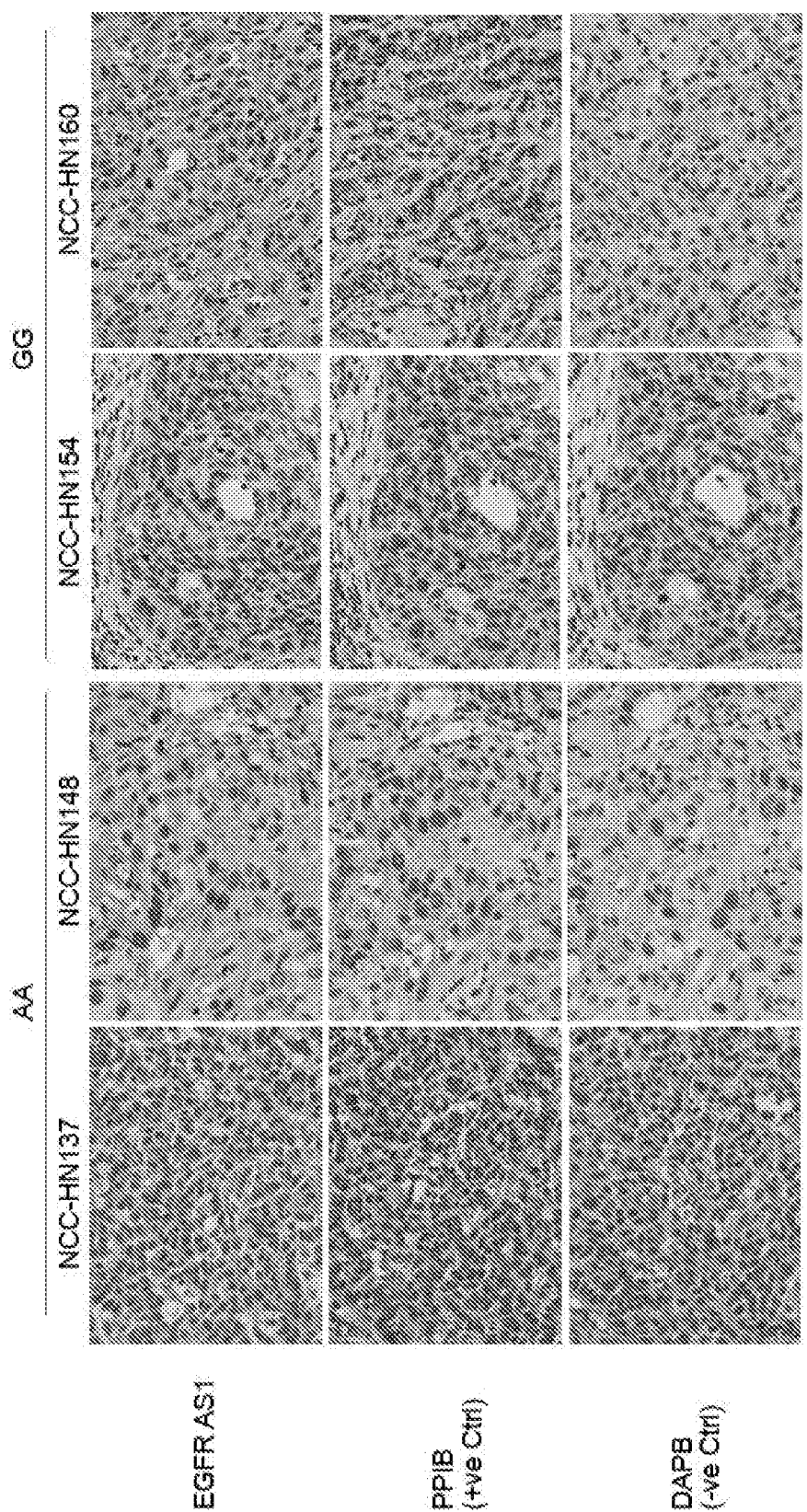
FIG. 4A is a set of photographs showing the result of RNA-in situ hybridization using RNAscope showing levels of AS1, EGFR isoform A and D in two tumour specimen which have a A/A and G/G genotypes. PPIB is the positive control and DAPB is the negative control.
Figure 4C:
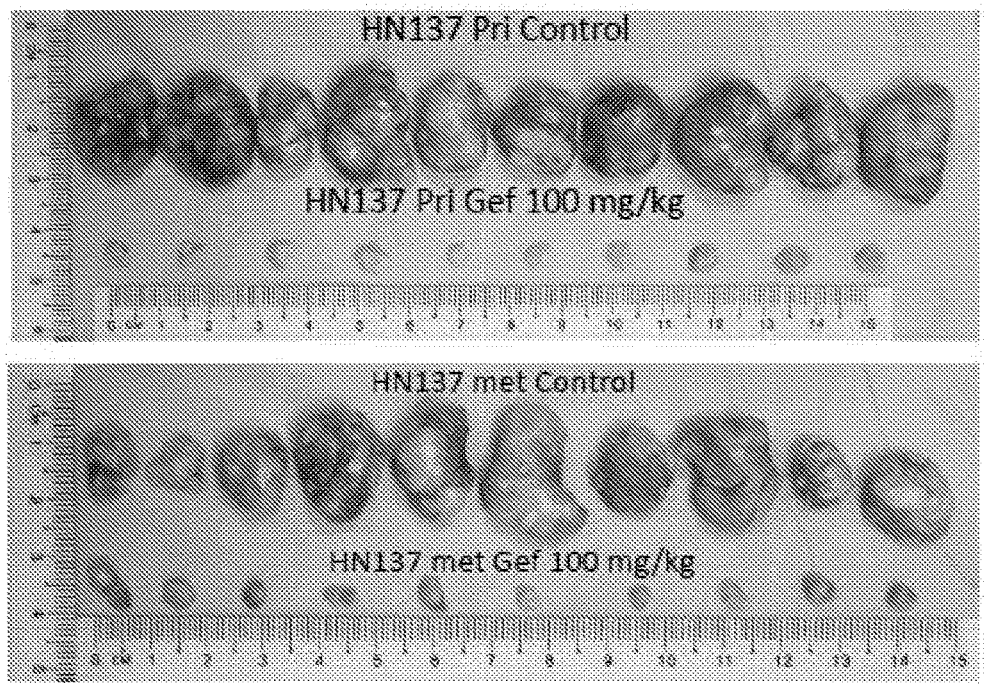
FIG. 4C is a set of photographs and a line graph showing patient-derived xenograft models for HN137 primary (pri) and metastatic (met) tumours treated with control or gefitinib. The arrow on the line graph indicates when treatment was initiated.
Figure 4C:
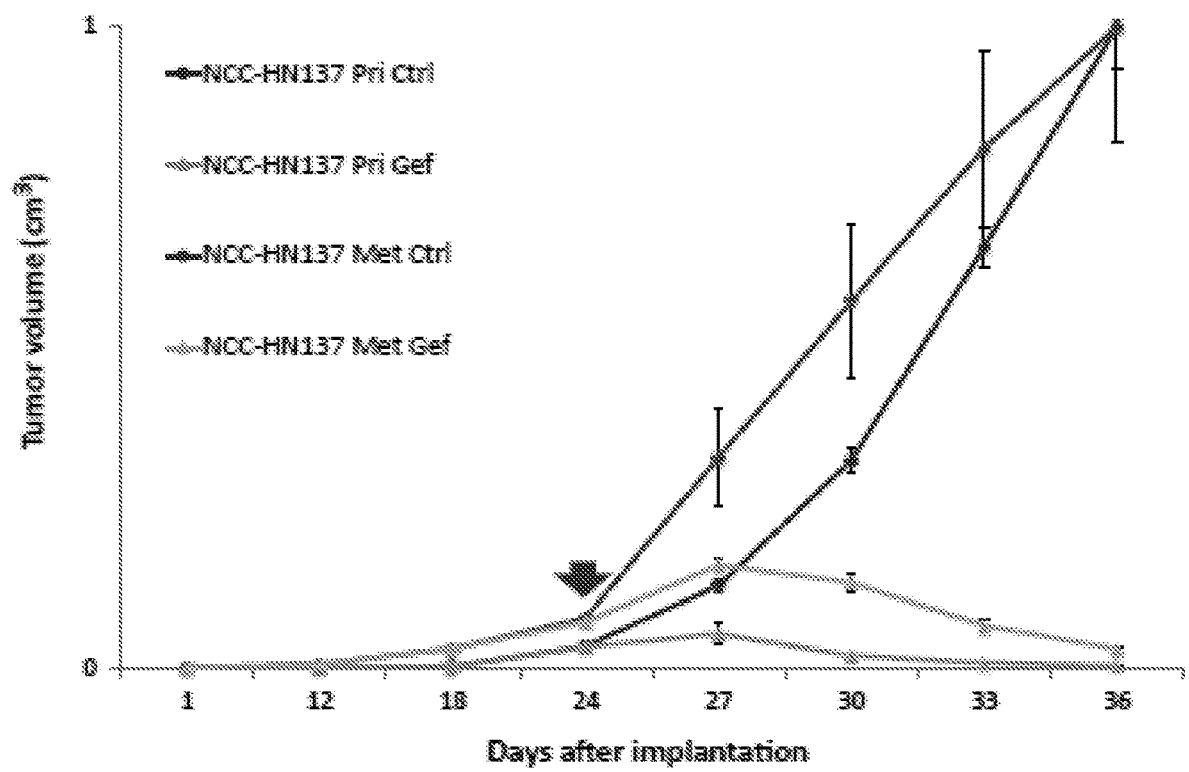
Figure 4D:
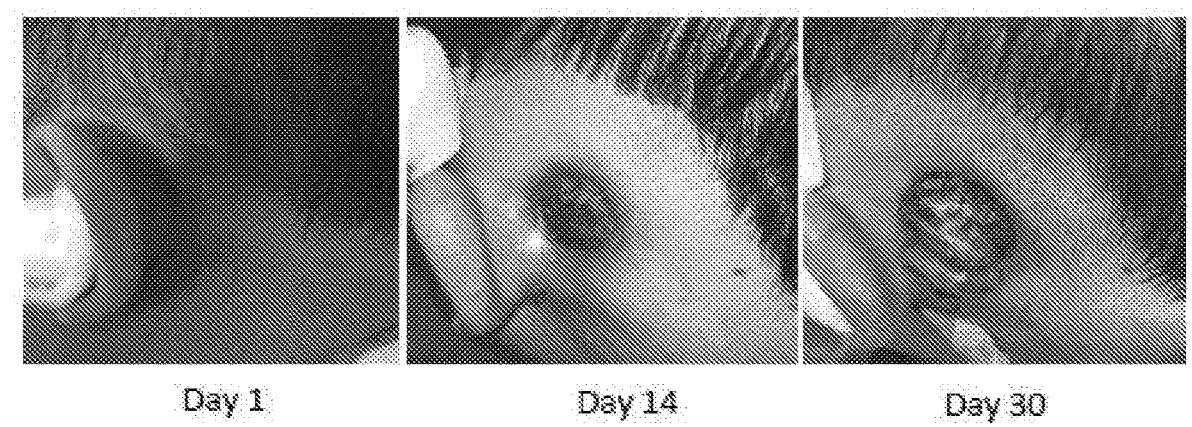
FIG. 4D is a set of clinical and CT-scan images showing response of patient HN137 to gefitinib treatment. Arrows indicate location of lung metastasis that subsequently responded to treatment.
Figure 4D:
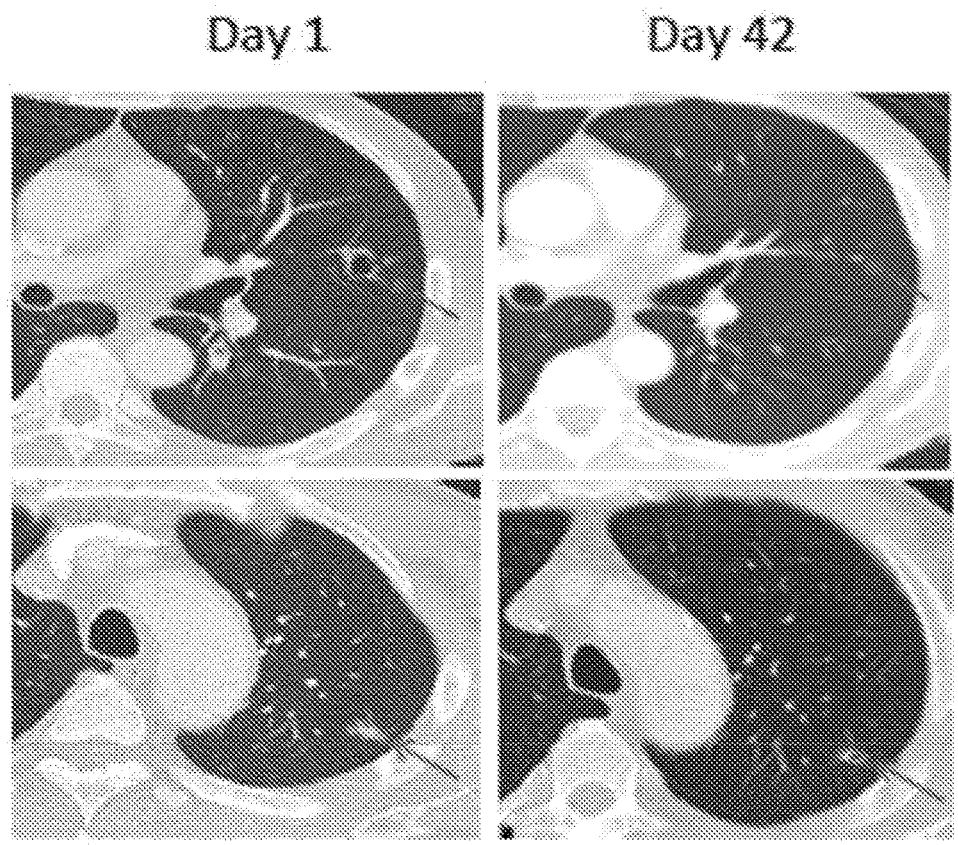

To evaluate potential biomarkers, semi-quantitative assessment of AS1(1+ or 0) (FIG. 4A) and relative EGFR isoform A and D levels in primary tumour tissue using RNA-in situ hybridization using RNAscope technology and real-time PCR, respectively, was performed. In A/A genotype, AS1 was not detected with increased isoform D/A ratio. Conversely, in either G/A or G/G genotypes, AS1 levels were high (1+), with low isoform D/A ratios. Where available, IC$_{50}$ values for patient-derived tumour lines were consistent with both genotype statuses, AS1 levels and isoform D/A ratios (FIG. 4B). From this cohort, one patient presented with recurrent, metastatic disease, and hence amenable to a co-clinical trial under IMPACT-SG. This patient (HN137) was initially diagnosed with T4N2BM0 oral squamous cell cancer and underwent surgery followed by adjuvant chemo-radiation therapy. He subsequently developed dermal and lung metastases six months after adjuvant therapy. Sequencing confirmed the A/A genotype for Q787Q, and real-time PCR showed low EGFR-AS1 levels and high EGFR isoform D:A ratio in his original primary and metastatic tumour compared to controls (FIG. 4B). Both original and metastatic tumours had been engrafted as patient derived xenografts (PDXs), and these were expanded and a clinical trial using oral gefitinib (50 mg/kg by oral gavage) was conducted in NSG mice. Both primary and metastatic patient derived xenograft tumours showed significant tumour regression when treated with gefitinib, compared to untreated controls (FIG. 4C). The patient was concurrently initiated on a 250 mg daily dose of gefitinib; clinical and radiological assessment showed significant regression of dermal and lung metastases after six weeks of gefitinib monotherapy (FIG. 4D).

Despite the availability of FDA-approved EGFR targeting therapies in squamous cell carcinoma of head and neck and lung origin, no robust predictive biomarkers have been established. Reported here is a mechanism of EGFR addiction mediated by an lncRNA EGFR-AS1. It is also further demonstrated how a synonymous single nucleotide variant can mediate EGFR tyrosine kinase inhibitor sensitivity through modulation of the lncRNA EGFR-AS1, with consequent increase in isoform D:A ratios, resulting in ligand-driven EGFR-dependency. This is supported by three patients with EGFR wild type oral squamous cell cancer, who were exceptional responders to gefitinib, all of whom were A/A genotype. To date, majority of predictive biomarkers in cancer are genomic based and largely confined to non-synonymous mutations that alter protein structure and function. Without being bound by theory, this report describes how a "silent" SNP can impact on lncRNA levels, with dramatic effect on vulnerability to EGFR inhibitors. Further depicted is a possible roadmap for EGFR activation, defining a comprehensive biomarker suite to precisely predict which patients might respond to EGFR tyrosine kinase inhibitors.

Several recent studies have also identified lncRNAs critical to tumourigenesis, and suggest that these may be targeted with therapeutic intent. Without being bound by theory, the data shown herein points to a critical role to an exon 20 SNP that results in a single nucleotide variant within the lncRNA, that influences the stability of EGFR-AS1—possibly due to changes in higher order structure. One consequence is a cis-mediated effect on alternative splicing of EGFR, with increased isoform D:A ratio. Certainly, the localization of EGFR-AS1 transcripts in the nucleus lends geographic support to this effect (seen by RNA in situ hybridisation; FIG. 4A), where it can affect transcription and/or pre-mRNA processing.

Manipulating the genotype from AA to GA, or reducing the levels of AS-1 lncRNA was sufficient to increase sensitivity to EGFR tyrosine kinase inhibitors in a consistent and predictable manner, and this effect could be abrogated by knockdown of EGFR isoform D, which is likely the effector of this phenotype.

Naturally occurring EGFR isoforms have been poorly studied to date, with a few studies suggesting that alternate isoforms are secreted in plasma (as secreted EGFR or sEGFR) and may be prognostic in lung and cervical cancers. Analysis of sEGFR levels in non-small cell lung cancer patients treated with erlotinib supported the notion that higher levels of sEGFR was predictive of tyrosine kinase inhibitor response, although no distinction was made between the particular isoform measured. The relative increase in isoform D that lacks the tyrosine kinase domain seen here, over full length isoform A, as well as the requirement for ligand-driven EGFR activation, suggests a mechanism involving the extra-cellular domain region, for example, receptor dimerization. While the lack of specific antibodies for each EGFR isoform imposes limitations on spatial localisation and quantification, analysis of mRNA transcripts is a viable alternative as shown here using real-time RT-PCR or RNAscope. Notwithstanding, the precise mechanism through which EGFR-AS1 augments alternative splicing to result in high isoform D:A ratios, remains unclear.

There are several important implications to the data disclosed herein. Notably, the prevalence of this SNP (homozygous A/A genotype) is 4% in the Asian context (as examined herein) but 30% in Caucasian populations (http://exac.broadinstitute.org), highlighting important geographical disparities of genomic biomarkers. Furthermore, the biomarker roadmap for EGFR pathway activation—starting with genotype, levels of EGFR-AS1 lncRNA, relative EGFR isoform expression, and ligand expression—has been established, thereby underscoring the need to establish multi-dimensional biomarker suites for high precision patient enrichment strategies. Also, the ability for "silent" synonymous alterations to influence EGFR addiction opens new avenues to discover novel biomarkers of existing targeted therapies, with enormous potential for immediate re-purposing and clinical impact.

Finally, the lncRNA EGFR-AS1 has been demonstrated as a bona fide driver of EGFR addiction, and represents a novel therapeutic target in a subset of squamous cell cancers, potentially through RNAi based strategies that have entered clinical testing.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Experimental Section

Tumour Specimens and Primary Cell Cultures

Patient-derived tumours were collected and processed as previously described (Leong H S, et al. Stem Cells Translational Medicine 2014; 3:1055-65). All lines were cultured in RPMI media (Sigma Aldrich, St. Louis, Mo.) supplemented with 10% fetal bovine serum (FBS) (Hyclone, Thermo Scientific Inc., Fremont, Calif.) and 1% Penicillin-Streptomycin (Life Technologies, Amsterdam, Netherlands) in a humidified atmosphere of 5% $CO_2$ at 37° C. Details of cell line origin and clinico-pathologic characteristics of the patient they were derived from are outlined in FIG. 12. Cell line identity was authenticated by targeted sequencing of the line and primary tumour, to determine identical SNPs, with significant mutations shown in FIG. 13.

Cell Proliferation Assay and Determination of $IC_{50}$ Values

Cells were seeded in 100 µl complete growth medium at a density of 2,000-4,000 cells/well in 96-well tissue culture plates. After serial dilutions, 100 µl of complete growth medium containing Gefitinib or Erlotinib (BioVision, Milpitas, Calif.) were added to cells. DMSO was used as controls. Plates were incubated for 48 hours after which cell viability was assessed using CellTitre-Glo® Luminescent Assay according to the manufacturer s protocol (Promega, Madison, Wis.).

Inhibition of RNA Replication

Cells were starved in serum free media for 24 hours. A final concentration of 5 µg/ml of Actinomycin D (Sigma Aldrich, St. Louis, Mo.), dissolved in dimethyl sulfoxide, was added with fresh serum free media and cells were harvested at 0 hours, 1 hours, 2 hours, and 4 hours intervals.

Mutational Analysis

Total genomic DNA was extracted from primary cell lines using QIAamp DNA Mini kit according to the manufacturer s instructions (Qiagen, Valencia, Calif.). 10 ng of DNA was used to run the Ion AmpliSeq Colon and Lung Cancer Panel v1 (Life Technologies, Amsterdam, Netherlands) on the Ion Torrent platform (Life Technologies, Amsterdam, Netherlands). The Panel consists of primer pairs targeting hotspots in 22 known genes implicated in colon and lung cancer. The 22 genes are KRAS, EGFR, BRAF, PIK3CA, AKT1, ERBB2, PTEN, NRAS, STK11, MAP2K1, ALK, DDR2, CTNNB1, MET, TP53, SMAD4, FBX7, FGFR3, NOTCH1, ERBB4, FGFR1, FGFR2.

rAAV Production

In primary patient-derived cell lines, targeted knock-in of the Q787Z genotype in for example NCC-HN1cell line was performed using the Horizon AAV system (Horizon Discovery Group, Cambridge, UK). $1 \times 10^6$ HEK293 cells were seeded in 100 mm dishes 24 hours prior to transfection in DMEM (Sigma Aldrich, St. Louis, Mo.) with 10% fetal bovine serum, 1% Penicillin-Streptomycin in a 5% $CO_2$ incubator. The pAAV EGFR(G or A) transfer vector (Horizon Discovery Group, Cambridge, UK) was co-transfected with pAAV-RC and pHelper plasmids (10 µg of each) from the AAV Helper-Free System (Stratagene, La Jolla, Calif.) using Lipofectamine 2000 (Life Technologies, Amsterdam, Netherlands) according to manufacturer s instruction. The virus was harvested 48 hours after transfection in accordance with the manufacturer s protocol. In brief, the media was aspirated from the flask together with HEK293 cells, and subjected to three freeze and thaw cycles. The lysate was clarified by centrifugation at 13,000 rpm at 4° C. to remove cell debris, and the supernatant containing rAAV was divided into aliquots and frozen at −80° C. for subsequent use.

Viral Infection and Screening for Recombinants

Cells were grown in 100 mm dishes until 70-80% confluence. After removing existing media, 200 µl of rAAV lysate and 4 ml of Opti-MEM media (Life Technologies, Amsterdam, Netherlands) were added to the cells. The virus was allowed to infect cells at 37° C. for 4 hours after which the media was replaced with 5 ml fresh media. Infected cells were allowed to grow for 48 hours and then harvested by trypsinization, and distributed into twelve 96-well plates with media containing Geneticin (Life Technologies, Amsterdam, Netherlands). Plates were incubated at 37° C. for 2 to 3 weeks prior to harvest and screening for recombinant events. To verify successful integration of the Horizon vector into the EGFR gene at the expected site, primers flanking part of the Neomycin open reading frame that is present in the vector and Intron 20 of the EGFR were designed as presented in FIG. 6. PCR using genomic DNA was performed as previously described (Zhao Y, et al. Oncogene 2008; 27:1-8).

Lentivirus shRNA Knockdown

In primary patient-derived cell lines, targeted knockdowns of the Q787Z genotype in cell line, for example NCC-HN1, were performed using shRNA lentiviral system (Sigma Aldrich, St. Louis, Mo.). Cells were seeded with density of $1 \times 10^5$ in a 6-well tissue culture plate 24 hours prior infection. The media was removed and the cells were infected with 1 MOI (multiplicity of infection) of pLKO. 1-EGFR Isoform D-puro Lentiviral particles (Sigma Aldrich, St. Louis, Mo.) and 4 ml of Opti-MEM media were added to the cells. Lentival pLKO.1-puro empty vector control transduction particles were used as controls. The virus was allowed to infect cells at 37° C. for 4 hours and replaced with 5 ml fresh media. Infected cells were allowed to grow for 48 hours and then selected with Puromycin-containing media (Life Technologies, Amsterdam, Netherlands).

DNA, RNA and Protein Analysis

Genomic DNA extraction and PCR/sequencing were performed as previously described (Zhao Y, et al. Oncogene 2008; 27:1-8). Real-time PCR of genomic DNA and cDNA was performed using iTaq Universal SYBR Green Supermix (Bio-Rad Laboratories, Hercules, Calif.) and a CFX96 Real-time PCR system (Bio-Rad Laboratories, Hercules, Calif.) according to the manufacturer s instructions. Reactions were carried out in triplicate with Actin served as the normalizing control. Primer sequences used are presented in Table 1 and Sanger sequencing was used to confirm identity of all transcripts. SDS-PAGE Western blotting was performed as previously described (Leong H S, et al. Stem Cells Translational Medicine 2014; 3: 1055-65 and Zhao Y, et al. Oncogene 2008; 27:1-8). Antibodies used were as follow: rabbit polyclonal antibodies to EGFR, phosphor-EGFR (Tyr 1068), AKT, phosphor-AKT (Ser 473), Erk 1/2, phosphor-Erk 1/2 (Thr 202/204), S6, phosphor-S6 (Ser 235/236) (Cell Signalling Technology, Danvers, Mass.) and GAPDH (Cell Signalling Technology, Danvers, Mass.). Total RNA extraction and reverse transcription was performed as previously described (Zhao Y, et al. Oncogene 2008; 27:1-8).

RNA In Situ Hybridization (ISH) Using RNAscope

In situ hybridization for EGFR AS1 was performed using the RNAscope 2.0 FFPE Assay according to the manufacturer s protocols (Advanced Cell Diagnostics, Hayward, DA). 5 µm patient-derived formalin fixed paraffin embedded (FFPE) sections were sent to Singapore Health Services Pte. Ltd. to perform the RNA in situ hybridization. Positive staining was observed as brown, punctate dots. A positive control probe, *Homo sapiens* peptidylprolyl isomerase B (PPIB), and a negative control probe for the bacterial gene DapB (DAPB) were performed for each tissue sample.

Patient-Derived Xenograft (PDX) and Treatment Studies

Primary and metastatic tumour tissue were placed in DMEM/F-12 medium and cut into small pieces (diameter 0.8 mm to 1.5 mm) using dissection scissors. These were mixed with 20% Matrigel (Corning, Tewksbury, Mass.) and subcutaneously injected into the flanks of male NOD-scid gamma (NSG) mouse (NOD.Cg-Prkdc$^{scid}$ Il2rg$^{tm1Wjl}$/SzJ; 005557; Jackson Laboratory, Bar Harbor, Me.). When tumour size reached 1.5 cm$^3$, tumours were harvested, processed and re-injected for expansion (passage 1 or P1).

This process was repeated to expand the tumour tissue. For the co-clinical trial, the P4 passage was used. Gefitinib (Iressa) (AstraZeneca, London, UK) was prepared by dissolving a 250 mg clinical grade tablet in sterile water containing 0.05% Tween-80 (Sigma Aldrich, St. Louis, Mo.) to a concentration of 20 mg/ml. When tumours reached 0.5 $cm^3$ in size (24 days for HN137 met and 12 days for HN137 pri), mice were started on treatment with 100 mg/kg Gefitinib or controls with the same amount of 0.05% tween-80 in water. Tumour size was measured with a calliper once every 3 days. 12 days post treatment with Gefitinib (n=5 mice), when the tumours size of treated group reached 2.0 $cm^3$, the mice were euthanized and analysed.

In Vivo Locked Nucleic Acid (LNA) Treatment

In vivo EGFR-AS1 knockdown was performed using custom locked nucleic acid (LNA) oligonucleotide (Exiqon, Vedbaek, Denmark). Treatments with custom LNA oligonucleotides were performed according to the manufacturer's protocol. The custom sequence of the LNA (15-mer RNA/LNA oligonucleotide) against EGFR-AS1 (LNA-AS1) used was ATCGCAAAGGTAATC (SEQ ID NO: 25). Negative control LNA 15-mer oligonucleotide (LNA-i-miR-NC) sequence was AACACGTCTATACGC (SEQ ID NO: 26). Both oligonucleotides contain phosphorothioate backbone modifications and were purified by HPLC followed by $Na^+$ salt exchange and lyophilisation for in vivo use. Selected patient-derived xenografts were passaged, and when tumour growth was deemed to reach a size of 0.5 $cm^3$, LNA treatment was initiated. LNA treatment was delivered as weekly tail vein injections of 5 mg/kg, and after the first week of treatment, one mice from the experimental and control arms were sacrificed to confirm knock-down. Treatment was stopped when the tumours in the experimental arm were unmeasurable or when tumours in the control arms exceeded 2.0 $cm^3$.

Study Conduct

The study and protocols for tissue collection for cell line/patient-derived xenograft propagation have been approved by the Singhealth Centralized Institutional Review Board (CIRB 2007/441/B). The co-clinical trial in a patient with oral squamous cell cancer (OSCC) and the corresponding patient-derived xenograft implanted to a NSG mouse was initiated under the IMPACT-SG (Individualized Molecular Profiling for Allocation of Clinical Trials) (CIRB 2011/441/B).

TABLES

TABLE 1

Table of sequences

| SEQ ID NO | Target/ description | Primer | Sequence 5'-3' | Amplicon size (bp), if applicable |
|---|---|---|---|---|
| 1 | EGFR | Forward | CTGAGGTGACCCTTGTCTCTGTGTTCTT | 186 |
| 2 | Exon 18 | Reverse | AGAGGCCTGTGCCAGGGACCTTA | |
| 3 | EGFR | Forward | TCACTGGGCAGCATGTGGCA | 241 |
| 4 | Exon 19 | Reverse | CAGCTGCCAGACATGAGAAA | |
| 5 | EGFR | Forward | CCATGCGAAGCCACACTGA | 248 |
| 6 | Exon 20 | Reverse | CGTATCTCCCTTCCCTGATTACC | |
| 7 | EGFR | Forward | AGCAGGGTCTTCTCTGTTTCA | 200 |
| 8 | Exon 21 | Reverse | TGACCTAAAGCCACCTCCTT | |
| 9 | EGFR VIII | Forward | GGGCTCTGGAGGAAAAGAAA | 952 |
| 10 | | Reverse | ATTCCGTTACACACTTTGCGGC | |
| 11 | Neo ORF | Forward | CTGGCTGCTATTGGGCGAAG | 2131 |
| 12 | | Reverse | TGCTGGAGTAAAAGGGGCTG | |
| 13 | EGFR | Forward | CCAAGGCACGAGTAACAAGCT | 119 |
| 14 | Copy | Reverse | GCACATAGGTAATTTCCAAA | |
| 15 | Actin | Forward | GTCCCCTTCCCTCCTCAGAT | 130 |
| 16 | (genomic) | Reverse | CGGACTCGTCATACTCCTGC | |
| 17 | EGFR | Forward | ACTCTGAGTGCATACAGTGC | 261 |
| 18 | Isoform A | Reverse | TCGTTGGACAGCCTTCAAGAC | |
| 19 | EGFR | Forward | ACTCTGAGTGCATACAGTGC | 478 |
| 20 | Isoform D | Reverse | TGAAGGCATGAGGCTCAGTG | |
| 21 | Actin | Forward | ATGTTTGAGACCTTCACACC | 198 |
| 22 | (mRNA) | Reverse | AGGTAGTCAGTCAGGTCCCGG | |
| 23 | EGFR AS1 | Forward | TCCAGGTGAAGACGCATGAA | 78 |
| 24 | | Reverse | GTCTTTTGCAGGCACAGCTT | |

TABLE 1-continued

Table of sequences

| SEQ ID NO | Target/ description | Primer | Sequence 5'-3' | Amplicon size (bp), if applicable |
|---|---|---|---|---|
| 25 | LNA against EGFR-AS1 (LNA-AS1) | n.a. | ATCGCAAAGGTAATC | n.a. |
| 26 | Negative control (LNA-i-miR-NC) | n.a. | AACACGTCTATACGC | n.a. |
| 27 | EGFR as shown in NCBI sequence ID: NM_005228.4 | n.a. | GTCCGGGCAGCCCCCGGCGCAGCGCGGCC GCAGCAGCCTCCGCCCCCCGCACGGTGTG AGCGCCCGACGCGGCCGAGGCGGCCGGA GTCCCGAGCTAGCCCCGGCGGCCGCCGCC GCCCAGACCGGACGACAGGCCACCTCGTC GGCGTCCGCCCGAGTCCCCGCCTCGCCGC CAACGCCACAACCACCGCGCACGGCCCCC TGACTCCGTCCAGTATTGATCGGGAGAGC CGGAGCGAGCTCTTCGGGGAGCAGCGATG CGACCCTCCGGGACGGCCGGGGCAGCGCT CCTGGCGCTGCTGGCTGCGCTCTGCCCGGC GAGTCGGGCTCTGGAGGAAAAGAAAGTTT GCCAAGGCACGAGTAACAAGCTCACGCAG TTGGGCACTTTTGAAGATCATTTTCTCAGC CTCCAGAGGATGTTCAATAACTGTGAGGT GGTCCTTGGGAATTTGGAAATTACCTATGT GCAGAGGAATTATGATCTTTCCTTCTTAAA GACCATCCAGGAGGTGGCTGGTTATGTCC TCATTGCCCTCAACACAGTGGAGCGAATT CCTTTGGAAAACCTGCAGATCATCAGAGG AAATATGTACTACGAAAATTCCTATGC CTTAGCAGTCTTATCTAACTATGATGCAAA TAAAACCGGACTGAAGGAGCTGCCCATGA GAAATTTACAGGAAATCCTGCATGGCGCC GTGCGGTTCAGCAACAACCCTGCCCTGTG CAACGTGGAGAGCATCCAGTGGCGGGACA TAGTCAGCAGTGACTTTCTCAGCAACATGT CGATGGACTTCCAGAACCACCTGGGCAGC TGCCAAAAGTGTGATCCAAGCTGTCCCAA TGGGAGCTGCTGGGGTGCAGGAGAGGAG AACTGCCAGAAACTGACCAAAATCATCTG TGCCCAGCAGTGCTCCGGGCGCTGCCGTG GCAAGTCCCCCAGTGACTGCTGCCACAAC CAGTGTGCTGCAGGCTGCACAGGCCCCCG GGAGAGCGACTGCCTGGTCTGCCGCAAAT TCCGAGACGAAGCCACGTGCAAGGACACC TGCCCCCCACTCATGCTCTACAACCCCACC ACGTACCAGATGGATGTGAACCCCGAGGG CAAATACAGCTTTGGTGCCACCTGCGTGA AGAAGTGTCCCCGTAATTATGTGGTGACA GATCACGGCTCGTGCGTCCGAGCCTGTGG GGCCGACAGCTATGAGATGGAGGAAGAC GGCGTCCGCAAGTGTAAGAAGTGCGAAGG GCCTTGCCGCAAAGTGTGTAACGGAATAG GTATTGGTGAATTTAAAGACTCACTCTCCA TAAATGCTACGAATATTAAACACTTCAAA AACTGCACCTCCATCAGTGGCGATCTCCA CATCCTGCCGGTGGCATTTAGGGGTGACT CCTTCACACATACTCCTCCTCTGGATCCAC AGGAACTGGATATTCTGAAAACCGTAAAG GAAATCACAGGGTTTTTGCTGATTCAGGCT TGGCCTGAAAACAGGACGGACCTCCATGC CTTTGAGAACCTAGAAATCATACGCGGCA GGACCAAGCAACATGGTCAGTTTTCTCTTG CAGTCGTCAGCCTGAACATAACATCCTTG GGATTACGCTCCCTCAAGGAGATAAGTGA TGGAGATGTGATAATTTCAGGAAACAAAA ATTTGTGCTATGCAAATACAATAAACTGG AAAAAACTGTTTGGGACCTCCGGTCAGAA AACCAAAATTATAAGCAACAGAGGTGAAA | n.a. |

TABLE 1-continued

Table of sequences

| SEQ ID NO | Target/ description | Primer | Sequence 5'-3' | Amplicon size (bp), if applicable |
|---|---|---|---|---|
| | | | ACAGCTGCAAGGCCACAGGCCAGGTCTGC | |
| | | | CATGCCTTGTGCTCCCCCGAGGGCTGCTGG | |
| | | | GGCCCGGAGCCCAGGGACTGCGTCTCTTG | |
| | | | CCGGAATGTCAGCCGAGGCAGGGAATGCG | |
| | | | TGGACAAGTGCAACCTTCTGGAGGGTGAG | |
| | | | CCAAGGGAGTTTGTGGAGAACTCTGAGTG | |
| | | | CATACAGTGCCACCCAGAGTGCCTGCCTC | |
| | | | AGGCCATGAACATCACCTGCACAGGACGG | |
| | | | GGACCAGACAACTGTATCCAGTGTGCCCA | |
| | | | CTACATTGACGGCCCCCACTGCGTCAAGA | |
| | | | CCTGCCCGGCAGGAGTCATGGGAGAAAAC | |
| | | | AACACCCTGGTCTGGAAGTACGCAGACGC | |
| | | | CGGCCATGTGTGCCACCTGTGCCATCCAA | |
| | | | ACTGCACCTACGGATGCACTGGGCCAGGT | |
| | | | CTTGAAGGCTGTCCAACGAATGGGCCTAA | |
| | | | GATCCCGTCCATCGCCACTGGGATGGTGG | |
| | | | GGGCCCTCCTCTTGCTGCTGGTGGTGGCCC | |
| | | | TGGGGATCGGCTCTTCATGCGAAGGCGC | |
| | | | CACATCGTTCGGAAGCGCACGCTGCGGAG | |
| | | | GCTGCTGCAGGAGAGGGAGCTTGTGGAGC | |
| | | | CTCTTACACCCAGTGGAGAAGCTCCCAAC | |
| | | | CAAGCTCTCTTGAGGATCTTGAAGGAAAC | |
| | | | TGAATTCAAAAAGATCAAAGTGCTGGGCT | |
| | | | CCGGTGCGTTCGGCACGGTGTATAAGGGA | |
| | | | CTCTGGATCCCAGAAGGTGAGAAAGTTAA | |
| | | | AATTCCCGTCGCTATCAAGGAATTAAGAG | |
| | | | AAGCAACATCTCCGAAAGCCAACAAGGAA | |
| | | | ATCCTCGATGAAGCCTACGTGATGGCCAG | |
| | | | CGTGGACAACCCCCACGTGTGCCGCCTGC | |
| | | | TGGGCATCTGCCTCACCTCCACCGTGCAGC | |
| | | | TCATCACGCAGCTCATGCCCTTCGGCTGCC | |
| | | | TCCTGGACTATGTCCGGGAACACAAAGAC | |
| | | | AATATTGGCTCCCAGTACCTGCTCAACTGG | |
| | | | TGTGTGCAGATCGCAAAGGGCATGAACTA | |
| | | | CTTGGAGGACCGTCGCTTGGTGCACCGCG | |
| | | | ACCTGGCAGCCAGGAACGTACTGGTGAAA | |
| | | | ACACCGCAGCATGTCAAGATCACAGATTT | |
| | | | TGGGCTGGCCAAACTGCTGGGTGCGGAAG | |
| | | | AGAAAGAATACCATGCAGAAGGAGGCAA | |
| | | | AGTGCCTATCAAGTGGATGGCATTGGAAT | |
| | | | CAATTTTACACAGAATCTATACCCACCAG | |
| | | | AGTGATGTCTGGAGCTACGGGGTGACTGT | |
| | | | TTGGGAGTTGATGACCTTTGGATCCAAGC | |
| | | | CATATGACGGAATCCCTGCCAGCGAGATC | |
| | | | TCCTCCATCCTGGAGAAAGGAGAACGCCT | |
| | | | CCCTCAGCCACCCATATGTACCATCGATGT | |
| | | | CTACATGATCATGGTCAAGTGCTGGATGA | |
| | | | TAGACGCAGATAGTCGCCCAAAGTTCCGT | |
| | | | GAGTTGATCATCGAATTCTCCAAAATGGC | |
| | | | CCGAGACCCCCAGCGCTACCTTGTCATTCA | |
| | | | GGGGGATGAAAGAATGCATTTGCCAAGTC | |
| | | | CTACAGACTCCAACTTCTACCGTGCCCTGA | |
| | | | TGGATGAAGAAGACATGGACGACGTGGTG | |
| | | | GATGCCGACGAGTACCTCATCCCACACGCA | |
| | | | GGGCTTCTTCAGCAGCCCCTCCACGTCACG | |
| | | | GACTCCCCTCCTGAGCTCTCTGAGTGCAAC | |
| | | | CAGCAACAATTCCACCGTGGCTTGCATTG | |
| | | | ATAGAAATGGGCTGCAAAGCTGTCCCATC | |
| | | | AAGGAAGACAGCTTCTTGCAGCGATACAG | |
| | | | CTCAGACCCCACAGGCGCCTTGACTGAGG | |
| | | | ACAGCATAGACGACACCTTCCTCCCAGTG | |
| | | | CCTGAATACATAAACCAGTCCGTTCCCAA | |
| | | | AAGGCCCGCTGGCTCTGTGCAGAATCCTG | |
| | | | TCTATCACAATCAGCCTCTGAACCCCGCGC | |
| | | | CCAGCAGAGACCCACACTACCAGGACCCC | |
| | | | CACAGCACTGCAGTGGGCAACCCCGAGTA | |
| | | | TCTCAACACTGTCCAGCCCACCTGTGTCAA | |
| | | | CAGCACATTCGACAGCCCTGCCCACTGGG | |
| | | | CCCAGAAAGGCAGCCACCAAATTAGCCTG | |
| | | | GACAACCCTGACTACCAGCAGGACTTCTT | |

TABLE 1-continued

Table of sequences

| SEQ ID NO | Target/ description | Primer | Sequence 5'-3' | Amplicon size (bp), if applicable |
|---|---|---|---|---|
| | | | TCCCAAGGAAGCCAAGCCAAATGGCATCT | |
| | | | TTAAGGGCTCCACAGCTGAAAATGCAGAA | |
| | | | TACCTAAGGGTCGCGCCACAAAGCAGTGA | |
| | | | ATTTATTGGAGCATGACCACGGAGGATAG | |
| | | | TATGAGCCCTAAAAATCCAGACTCTTTCG | |
| | | | ATACCCAGGACCAAGCCACAGCAGGTCCT | |
| | | | CCATCCCAACAGCCATGCCCGCATTAGCT | |
| | | | CTTAGACCCACAGACTGGTTTTGCAACGTT | |
| | | | TACACCGACTAGCCAGGAAGTACTTCCAC | |
| | | | CTCGGGCACATTTTGGGAAGTTGCATTCCT | |
| | | | TTGTCTTCAAACTGTGAAGCATTTACAGAA | |
| | | | ACGCATCCAGCAAGAATATTGTCCCTTTG | |
| | | | AGCAGAAATTTATCTTTCAAAGAGGTATA | |
| | | | TTTGAAAAAAAAAAAAAGTATATGTGAGG | |
| | | | ATTTTTATTGATTGGGGATCTTGGAGTTTT | |
| | | | TCATTGTCGCTATTGATTTTTACTTCAATG | |
| | | | GGCTCTTCCAACAAGGAAGAAGCTTGCTG | |
| | | | GTAGCACTTGCTACCCTGAGTTCATCCAGG | |
| | | | CCCAACTGTGAGCAAGGAGCACAAGCCAC | |
| | | | AAGTCTTCCAGAGGATGCTTGATTCCAGT | |
| | | | GGTTCTGCTTCAAGGCTTCCACTGCAAAAC | |
| | | | ACTAAAGATCCAAGAAGGCCTTCATGGCC | |
| | | | CCAGCAGGCCGGATCGGTACTGTATCAAG | |
| | | | TCATGGCAGGTACAGTAGGATAAGCCACT | |
| | | | CTGTCCCTTCCTGGGCAAAGAAGAAACGG | |
| | | | AGGGGATGGAATTCTTCCTTAGACTTACTT | |
| | | | TTGTAAAAATGTCCCCACGGTACTTACTCC | |
| | | | CCACTGATGGACCAGTGGTTTCCAGTCAT | |
| | | | GAGCGTTAGACTGACTTGTTTGTCTTCCAT | |
| | | | TCCATTGTTTTGAAACTCAGTATGCTGCCC | |
| | | | CTGTCTTGCTGTCATGAAATCAGCAAGAG | |
| | | | AGGATGACACATCAAATAATAACTCGGAT | |
| | | | TCCAGCCCACATTGGATTCATCAGCATTTG | |
| | | | GACCAATAGCCCACAGCTGAGAATGTGGA | |
| | | | ATACCTAAGGATAGCACCGCTTTTGTTCTC | |
| | | | GCAAAAACGTATCTCCTAATTTGAGGCTC | |
| | | | AGATGAAATGCATCAGGTCCTTTGGGCA | |
| | | | TAGATCAGAAGACTACAAAAATGAAGCTG | |
| | | | CTCTGAAATCTCCTTTAGCCATCACCCCAA | |
| | | | CCCCCCAAAATTAGTTTGTGTTACTTATGG | |
| | | | AAGATAGTTTTCTCCTTTTACTTCACTTCA | |
| | | | AAAGCTTTTTACTCAAAGAGTATATGTTCC | |
| | | | CTCCAGGTCAGCTGCCCCCAAACCCCCTCC | |
| | | | TTACGCTTTGTCACACAAAAAGTGTCTCTG | |
| | | | CCTTGAGTCATCTATTCAAGCACTTACAGC | |
| | | | TCTGGCCACAACAGGGCATTTTACAGGTG | |
| | | | CGAATGACAGTAGCATTATGAGTAGTGTG | |
| | | | GAATTCAGGTAGTAAATATGAAACTAGGG | |
| | | | TTTGAAATTGATAATGCTTTCACAACATTT | |
| | | | GCAGATGTTTTAGAAGGAAAAAAGTTCCT | |
| | | | TCCTAAAATAATTTCTCTACAATTGGAAGA | |
| | | | TTGGAAGATTCAGCTAGTTAGGAGCCCAC | |
| | | | CTTTTTTCCTAATCTGTGTGTGCCCTGTAA | |
| | | | CCTGACTGGTTAACAGCAGTCCTTTGTAAA | |
| | | | CAGTGTTTTAAACTCTCCTAGTCAATATCC | |
| | | | ACCCCATCCAATTTATCAAGGAAGAAATG | |
| | | | GTTCAGAAAATATTTTCAGCCTACAGTTAT | |
| | | | GTTCAGTCACACACACATACAAAATGTTC | |
| | | | CTTTTGCTTTTAAAGTAATTTTTGACTCCC | |
| | | | AGATCAGTCAGAGCCCCTACAGCATTGTT | |
| | | | AAGAAAGTATTTGATTTTTGTCTCAATGAA | |
| | | | AATAAAACTATATTCATTTCCACTCTATTA | |
| | | | TGCTCTCAAATACCCCTAAGCATCTATACT | |
| | | | AGCCTGGTATGGGTATGAAAGATACAAAG | |
| | | | ATAAATAAAACATAGTCCCTGATTCTAAG | |
| | | | AAATTCACAATTTAGCAAAGGAAATGGAC | |
| | | | TCATAGATGCTAACCTTAAAACAACGTGA | |
| | | | CAAATGCCAGACAGGACCCATCAGCCAGG | |
| | | | CACTGTGAGAGCACAGAGCAGGGAGGTTG | |
| | | | GGTCCTGCCTGAGGAGACCTGGAAGGGAG | |

TABLE 1-continued

Table of sequences

| SEQ ID NO | Target/description | Primer | Sequence 5'-3' | Amplicon size (bp), if applicable |
|---|---|---|---|---|
| | | | GCCTCACAGGAGGATGACCAGGTCTCAGT | |
| | | | CAGCGGGGAGGTGGAAAGTGCAGGTGCAT | |
| | | | CAGGGGCACCCTGACCGAGGAAACAGCTG | |
| | | | CCAGAGGCCTCCACTGCTAAAGTCCACAT | |
| | | | AAGGCTGAGGTCAGTCACCCTAAACAACC | |
| | | | TGCTCCCTCTAAGCCAGGGGATGAGCTTG | |
| | | | GAGCATCCCACAAGTTCCCTAAAAGTTGC | |
| | | | AGCCCCCAGGGGGATTTTGAGCTATCATC | |
| | | | TCTGCACATGCTTAGTGAGAAGACTACAC | |
| | | | AACATTTCTAAGAATCTGAGATTTTATATT | |
| | | | GTCAGTTAACCACTTTCATTATTCATTCAC | |
| | | | CTCAGGACATGCAGAAATATTTCAGTCAG | |
| | | | AACTGGGAAACAGAAGGACCTACATTCTG | |
| | | | CTGTCACTTATGTGTCAAGAAGCAGATGA | |
| | | | TCGATGAGGCAGGTCAGTTGTAAGTGAGT | |
| | | | CACATTGTAGCATTAAATTCTAGTATTTTT | |
| | | | GTAGTTTGAAACAGTAACTTAATAAAAGA | |
| | | | GCAAAAGCTAAAAAAAAAAAAAAAAA | |

The invention claimed is:

1. A method of predicting susceptibility of a subject suffering from cancer to a treatment with an anti-cancer drug and treating the subject with an anti-cancer drug, wherein the method comprises detecting the presence of a genetic alteration in a long non-coding RNA (lncRNA) that resides in an antisense strand of an oncogene, wherein the genetic alteration alters or disrupts expression of the oncogene;
   wherein the oncogene is an EGFR encoding epidermal growth factor receptor; wherein the genetic alteration is a homozygous silent G>A mutation at Q787Q position in exon 20 of the oncogene EGFR; wherein the cancer is head and neck cancer; and
   administering the anti-cancer drug to the subject.

2. The method of claim 1, wherein the antisense strand of the non-coding RNA of the oncogene is EGFR-AS1 for EGFR gene.

3. The method of claim 1, wherein the head and neck cancer is head and neck squamous cell carcinoma (HNSCC) or oral squamous cell carcinoma (OSCC).

4. The method of claim 1, further comprising either one or both of the following prior to the administration of the anti-cancer drug:
   i) measuring EGFR-AS1 expression level in a subject, and determining that it is lower as compared to a control, wherein lower EGFR-AS1 expression levels indicate that the subject suffering from head and neck cancer is susceptible to a treatment with an anti-cancer drug, and/or
   ii) measuring EGFR isoform D/isoform A ratio in a subject and determining that it is higher as compared to a control, wherein higher EGFR isoform D/isoform A ratio indicates that the subject suffering from head and neck cancer is susceptible to a treatment with an anti-cancer drug,
   wherein the anti-cancer drug is a tyrosine kinase inhibitor or an EGFR inhibitor.

5. A method of predicting the susceptibility of a subject suffering from head and neck cancer to a treatment with an EGFR inhibitor and treating the subject, the method comprising:
   i) detecting the presence of a homozygous silent G>A mutation (genetic alteration) at Q787Q position in exon 20 of EGFR in the patient; and/or
   ii) measuring EGFR-AS1 expression level in a subject, and determining that it is lower as compared to a control, wherein lower EGFR-AS1 expression levels indicate that the subject suffering from head and neck cancer is susceptible to a treatment with an EGFR inhibitor;
   and
   administering the EGFR inhibitor to the subject.

6. The method of claim 5, wherein prior to the administration of the EGFR inhibitor, the method further comprises measuring EGFR isoform D/isoform A ratio in the subject, and determining that it is higher as compared to a control, wherein higher EGFR isoform D/isoform A ratio indicates that the subject suffering from head and neck cancer is susceptible to a treatment with an EGFR inhibitor.

7. The method of claim 5, wherein the head and neck cancer is head and neck squamous cell carcinoma (HNSCC) or oral squamous cell carcinoma (OSCC).

* * * * *